US012797627B2

(12) United States Patent
Gries

(10) Patent No.: US 12,797,627 B2
(45) Date of Patent: Nov. 17, 2026

(54) APPARATUS AND METHOD FOR GENERATING A MAGNETIC FIELD

(71) Applicant: Zimmer MedizinSysteme GmbH, Neu Ulm (DE)

(72) Inventor: Luka Leon Gries, Neu-Ulm (DE)

(73) Assignee: Zimmer MedizinSysteme GmbH, Neu-Ulm (DE)

( * ) Notice: Subject to any disclaimer, the term of this patent is extended or adjusted under 35 U.S.C. 154(b) by 1006 days.

(21) Appl. No.: 18/083,371

(22) Filed: Dec. 16, 2022

(65) Prior Publication Data

US 2023/0211171 A1 Jul. 6, 2023

Related U.S. Application Data

(63) Continuation-in-part of application No. 18/083,190, filed on Dec. 16, 2022, which is a continuation-in-part of application No. 17/555,805, filed on Dec. 20, 2021, now Pat. No. 12,678,632, and a continuation-in-part of application No. 17/846,724, filed on Jun. 22, 2022, now Pat. No. 12,558,561, and a continuation-in-part of application No. 18/067,052, filed on Dec. 16, 2022, now Pat. No. 12,734,372, application No. 18/083,371, filed on Dec. 16, 2022 is a continuation-in-part of application No. 18/067,052, filed on Dec. 16, 2022, now Pat. No. 12,734,372, and a continuation-in-part of application No. 17/846,724, filed on Jun. 22, 2022, now Pat. No. 12,558,561, and (Continued)

(51) Int. Cl.
*A61N 2/02* (2006.01)

(52) U.S. Cl.
CPC .................................... *A61N 2/02* (2013.01)

(58) Field of Classification Search
CPC ................................ A61N 2/02; A61N 2/006
USPC ..................................................... 600/12–15
See application file for complete search history.

(56) References Cited

U.S. PATENT DOCUMENTS 5,718,662 A * 2/1998 Jalinous ................ A61N 2/006 128/897
5,766,124 A * 6/1998 Polson .................. A61N 2/006 600/13

(Continued)

*Primary Examiner* — Sunita Reddy
(74) *Attorney, Agent, or Firm* — Nixon & Vanderhye PC

(57) ABSTRACT

A first magnetic field for application to body tissue is generated via a first inductor. A second magnetic field is also generated via a second inductor. Connecting circuitry, including at least first and second branches, is provided between an electric storage device such as a capacitor, or a capacitor arrangement comprising at least a first capacitor, and the first and second inductors. A switch forming part of the first branch electrically connects the electric storage device to the first inductor enabling electrical current to flow through the first branch and the first inductor, thereby causing the first inductor to generate the first magnetic field. The current flowing through the first branch represents a first direction of flow with respect to the electric storage device. A switch forming part of the second branch electrically connects the electric storage device to the second inductor enabling current to flow between the electric storage device and the second inductor through the second branch. The current flowing through the second branch represents a second direction of flow with respect to the electric storage device.

20 Claims, 16 Drawing Sheets

Related U.S. Application Data a continuation-in-part of application No. 17/555,805, filed on Dec. 20, 2021, now Pat. No. 12,678,632.

(56) References Cited

U.S. PATENT DOCUMENTS

| | | | | |
|---|---|---|---|---|
| 2007/0097571 | A1 * | 5/2007 | Dinh | H02M 3/1584<br>361/62 |
| 2009/0147541 | A1 * | 6/2009 | Shimada | H01F 27/38<br>336/170 |
| 2010/0152522 | A1 * | 6/2010 | Roth | A61N 2/006<br>600/13 |
| 2011/0242868 | A1 * | 10/2011 | Gray | H05B 6/06<br>363/131 |
| 2014/0035711 | A1 * | 2/2014 | Friebe | H01F 37/00<br>336/105 |
| 2016/0151637 | A1 * | 6/2016 | Abe | A61N 2/02<br>600/14 |
| 2021/0288490 | A1 * | 9/2021 | Beck | H02H 9/02 |

* cited by examiner

APPARATUS AND METHOD FOR GENERATING A MAGNETIC FIELD

This application is a Continuation-in-Part of each of U.S. patent application Ser. No. 18/083,190 filed Dec. 16, 2022, Ser. No. 18/067,052 filed Dec. 16, 2022, Ser. No. 17/555,805 filed Dec. 20, 2021, and Ser. No. 17/846,724 filed Jun. 22, 2022; and U.S. patent application Ser. No. 18/083,190 is a Continuation-in-Part of each of U.S. patent application Ser. No. 18/067,052 filed Dec. 16, 2022, Ser. No. 17/555,805 filed Dec. 20, 2021, and Ser. No. 17/846,724 filed Jun. 22, 2022, the entire contents of each of which are hereby incorporated herein by reference.

The present invention relates to an apparatus and a method for generating a magnetic field, in particular for application to (human or animal) body tissue.

The invention can in particular be used to generate an alternating magnetic field, i.e. a magnetic field whose magnetic field strength varies over time, and in particular a magnetic field whose magnetic field strength reverses its orientation over time. Such alternating magnetic fields can be used to generate a voltage in the body tissue, in particular so as to cause a neural reaction or a cellular physiological reaction in the body tissue, in particular so as to cause a muscle reaction in the body tissue. In some cases, the voltage can be sufficient to cause a therapeutic effect, or some other (desirable) effect in the body tissue, i.e. not necessarily a therapeutic effect, for example the strengthening of muscle tissue.

Various devices for generating an alternating magnetic field for application to body tissue are known in the art. FIG. 1 schematically shows a circuit diagram of a device for generating an alternating magnetic field known to the inventor (and not admitted as prior art). The circuit shown in FIG. 1 includes a capacitor 101 electrically connected, via two branches 105 and 106 of connecting circuitry, to an inductor 102. The capacitor 101 is also connected, via a switch 108, to a source of electrical energy, such as a voltage source 107. One terminal of each of the capacitor 101, inductor 102 and voltage source 107 is connected to ground (indicated by triangles towards the bottom of FIG. 1). Whilst switch 108 is shown in FIG. 1 as a separate circuit element, it can alternatively be integrated into, or form part of, voltage source 107.

A thyristor 103 forms part of the first branch 105, i.e. one terminal (in FIG. 1 the left-hand terminal, i.e. the anode) of the thyristor 103 is electrically connected to the capacitor 101. A second terminal (in FIG. 1 the right-hand terminal, i.e. the cathode) of the thyristor 103 is electrically connected to the inductor 102. A third terminal, the gate terminal of the thyristor, is electrically connected to suitable circuitry for "firing" the thyristor 103. Circuitry for firing the thyristor 103 is not shown in FIG. 1, but is known to those skilled in the art.

Similarly, a diode 104 forms part of the second branch 106, i.e. one terminal (in FIG. 1 the left-hand terminal, i.e. the cathode) of the diode 104 is electrically connected to the capacitor 101. A second terminal (in FIG. 1 the right-hand terminal, i.e. the anode) of the diode 104 is electrically connected to the inductor 102.

Accordingly, electrical current can flow between the capacitor 101 and the inductor 102 either via the first branch 105 or the second branch 106, depending on whether the thyristor 103 or the diode 104 is in a conductive state or "ON" state. In particular, the polarity of the thyristor 103 and the diode 104 is such that only one of these components is conductive at any one time. It will be appreciated that, even when the thyristor 103 or the diode 104 is in a non-conductive state, a small amount of electrical current may nevertheless flow through these components. For the purposes of the present application, the terms "conductive (state)" and "non-conductive (state)" and similar are preferably to be interpreted accordingly.

The direction of conventional current in an electrical circuit is defined as the direction in which positive charges flow. Negatively charged carriers, such as the electrons, therefore flow in the opposite direction of conventional current flow in an electrical circuit. In accordance with this convention, electrical current flowing from the capacitor 101 to the inductor 102 will (only) flow through the first branch 105 (assuming the thyristor 103 is in a conductive state), whereas electrical current flowing from the inductor 102 to the capacitor 101 will (only) flow through the second branch 106 (assuming the diode 104 is in a conductive state).

The inductor 102 can be brought into proximity with body tissue so that any magnetic field generated by inductor 102 is applied to the body tissue.

Typically, the operation of the device shown in FIG. 1 is as follows. The capacitor 101 is electrically charged by voltage source 107. To this end, switch 108 is closed at a suitable time so as to electrically connect voltage source 107 to capacitor 101. Switch 108 can be operated by suitable circuitry, which is again not shown in FIG. 1 but will be familiar to those skilled in the art. Once the capacitor 101 has been charged, either for a certain period of time or up to a certain voltage, switch 108 is opened. In the example shown in FIG. 1, the capacitor 101 will be charged such that the (in FIG. 1) upper terminal will be positive and the lower terminal will be negative. This is also indicated by the symbols "+" and "−" next to voltage source 107.

Initially, the electrical charge now stored in capacitor 101 will remain in capacitor 101 since the diode 104 is in a non-conductive state. Electrical current can (initially) also not flow from capacitor 101 to inductor 102 via the first branch 105, unless and until thyristor 103 is fired via its gate terminal.

Next, thyristor 103 is fired via its gate terminal. Current can now flow from capacitor 101 to inductor 102, thereby enabling inductor 102 to generate a magnetic field. As is known in the art, thyristor 103 remains in a conductive state even if the signal (gate current) which fired thyristor 103 is no longer present at its gate terminal.

While current flows from capacitor 101 through the first branch 105 and through inductor 102, the charge stored in capacitor 101 (and thus the voltage between the two terminals of capacitor 101) decreases. This decrease in voltage approximately follows a cosine shape, starting at an initial maximum value at the time when thyristor 103 is fired.

Due to energy losses in the circuit of FIG. 1, the voltage between the two terminals of capacitor 101 does not follow an exact cosine shape over time. Instead, the voltage more closely follows a cosine shape with a decaying amplitude, although even this may only be an approximation. The same applies to other voltages, currents or other variables which are described herein as (approximately) following a sine or cosine shape. This applies both to the circuit of FIG. 1 and to embodiments of the present invention. Accordingly, as used herein, the terms "cosine shape", "sine shape" and similar are to be understood to include (an approximation of) a cosine or sine shape with a decaying amplitude.

While the voltage between the two terminals of capacitor 101 decreases, the current through inductor 102 increases, starting at a value of zero and approximately following a sine shape, up to a maximum value. The current through inductor 102 reaches its maximum value substantially at the same time as the charge stored in capacitor 101 has dropped to zero. The period of time from the initial firing of thyristor 103 up to the point in time when the current through inductor 102 reaches its maximum value can be regarded as a quarter wave, or $\pi/2$.

At the time of $\pi/2$, a magnetic field generated by the current through inductor 102 is also at a maximum value, whilst the electrical energy stored in capacitor 101 is zero. In other words, the electrical energy that was initially stored in capacitor 101 has now been converted into magnetic energy, i.e. the magnetic field generated by the current through inductor 102. The energy is now stored in the magnetic field. As the magnetic field resists its decrease, current continues to flow through inductor 102 and through the first branch 105. The diode 104 is still in a non-conductive state. Accordingly, this continued current flow charges capacitor 101, but this time with opposite polarity compared with its initial state. As capacitor 101 is charged up to a negative maximum value (approximately corresponding to the initial maximum charge, but of opposite polarity), the current through inductor 102 and accordingly also the magnetic field decreases until, one half wave after initial firing of thyristor 103, or at the time of Tr, it has become zero. At this time, the charge (or voltage) of capacitor 101 has reached its maximum value of opposite polarity. Between $\pi/2$ and $\pi$, the voltage of capacitor 101 and current through inductor 102 continue to follow the approximated cosine and sine shapes, respectively.

Approximately at the end of this first half wave, thyristor 103 becomes non-conductive and diode 104 becomes conductive, in a or its forward direction. In the example shown in FIG. 1, this forward direction corresponds to a current direction from inductor 102 to capacitor 101. The process described above in connection with the first half wave is then effectively repeated during a second half wave, except that, at the time of $\pi$ (i.e. at a point in time at the end of the first half wave or at the beginning of the second half wave), the polarity of the voltage of capacitor 101 is the opposite of the initial polarity, and likewise the current direction through inductor 102 during the second half wave is the opposite of the current direction through inductor 102 during the first half wave. Further, the current between inductor 102 and capacitor 101 flows through the second branch 106, rather than through the first branch 105. The voltage of capacitor 101 and current through inductor 102 continue to follow, respectively, the (approximated) cosine and sine shapes which they started during the first half wave.

Eventually, after the second half wave, or at the time of $2\pi$, the system represented by the circuit shown in FIG. 1 has returned to its initial state, i.e. capacitor 101 is charged up to a maximum value and with the initial polarity, while the current through inductor 102 has returned to zero. Diode 104 becomes non-conductive at this stage. A complete cycle has been performed (two half waves). The process can then be repeated.

It is an object of the present invention to provide an apparatus and a method which offers more flexibility than the circuit described above in connection with FIG. 1.

Accordingly, the present invention provides an apparatus and a method in accordance with the independent claims. Further embodiments are set out in the dependent claims.

In a first aspect of the present disclosure, there is provided an apparatus for generating a magnetic field for application to body tissue, the apparatus comprising:

an electric storage device for storing electrical energy;

a first inductor for generating a magnetic field for application to body tissue;

connecting circuitry between the electric storage device and the first inductor, wherein the connecting circuitry comprises at least a first branch and a second branch;

a switching device, wherein the switching device forms part of the first branch, wherein the switching device is configured to electrically connect the electric storage device to the first inductor in order to enable electrical current to flow through the first branch and through the first inductor, caused by the electrical energy stored by means of the electric storage device, thereby causing the first inductor to generate the magnetic field, wherein the electrical current flowing through the first branch represents a first current direction of current flow between the electric storage device and the first inductor;

an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction; and a second inductor, wherein the second inductor forms part of either the first branch or the second branch.

Accordingly, if, for example, the second inductor forms part of the second branch, current flowing in the second current direction would also flow through the second inductor—unless the second inductor is bypassed or short-circuited (which will be explained below).

In certain embodiments, the apparatus according to the first aspect can be constructed in a similar way to the circuit described in connection with FIG. 1. However, the addition of the second inductor in the first branch or the second branch constitutes a significant difference, not only in terms of the construction of the apparatus but also in terms of the operation of the apparatus, as will be explained below.

The electric storage device, in particular if a capacitor is used as electric storage device, together with the first inductor and the connecting circuitry can effectively be regarded as a resonant circuit (or LC circuit). However, whereas in a typical resonant circuit the electrical current would normally take the same path through the resonant circuit regardless of the direction in which it flows at any one time, in embodiments according to the first aspect, the electrical current would flow either through the first branch or the second branch, depending on the direction of current flow between the electric storage device and the first inductor.

Further, after one complete cycle (two half waves) and assuming that the switching device has become non-conductive after the first half wave, the current flow stops until the switching device is operated (e.g. fired) again to allow current to flow through the first branch. Nevertheless, the behavior can be regarded as somewhat similar to that of a resonant circuit.

Assuming ideal components, the resonant frequency $\omega_0$ of a resonant circuit (in the following simply "frequency") is determined by the values of the inductance L and the capacitance C of the circuit, according to $$\omega_0 = \frac{1}{\sqrt{LC}}.$$

In an actual (non-ideal) circuit, other factors known to those skilled in the art will lead to slightly different results, but the above formula can still serve as an approximation, including for the purpose of embodiments of the present invention. Assuming again that a capacitor is used as electric storage device in the apparatus according to the first aspect, the capacitance C of the circuit is the same regardless of whether the electrical current flows through the first branch or the second branch. However, due to the additional second inductor in either the first branch or the second branch, the applicable inductance of the circuit depends on whether the current flows through the first branch or the second branch. Applying this to a typical resonant circuit, this would mean that the frequency $\omega_0$ of the resonant circuit would depend on whether the current flows through the first branch or the second branch. In other words, the respective durations of the two half waves of a full cycle would be different. In embodiments of the first aspect, the respective durations of the two half waves will also be different due to the addition of the second conductor in either the first branch or the second branch.

For the sake of simplicity, the system comprising the electric storage device, the first inductor and the first and/or second branch of the connecting circuitry, one of which will include the second inductor, will be referred to as a resonant circuit even though, strictly speaking, it does not necessarily constitute a resonant circuit. Similarly, a reference to the frequency of the resonant circuit is preferably intended to be understood not only to refer to an actual oscillation (in particular several consecutive oscillations), but also a reference to the duration of a half wave, or even more generally a reference to the rate of change (over time) of the electric current in the resonant circuit, a rate of change (over time) of a voltage at one of its components, or a rate of change (over time) of any other electrical property of the resonant circuit.

Suitable inductors for use as the first inductor and/or the second inductor are known in the art. They may in particular comprise at least one set of turns (of a wire) of any suitable shape, such as generally circular, hexagonal or rectangular turns. These turns may or may not be wound on a core.

The switching device of the apparatus according to the first aspect may comprise a thyristor. Using a thyristor may be preferred over other switching devices since, once it has been fired, the thyristor remains in the conductive state even once the gate signal has been removed. Further, the thyristor changes into the non-conductive state once the polarity at its terminals (anode and cathode) is reversed.

However, other types of switching devices can be used instead of a ("normal") thyristor. For example, a gate turn-off (GTO-thyristor) can be used. This essentially has the same characteristics as a "normal" thyristor, but additionally it can be brought into the non-conductive state by applying a gate signal of the opposite polarity compared with the initial gate signal for firing the GTO-thyristor.

Further alternative switching devices include, without limitation, IGBT, FET or any other switching devices which can be switched on and off at appropriate times, in particular switched off after the first half wave.

If a switching device is used which actively needs to be switched off in order to revert to the non-conductive or "OFF" state, suitable switching circuitry may be provided. This can, for example, include a (micro-)controller, which may be programmed so as to switch the switching device on and/or off at desired points in time. As an alternative, or in addition, additional (analog) circuitry may be provided for switching the switching device off depending on a voltage which is present at a point in the first branch, in particular a voltage which is present at a terminal of the switching device which, as part of the first branch, is connected to the first inductor.

In the sense of the present invention, the term "electrical connection" is preferably intended to be understood to mean a connection enabling an electrical current to flow, in particular an electrical current of substantial magnitude. Such electric connection may be accomplished by a conductor such as a metallic wire, but may also involve semiconductor components in an ON-state. By way of contrast, the term "electrical connection" is preferably not intended to cover a semiconductor component in an OFF-state, even though an electrical current (such as a reverse leakage current in a diode or thyristor) may flow through such a semiconductor component when in the OFF-state. Any such reverse leakage current would typically be significantly smaller than an electrical current able to flow when the semiconductor component is in the ON-state. The term "electrically connect" is to be understood in a corresponding manner.

In embodiments of the first aspect, various components can be used as the electric (or electronic) component or as part of an assembly of electric (or electronic) components in the second branch. This includes diodes, in particular those with a p-n junction or a metal-semiconductor junction (Schottky contact). More generally, it includes components which have a similar functionality as a diode, including rectifiers such as electrolytic rectifiers, mercury-arc rectifiers, plate rectifiers (metal rectifiers, in particular selenium rectifiers) and vacuum tube rectifiers (vacuum tube diodes).

The components listed in the preceding paragraph can be regarded as passive rectifiers, i.e. rectifiers which do not require any additional circuitry to influence the behavior of the rectifier. As an alternative, or in addition, active switching devices can be used, which can actively be switched by additional circuitry (which additional circuitry may be regarded as part of the assembly of electric or electronic components). Such circuitry may comprise analog circuitry and/or a microcontroller. Such (active) switching devices can be used instead of, for example, a diode in the second branch in any embodiments of the present invention.

In one embodiment, the apparatus further comprises circuitry to selectively bypass or short-circuit the second inductor in order to selectively vary an inductance of the branch of which the second inductor forms a part. Such circuitry to selectively bypass or short-circuit the second inductor may comprise an electrical connection between the two terminals of the second inductor, whereby this electrical connection comprises a further switching device so as to selectively interrupt or close this electrical connection. Assuming a relatively low-ohmic electrical connection is used to bypass or short-circuit the second inductor, electrical current through the branch of which the second inductor forms a part will (almost) exclusively flow through this bypass circuitry rather than through the second inductor (when the further switching device as part of this bypass circuitry is closed). Accordingly, if the bypass circuitry is closed, the inductance of the branch of which the second inductor forms a part is reduced when compared with a situation where the bypass circuitry is interrupted. This variance in inductance also has the effect of varying the frequency of the resonant circuit. In particular, when the current flows through the second inductor, the frequency of the resonant circuit is lower (i.e. the respective half wave then has a longer duration) than when the second inductor is bypassed. Further, when the current flows through the second inductor, the magnitude of the current through the resonant circuit is lower than when the second inductor is bypassed.

In one embodiment, an inductance of the second inductor is one of:

discretely variable; and substantially continuously variable.

Inductors of discretely variable or substantially continuously variable inductance are well known in the art. If the second inductor comprises a coil with a set of turns, the inductance can be varied discretely, by bypassing one or more (entire) turns or by bypassing a fraction of turns (for example three quarters of a turn or 5.375 turns). By using a variometer as the second inductor, the inductance can be varied substantially continuously. Other possible implementations of inductors of (continuously) variable inductance include inductors with a core, e.g. a coil with a set of turns wound around a core, whereby the core is (partially) introduced into, or withdrawn from, the coil.

In one embodiment, the apparatus further comprises one or more further inductors forming part of the branch of which the second inductor forms a part.

It is envisaged that the further inductors would be connected in series with the second inductor, although it would also be possible to connect them in parallel to the second inductor. Using two or more further inductors, it is also possible to use a combination of serial and parallel connections for the second and the further inductors.

In one embodiment, the apparatus further comprises circuitry to selectively bypass or short-circuit the second inductor and/or one or more of the one or more further inductors in order to selectively vary an inductance of the branch of which the second inductor forms a part.

The effect of bypassing or short-circuiting the second inductor has already been described above. Bypassing or short-circuiting one or more of the one or more further inductors, either as an alternative, or in addition, to bypassing or short-circuiting the second inductor has a corresponding effect, including the effect of varying the frequency of the resonant circuit and the effect of varying the magnitude of the current through the branch of which the second inductor forms a part.

In one embodiment, an inductance of the second inductor and/or of at least one of the one or more further inductors is one of:

discretely variable; and substantially continuously variable.

Again, inductors with a discretely variable inductance or a substantially continuously variable inductance have already been explained above in connection with the second inductor. This can apply in like manner to the one or more further inductors.

Using inductors with a discretely or substantially continuously variable inductance can be used in combination with circuitry for bypassing or short-circuiting the second inductor and/or one or more of the further inductors, but can also be used without such bypass circuitry. By using inductors with a variable inductance in combination with bypass circuitry, it is possible for the apparatus (the resonant circuit) to cover potentially a large variety of different frequencies, which may be variable in a discrete or substantially continuous manner.

In one embodiment, the inductances of the second inductor and of the one or more further inductors are chosen such that the inductance of the branch of which the second inductor forms a part is one of:

discretely variable; and substantially continuously variable from a minimum value up to a maximum value, wherein the minimum value corresponds to an inductance of the branch of which the second inductor forms a part when the second and the further inductors are bypassed or short-circuited; and wherein the maximum value corresponds to an inductance of the branch of which the second inductor forms a part when the second and the further inductors are not bypassed and not short-circuited and the inductance of the second inductor and/or of at least one of the one or more further inductors is at a maximum.

For example, if the second inductor and the one or more further inductors are connected in series, their inductances are added to result in a (total) inductance of the branch of which the second inductor forms a part. By selectively bypassing or short-circuiting the second and/or further inductors or by varying their individual inductances, the (total) inductance of the respective branch can be varied over a wide range.

In one embodiment, the first inductor comprises at least one set of turns, preferably at least one set of generally circular, hexagonal or rectangular turns, wherein the turns of the at least one set of turns are preferably arranged such that each turn generates a contribution towards the magnetic field when the electrical current flows through the first inductor, wherein the contributions generated by each turn are superimposed in a positive manner, wherein the first inductor is disposed within a casing connected to a conduit through which extends at least one cable for supplying electrical power to the at least one set of turns, and wherein the second inductor is not disposed within said casing.

According to this embodiment, the first inductor may for example be disposed in a casing made of plastics material, which may be separate from, and separately movable with respect to, a unit such as a housing or cabinet accommodating the electric storage device, the switching device and the electric component or assembly of electric components, as well as the first and second branch of the connecting circuitry. The casing which houses the first inductor can be connected to the cabinet by the conduit accommodating the cable for supplying electrical power to the first inductor. An arrangement in which the first inductor and the casing which houses the first inductor is connected to other components of the apparatus by means of a conduit such that the first inductor can be moved relative to such other components can advantageously be used to bring the first inductor in proximity with body tissue without moving these other components (e.g. a cabinet which houses these other components and which may be much larger and heavier than the first inductor and the casing accommodating the first inductor).

In one embodiment, the electric storage device comprises a pulse capacitor which can be charged by a charging circuit.

The charging circuit may form part of the apparatus, or may be provided as a separate device for connection to the apparatus of the first aspect. The charging circuit may in particular comprise a voltage source and a switch to selectively connect the voltage source to the capacitor.

In a second aspect of the present disclosure, there is provided an apparatus for generating a magnetic field for application to body tissue, the apparatus comprising:

an electric storage device for storing electrical energy;

a first inductor for generating a magnetic field for application to body tissue;

connecting circuitry between the electric storage device and the first inductor, wherein the connecting circuitry comprises at least a first branch and a second branch;

a switching device, wherein the switching device forms part of the first branch, wherein the switching device is configured to electrically connect the electric storage device to the first inductor in order to enable electrical current to flow through the first branch and through the first inductor, caused by the electrical energy stored by means of the electric storage device, thereby causing the first inductor to generate the magnetic field, wherein the electrical current flowing through the first branch represents a first current direction of current flow between the electric storage device and the first inductor; and an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction;

wherein a total inductance of the first branch differs from a total inductance of the second branch by one of:

at least a factor of 1.5,
at least a factor of 2,
at least a factor of 5,
at least a factor of 10,
at least a factor of 50,
at least a factor of 100,
at least a factor of 500,
at least a factor of 1000,
at least a factor of 2000,
at least a factor of 5000,
at least a factor of 10000.

Pursuant to the second aspect, the inventor has recognized that the various components of the apparatus are not "ideal" components in the electrical sense. For example, the individual components such as the electric storage device, the first inductor, the switching device and the electric components or assembly of electric components forming part of the second branch, as well as the connecting circuitry would typically have one or more of a parasitic resistance, capacitance and inductance. In particular, both the first branch and the second branch will have a non-zero inductance. However, by ensuring that the inductance of the first branch differs from the inductance of the second branch (at least) by one of the factors stated above, the frequency respectively associated with the first and the second branch (each in combination with the electric storage device and the first inductor) will also be different, in particular significantly different.

The difference in inductance between the first branch and the second branch can be achieved in particular by including a second inductor (and potentially further inductors) in one of the branches, as has been explained in connection with the first aspect.

In a third aspect of the present disclosure, there is provided a method of generating a magnetic field, the method comprising:

providing an apparatus according to the first aspect;

storing electrical energy in the electric storage device;

switching the switching device so as to electrically connect the electric storage device to the first inductor and thereby enabling electrical current to flow through the first branch and through the first inductor, caused by the electrical energy stored by means of the electric storage device, thereby causing the first inductor to generate the magnetic field; and enabling electrical current to flow between the electric storage device and the first inductor through the second branch via said electric component or assembly of electric components.

In one embodiment, the apparatus used in the third aspect is operated in a pulsed manner, wherein the electrical current flowing through the first branch represents a first half pulse and wherein the electrical current flowing through the second branch represents a second half pulse, wherein a duration of the second half pulse is different from a duration of the first half pulse.

The difference in duration of the two half pulses stems from the difference in inductance of the first branch and the second branch, in particular due to the second (and any further) inductors forming part of one of the branches.

In one embodiment, the method further comprises selectively bypassing or short-circuiting the second inductor or varying an inductance of the second inductor, thereby selectively varying an inductance of the branch of which the second inductor forms a part.

The bypassing or short-circuiting of the second inductor, as well as the varying of the inductance of the second inductor has already been explained in connection with the first aspect.

In one embodiment, selectively bypassing or short-circuiting the second inductor or varying the inductance of the second inductor comprises selectively bypassing or short-circuiting the second inductor or varying the inductance of the second inductor at one of:

during the first half pulse,
during the second half pulse,
between the first half pulse and the second half pulse, and
between the second half pulse and a subsequent pulse.

Suitable (switching) circuitry can be used for actively bypassing or for short-circuiting the second inductor or for varying the inductance of the second inductor. Depending on when this bypassing, short-circuiting or varying takes place, different effects can be achieved: if done during the first half pulse (and assuming that the second inductor forms part of the first branch), the frequency of the resonant circuit is changed during the first half pulse, and accordingly the duration of the first half pulse is changed part-way through the first half pulse. Similarly, if done during the second half pulse (and assuming that the second inductor forms part of the second branch), the frequency of the resonant circuit is changed during the second half pulse, and accordingly the duration of the second half pulse is changed part-way through the second half pulse. In both cases, the signal (e.g. the current through the first inductor) changes its shape at the time when the second inductor is bypassed or short-circuited or its inductance is varied. That is, it does not continue to follow the same shape of the half pulse of the (approximated) sinewave that it followed initially, but instead continues along the shape of a different (approximated) sinewave (of a different pulse duration). If the second inductor is bypassed or short-circuited or its inductance is varied between the first half pulse and the second half pulse, the shape of each half pulse (approximately) resembles a half pulse of a sinewave. However, the duration and amplitude of the two half pulses will be different. The same applies, mutatis mutandis, if the second inductor is bypassed or short-circuited or its inductance is varied between one (full) pulse and the next (full) pulse.

A corresponding effect can be achieved by initially bypassing or short-circuiting the second inductor and interrupting the bypass or short-circuit either during the first half pulse, during the second half pulse, between the two half pulses or between one (full) pulse and the next (full) pulse.

In one embodiment, the method further comprises bringing the first inductor into proximity with body tissue, or bringing the body tissue into proximity with the first inductor, so that the magnetic field is present in said body tissue.

This may in particular be used for therapeutic purposes, but can also be used for non-therapeutic purposes.

As the second inductor influences the frequency of the resonant circuit and the magnitude of the current through the first inductor, the second inductor also has an influence on the magnetic field generated by the first inductor, which can be used to achieve particular effects in the body tissue.

According to this embodiment, bringing the first inductor into proximity with body tissue can for example be accomplished by moving the first inductor, sometimes also called applicator coil, towards body tissue, or by moving it along the body surface of a person or animal. An example of bringing the body tissue into proximity with the first inductor can involve the use of the first inductor in a (temporarily) fixed position, and a person or animal approaching the first inductor. Such a first inductor in a fixed position may for example be attached to, or integrated into, a chair or similar.

Also, it is possible first to bring the first inductor into proximity with body tissue (or to bring the body tissue into proximity with the first inductor) and then to generate the magnetic field, or vice versa.

The distance between the first inductor and the body tissue may for example be a few millimeters or centimeters, although larger distances (such as several tens of centimeters) may also be considered.

In one embodiment, the method further comprises varying the magnetic field in the body tissue so as to generate a voltage in the body tissue or to cause a movement of charges in the body tissue.

As the magnetic field in the body tissue varies with the current through the first inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction, in the body tissue, wherein preferably the voltage (or the movement of charges) is sufficient to cause a therapeutic effect.

A variety of effects can be achieved in a targeted manner using the apparatus of the first aspect or the method of the third aspect, in particular by suitable choice of the second inductor and, if applicable, bypassing or short-circuiting the second inductor or varying the inductance.

In a fourth aspect of the present disclosure, there is provided an apparatus for use with a first inductor for generating a magnetic field for application to body tissue, the apparatus comprising:

an electric storage device for storing electrical energy;

a terminal for connection to the first inductor for generating a magnetic field for application to body tissue;

connecting circuitry between the electric storage device and said terminal, wherein the connecting circuitry comprises at least a first branch and a second branch;

a switching device, wherein the switching device forms part of the first branch, wherein the switching device is configured to electrically connect the electric storage device to said terminal so as to enable electrical current to flow through the first branch and through the first inductor via said terminal when the first inductor is connected to the apparatus via said terminal, caused by the electrical energy stored by means of the electric storage device, thereby causing the first inductor to generate the magnetic field, wherein the electrical current flowing through the first branch represents a first current direction of current flow between the electric storage device and said terminal;

an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch via said terminal when the first inductor is connected to the apparatus via said terminal, wherein the current flow in the forward direction represents a second current direction of current flow between the electric storage device and the first inductor, the second current direction being opposite the first current direction; and a second inductor, wherein the second inductor forms part of either the first branch or the second branch.

The apparatus of the fourth aspect is similar to the apparatus of the first aspect. However, in contrast to the first aspect, the first inductor mentioned in connection with the fourth aspect does not form part of the apparatus of the fourth aspect. Instead, the apparatus of the fourth aspect has a terminal (such as an electric socket or similar) for connection to the first inductor. Accordingly, a number of (different) inductors, for example inductors having different shapes, inductances or other characteristics, can selectively be connected to the apparatus of the fourth aspect and used as the first inductor.

In a fifth aspect of the present disclosure, there is provided an apparatus for generating a magnetic field for application to body tissue, the apparatus comprising:

an electric storage device for storing electrical energy;

a first inductor for generating a magnetic field for application to body tissue;

connecting circuitry between the electric storage device and the first inductor, wherein the connecting circuitry comprises at least a first branch and a second branch;

a switching device, wherein the switching device forms part of the first branch, wherein the switching device is configured to electrically connect the electric storage device to the first inductor in order to enable electrical current to flow through the first branch and through the first inductor, caused by the electrical energy stored by means of the electric storage device, thereby causing the first inductor to generate the magnetic field, wherein the electrical current flowing through the first branch represents a first current direction of current flow between the electric storage device and the first inductor; and an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction; and wherein the connecting circuitry further comprises a second inductor connected in series with the first inductor, wherein:

the second inductor has a variable inductance; or the connecting circuitry further comprises bypass circuitry for selectively bypassing or short-circuiting the second inductor; or the second inductor has a variable inductance and the connecting circuitry further comprises bypass circuitry for bypassing or short-circuiting the second inductor;

so that electrical current flowing through the first inductor and through the connecting circuitry will also flow through the second inductor or the bypass circuitry, regardless of whether said electrical current flows through the first or the second branch.

In certain embodiments, the apparatus according to the fifth aspect can be constructed in a similar way to the circuit described in connection with FIG. 1. However, the addition of the second inductor in series with the first inductor constitutes a significant difference, not only in terms of the construction of the apparatus but also in terms of the operation of the apparatus, as will be explained below.

The explanations provided above in connection with the first aspect also apply in an analogous manner with respect to the fifth aspect, in particular regarding:

the electric storage device, together with the first inductor and the connecting circuitry, being able to be regarded as (similar to) a resonant circuit (or LC circuit)

the frequency $\omega_0$ of the resonant circuit being determined (approximately) by the values of the (applicable) inductance L and the capacitance C of the circuit, according to $$\omega_0 = \frac{1}{\sqrt{LC}}$$

whereby the applicable inductance includes, in particular, the inductance of the first and second inductor the types of inductors for use as the first inductor and/or the second inductor the types of switching devices and ways of operating these the terms “electrical connection” and “electrically connect”

the types of components that can be used as the electric (or electronic) component or as part of an assembly of electric (or electronic) components in the second branch.

Similarly, constructional and operational details of bypass circuitry for selectively bypassing or short-circuiting an inductor have already been provided above in connection with embodiments of the first aspect of the present disclosure. These details similarly apply to bypass circuitry of the fifth aspect.

Pursuant to embodiments of the present disclosure, while the first inductor is intended for generating a magnetic field for application to body tissue, the second inductor is not intended for this purpose. Of course, since a magnetic field is in principle able to have an infinite spread, any body tissue subjected to the magnetic field generated by the first inductor will also be subjected to the magnetic field generated by the second inductor. However, in embodiments of the present disclosure, the effects of this can be kept small, for example by placing the second inductor at a suitable distance from the first inductor (and thus from any body tissue to which the magnetic field generated by the first inductor is to be applied). Instead, the main purpose of the second inductor is to vary the frequency of the resonant circuit of which the first and second inductors form a part. In this way, the frequency of this resonant circuit can be varied even if the inductance of the first inductor cannot be varied. The change in the frequency can be used to influence the current through the first inductor, in particular at least one of the shape, duration or magnitude of a current pulse through the first inductor.

In one embodiment, an inductance of the second inductor is one of discretely variable and substantially continuously variable.

Constructional details of inductors of discretely variable or substantially continuously variable inductance have already been described above in relation to the first aspect of the present disclosure.

In one embodiment, the apparatus further comprises one or more further inductors connected in series with the second inductor.

The one or more further inductors are also connected in series with the first inductor. Their inductance also influences the frequency of the resonant circuit of which the first and second inductors (and the one or more further inductors) form a part.

As with the second inductor, the one or more further inductors are not intended for generating a magnetic field for application to body tissue, and the explanations provided above in connection with the second inductor apply similarly to the one or more further inductors.

In one embodiment, one or more of the one or more further inductors has a variable inductance.

The explanations provided above in connection with a variable inductance of the second inductor apply similarly to the one or more further inductors.

In one embodiment, the connecting circuitry further comprises further bypass circuitry for selectively bypassing or short-circuiting one or more of the one or more further inductors.

Constructional and operational details of bypass circuitry for selectively bypassing or short-circuiting an inductor have already been provided above in connection with embodiments of the first aspect of the present disclosure. These details similarly apply to further bypass circuitry for selectively bypassing or short-circuiting one or more further inductors of embodiments of the fifth aspect.

In one embodiment, the further bypass circuitry comprises individual circuit portions for selectively bypassing or short-circuiting one or more of the one or more further inductors individually.

With such individual circuit portions, one or more particular ones of the further inductors can be bypassed or short-circuited individually, whilst one or more other ones of the further inductors are not bypassed or short-circuited. In this manner, the total inductance of the circuit of which the first, second and further inductors form a part can assume various different values.

In one embodiment, one or more of the one or more further inductors has a variable inductance and/or is provided with further bypass circuitry for selectively bypassing or short-circuiting a respective one of the one or more further inductors.

In this manner, the total inductance of the circuit of which the first, second and further inductors form a part can be varied over a wide range.

In one embodiment, the inductances of the second inductor and of the one or more further inductors are chosen such that a total inductance of the connecting circuitry is one of:

discretely variable; and substantially continuously variable from a minimum value up to a maximum value, wherein the minimum value corresponds to a total inductance of the connecting circuitry when all those of the second and the further inductors which are provided with further bypass circuitry are bypassed or short-circuited and the inductances of all those of the second and the further inductors whose inductance is variable are adjusted to a minimum; and wherein the maximum value corresponds to a total inductance of the connecting circuitry when all those of the second and the further inductors which are provided with further bypass circuitry are not bypassed and not short-circuited and the inductances of all those of the second and the further inductors whose inductance is variable are adjusted to a maximum.

This enables the total inductance of the circuit and hence the frequency of the circuit to be varied over a particularly large range, and, through this, the current through the first inductor can also be varied accordingly. In particular, the shape, magnitude and/or duration of any current pulse through the first inductor can be varied over a correspondingly large range.

In one embodiment, the second inductor has a variable inductance with a maximum inductance of L2; the one or more further inductors have an inductance of value Lm, where m=3, 4, 5, . . . n+2 and n is the number of further capacitors; and Lm is substantially equal to $L2*2^{(m-3)}$.

In this embodiment, the ratio of L2:L3:Lm is substantially 1:1:2:4:8:16 etc. Through this choice of values, the total inductance of the connecting circuitry can be varied from its minimum value up to its maximum value with a relatively small total number of inductors. If at least one of the inductors, for example the second inductor, has an inductance which is substantially continuously variable, the total inductance of the connecting circuitry can also be varied substantially continuously from its minimum value up to its maximum value.

In one embodiment, the first inductor comprises at least one set of turns, preferably at least one set of generally circular, hexagonal or rectangular turns, wherein the turns of the at least one set of turns are preferably arranged such that each turn generates a contribution towards the magnetic field when the electrical current flows through the first inductor, wherein the contributions generated by each turn are superimposed in a positive manner, wherein the first inductor is disposed within a casing connected to a conduit through which extends at least one cable for supplying electrical power to the at least one set of turns, and wherein the second inductor is not disposed within said casing.

In this embodiment, similar to a corresponding embodiment of the first aspect, the first inductor may for example be disposed in a casing made of plastics material, which may be separate from, and separately movable with respect to, a unit such as a housing or cabinet accommodating the electric storage device, the switching device, the electric component or assembly of electric components, the first and second branch of the connecting circuitry and the second inductor (and, if provided, also the further inductors). The casing which houses the first inductor can be connected to the cabinet by the conduit accommodating the cable for supplying electrical power to the first inductor. An arrangement in which the first inductor and the casing which houses the first inductor is connected to other components of the apparatus by means of a conduit such that the first inductor can be moved relative to such other components can advantageously be used to bring the first inductor in proximity with body tissue without moving these other components (e.g. a cabinet which houses these other components and which may be much larger and heavier than the first inductor and the casing accommodating the first inductor).

In one embodiment, the electric storage device comprises a pulse capacitor which can be charged by a charging circuit.

The charging circuit may form part of the apparatus, or may be provided as a separate device for connection to the apparatus of the fifth aspect. The charging circuit may in particular comprise a voltage source and a switch to selectively connect the voltage source to the capacitor.

In a sixth aspect of the present disclosure, there is provided a method of generating a magnetic field, the method comprising:

providing an apparatus according to the fifth aspect;

storing electrical energy in the electric storage device;

switching the switching device so as to electrically connect the electric storage device to the first inductor and thereby enabling electrical current to flow through the first branch and the first inductor and the second inductor or the bypass circuitry, caused by the electrical energy stored by means of the electric storage device, thereby causing the first inductor to generate the magnetic field; and enabling electrical current to flow between the electric storage device and the first inductor through the second branch via said electric component or assembly of electric components and the second inductor or the bypass circuitry.

In one embodiment, the apparatus is operated in a pulsed manner, wherein the electrical current flowing through the first branch represents a first half pulse and wherein the electrical current flowing through the second branch represents a second half pulse, the first half pulse and the second half pulse together forming a pulse.

Assuming the inductances of the first and second branch are (at least approximately) the same, the duration and magnitude of the first and second half pulses will be (at least approximately) the same, although, as explained above, the magnitude of the second half pulse may be somewhat smaller than the magnitude of the first half pulse due to energy losses in the circuit. However, if the inductances of the first and second branches are not the same (in particular if they are substantially different), the duration and magnitude of the first half pulse will be (significantly) different from those of the second half pulse. This may be the case if an additional inductor is connected in series with either the switching device or the electric component or assembly of electric components in such a way that electrical current will flow through the additional inductor during the first half pulse but not during the second half pulse, or vice versa.

In one embodiment, the method further comprises selectively bypassing or short-circuiting the second inductor or varying the inductance of the second inductor, thereby selectively varying an inductance of the connecting circuitry.

The bypassing or short-circuiting of the second inductor, as well as the varying of the inductance of the second inductor has already been explained in connection with the fifth aspect.

In one embodiment, selectively bypassing or short-circuiting the second inductor or varying the inductance of the second inductor comprises selectively bypassing or short-circuiting the second inductor or varying the inductance of the second inductor at one of:

during the first half pulse,
during the second half pulse,
between the first half pulse and the second half pulse, and after the pulse.

Suitable (switching) circuitry can be used for actively bypassing or for short-circuiting the second inductor or for varying the inductance of the second inductor. Depending on when this bypassing, short-circuiting or varying takes place, different effects can be achieved: if done during the first half pulse, the frequency of the resonant circuit is changed during the first half pulse, and accordingly the duration of the first half pulse is changed part-way through the first half pulse. Similarly, if done during the second half pulse, the frequency of the resonant circuit is changed during the second half pulse, and accordingly the duration of the second half pulse is changed part-way through the second half pulse. In both cases, the signal (e.g. the current through the first inductor) changes its shape at the time when the second inductor is bypassed or short-circuited or its inductance is varied. That is, it does not continue to follow the same shape of the half pulse of the (approximated) sinewave that it followed initially, but instead continues along the shape of a different (approximated) sinewave (of a different pulse duration). If the second inductor is bypassed or short-circuited or its inductance is varied between the first half pulse and the second half pulse, the shape of each half pulse (approximately) resembles a half pulse of a sinewave. However, the duration and amplitude of the two half pulses will be different. The same applies, mutatis mutandis, if the second inductor is bypassed or short-circuited or its inductance is varied between one (full) pulse and the next (full) pulse.

A corresponding effect can be achieved by initially bypassing or short-circuiting the second inductor and interrupting the bypass or short-circuit either during the first half pulse, during the second half pulse, between the two half pulses or between one (full) pulse and the next (full) pulse.

In one embodiment, the method further comprises bringing the first inductor into proximity with body tissue, or bringing the body tissue into proximity with the first inductor, so that the magnetic field is present in said body tissue.

As with the third aspect, this may in particular be used for therapeutic purposes, but can also be used for non-therapeutic purposes.

Further explanations provided in connection with corresponding embodiments of the third aspect also apply to this embodiment of the sixth aspect.

In one embodiment, the method further comprises varying the magnetic field in the body tissue so as to generate a voltage in the body tissue or to cause a movement of charges in the body tissue.

As the magnetic field in the body tissue varies with the current through the first inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction in the body tissue, wherein preferably the voltage (or the movement of charges) is sufficient to cause a therapeutic effect.

A variety of effects can be achieved in a targeted manner using the apparatus of the fifth aspect or the method of the sixth aspect, in particular by suitable choice of the second inductor and, if applicable, bypassing or short-circuiting the second inductor or varying its inductance.

In a seventh aspect of the present disclosure, there is provided an apparatus for use with a first inductor for generating a magnetic field for application to body tissue, the apparatus comprising:

an electric storage device for storing electrical energy;

a terminal for connection to the first inductor for generating a magnetic field for application to body tissue;

connecting circuitry between the electric storage device and said terminal, wherein the connecting circuitry comprises at least a first branch and a second branch;

a switching device, wherein the switching device forms part of the first branch, wherein the switching device is configured to electrically connect the electric storage device to said terminal so as to enable electrical current to flow through the first branch and through the first inductor via said terminal when the first inductor is connected to the apparatus via said terminal, caused by the electrical energy stored by means of the electric storage device, thereby causing the first inductor to generate the magnetic field, wherein the electrical current flowing through the first branch represents a first current direction of current flow between the electric storage device and said terminal;

an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch via said terminal when the first inductor is connected to the apparatus via said terminal, wherein the current flow in the forward direction represents a second current direction of current flow between the electric storage device and the first inductor, the second current direction being opposite the first current direction; and wherein the connecting circuitry further comprises a second inductor connected in series with the first inductor, wherein:

the second inductor has a variable inductance; or the connecting circuitry further comprises bypass circuitry for selectively bypassing or short-circuiting the second inductor; or the second inductor has a variable inductance and the connecting circuitry further comprises bypass circuitry for bypassing or short-circuiting the second inductor;

so that electrical current flowing through the first inductor and through the connecting circuitry will also flow through the second inductor or the bypass circuitry, regardless of whether said electrical current flows through the first or the second branch.

The apparatus of the seventh aspect is similar to the apparatus of the fifth aspect. However, in contrast to the fifth aspect, the first inductor mentioned in connection with the seventh aspect does not form part of the apparatus of the seventh aspect. Instead, the apparatus of the seventh aspect has a terminal (such as an electric socket or similar) for connection to the first inductor. Accordingly, a number of (different) inductors, for example inductors having different shapes, inductances or other characteristics, can selectively be connected to the apparatus of the seventh aspect and used as the first inductor.

In an eighth aspect of the present disclosure, there is provided an apparatus for generating a magnetic field for application to body tissue, the apparatus comprising:

a capacitor arrangement comprising at least one capacitor for storing electrical energy;

an inductor for generating a magnetic field for application to body tissue;

connecting circuitry between the capacitor arrangement and the inductor, wherein the connecting circuitry comprises at least a first branch and a second branch;

a first switching device, wherein the first switching device forms part of the first branch, wherein the first switching device is configured to electrically connect the capacitor arrangement to the inductor in order to enable electrical current to flow through the first branch and through the inductor, caused by the electrical energy stored by means of the capacitor arrangement, thereby causing the inductor to generate the magnetic field, wherein the electrical current flowing through the first branch represents a first current direction of current flow between the capacitor arrangement and the inductor; and an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the capacitor arrangement and the inductor through the second branch, wherein the current flow in the forward direction represents a second current direction of current flow between the capacitor arrangement and the inductor, the second current direction being opposite the first current direction;

wherein the capacitor has a variable capacitance.

In certain embodiments, the apparatus according to the eighth aspect can be constructed in a similar way to the circuit described in connection with FIG. 1. However, the use of a capacitor with a variable capacitance constitutes a significant difference, not only in terms of the construction of the apparatus but also in terms of the operation of the apparatus, as will be explained below.

The explanations provided above in connection with the first and fifth aspects also apply in an analogous manner with respect to the eighth aspect, in particular regarding:

the capacitor arrangement (comprising at least one capacitor) of the eighth aspect, which is a form of electric storage device (first and fifth aspect), together with the inductor and the connecting circuitry, being able to be regarded as (similar to) a resonant circuit (or LC circuit)

the frequency $\omega_0$ of the resonant circuit being determined (approximately) by the values of the (applicable) inductance L and the capacitance C of the circuit, according to $$\omega_0 = \frac{1}{\sqrt{LC}}$$

whereby the applicable inductance includes, in particular, the inductance of the first (and any second or further) inductor the types of inductors for use as the inductor the types of switching devices and ways of operating these the terms "electrical connection" and "electrically connect"

the types of components that can be used as the electric (or electronic) component or as part of an assembly of electric (or electronic) components in the second branch.

In principle, any type of variable capacitor (or capacitor which has a variable capacitance) may be used as the capacitor of the eighth aspect, including mechanically controlled variable capacitors and electrically controlled variable capacitors. The capacitance of the at least one capacitor influences the frequency of the resonant circuit of which the capacitor forms a part, i.e. by varying the capacitance of the at least one capacitor, the frequency of the resonant circuit is also varied, as described above.

In certain embodiments, the capacitance of the at least one capacitor is (substantially) continuously variable. In this way, the frequency of the resonant circuit is also (substantially) continuously variable. Alternatively, the capacitance of the at least one capacitor is discretely variable, preferably however in small steps. In this way, the frequency of the resonant circuit may be almost continuously variable.

In one embodiment, the capacitor arrangement comprises one or more further capacitors connected in parallel to said capacitor. Their capacitance influences the frequency of the resonant circuit of which the capacitor and the one or more further capacitors form a part.

In one embodiment, at least one of the one or more further capacitors, in particular all of the further capacitors, have a capacitance which is one of:

variable;

discretely variable; and substantially continuously variable.

This also helps to ensure that the frequency of the resonant circuit of which the capacitor and the one or more further capacitors form a part can be adjusted. The greater the adjustable range of the capacitance of the capacitor and the one or more further capacitors is, the greater the adjustable range of the frequency of the resonant circuit becomes, thereby increasing the flexibility in terms of the magnetic field to be generated by the apparatus, such as pulse duration, amplitude and/or shape of a pulse.

In one embodiment, the capacitance of the first capacitor and the capacitances of the one or more further capacitors are chosen such that a total capacitance of the capacitor arrangement is one of:

discretely variable; and
substantially continuously variable
from a minimum value up to a maximum value,
wherein the minimum value corresponds to a total capacitance of the capacitor arrangement when the capacitance of the first capacitor and the capacitances of the one or more further capacitors is adjusted to a minimum; and
wherein the maximum value corresponds to a total capacitance of the capacitor arrangement when the capacitance of the first capacitor and the capacitances of the one or more further capacitors is adjusted to a maximum.

Since the capacitor and the one or more further capacitors are connected in parallel, their capacitances are added to result in the total capacitance of the resonant circuit of which the capacitor and the one or more further capacitors form a part (again assuming ideal components). In particular if the capacitances of all of the first capacitor and the one or more further capacitors are (substantially) continuously variable, the total capacitance will also be (substantially) continuously variable from the minimum value to the maximum value mentioned above. But even if the capacitance of only one capacitor is (substantially) continuously variable and the capacitance of any further capacitor(s) is only discretely variable, the total capacitance may still be (substantially) continuously variable from the minimum value to the maximum value mentioned above. This will in particular be the case if the discrete steps by which the capacitance of any such further capacitor(s) is variable is no greater than the range over which the capacitance of the (first) capacitor is (substantially) continuously variable. An example: Let's assume the capacitance of the first capacitor can be adjusted (substantially) continuously between 0 μF and 100 μF and the capacitance of one further capacitor can be adjusted in discrete steps to assume only two values: 0 μF and 100 μF. In this case, when the further capacitor is adjusted to 0 μF, by varying the capacitance of the first capacitor the total capacitance of the capacitor arrangement can be adjusted (substantially) continuously between 0 μF and 100 μF. When the further capacitor is adjusted to 100 μF, by varying the capacitance of the first capacitor the total capacitance of the capacitor arrangement can be adjusted (substantially) continuously between 100 μF and 200 μF. Therefore, the total capacitance of the capacitor arrangement can be adjusted (substantially) continuously between 0 μF and 200 μF. Similarly, in another example, if the further capacitor can be adjusted in discrete steps to assume the values 200 μF, 300 μF and 400 μF, and the capacitance of the first capacitor can be adjusted (substantially) continuously between 0 μF and 100 μF, then the total capacitance of the capacitor arrangement can be adjusted (substantially) continuously between 200 μF and 500 μF.

In one embodiment, the apparatus further comprises one or more further switching devices, one for each of the one or more further capacitors, wherein the one or more further switching devices are configured to selectively interrupt an electrical connection between a respective one of the one or more further capacitors and the connecting circuitry.

In this manner, the total capacitance of the circuit of which the first capacitor and the one or more further capacitors form a part can assume various different values.

It is also possible to provide some of the further capacitors with a respective further switching device and to provide other ones of the further capacitors as capacitors with a variable capacitance, in which case the total capacitance of the circuit can also assume various different values and can in particular be adjustable, in particular (substantially) continuously, over a selected range.

In one embodiment, the capacitance of the first capacitor and the capacitances of the one or more further capacitors are chosen such that a total capacitance of the capacitor arrangement is one of:
discretely variable; and
substantially continuously variable
from a minimum value up to a maximum value,
wherein the minimum value corresponds to a total capacitance of the capacitor arrangement when:
the electrical connection between the one or more further capacitors and the connecting circuitry is interrupted by the further switching devices; and
the capacitance of the first capacitor is adjusted to a minimum
and
wherein the maximum value corresponds to a total capacitance of the capacitor arrangement when:
the electrical connection between the one or more further capacitors and the connecting circuitry is not interrupted; and
the capacitance of the first capacitor is adjusted to a maximum.

The comments above regarding adjustability of the total capacitance of the capacitor arrangement also apply to this embodiment, mutatis mutandis.

In one embodiment, the apparatus further comprises a charging circuit for charging the capacitor arrangement.

The charging circuit may in particular comprise a voltage source and a switch to selectively connect the voltage source to the capacitor arrangement.

In alternative embodiments, the charging circuit may be provided as a separate device for connection to the apparatus of the eighth aspect, i.e. may not form part of the apparatus of the eighth aspect.

In one embodiment:
the first capacitor has a maximum capacitance of value C1
the n further capacitors have a capacitance of value Cm, where n is the number of further capacitors and m=2, 3, 4, . . . n+1
Cm is substantially equal to $C1*2^{(m-2)}$.

In this embodiment, the ratio of C1:C2:Cm is substantially 1:1:2:4:8:16 etc. Through this choice of values, the total capacitance of the capacitor arrangement can be varied from its minimum value up to its maximum value over a relatively wide range with a relatively small total number of capacitors. If at least one of the capacitors, for example the first capacitor, has a capacitance which is (substantially) continuously variable, the total capacitance of the capacitor arrangement can also be varied (substantially) continuously from its minimum value up to its maximum value.

In a ninth aspect of the present disclosure, there is provided a method of generating a magnetic field, the method comprising:
providing an apparatus according to the eighth aspect;
storing electrical energy in the capacitor arrangement;
switching the first switching device so as to electrically connect the capacitor arrangement to the inductor and thereby enabling electrical current to flow through the first branch and through the inductor, caused by the electrical energy stored by means of the capacitor arrangement, thereby causing the inductor to generate the magnetic field; and enabling electrical current to flow between the capacitor arrangement and the inductor through the second branch via said electric component or assembly of electric components.

In one embodiment, the apparatus is operated in a pulsed manner, wherein the electrical current flowing through the first branch represents a first half pulse and wherein the electrical current flowing through the second branch represents a second half pulse.

As mentioned above, the pulses, in particular their duration, amplitude and/or shape can be influenced by varying the capacitance of the capacitor arrangement.

In one embodiment, the method further comprises varying a total capacitance of the capacitor arrangement at a point in time which is one of:

during the first half pulse, during the second half pulse, between the first half pulse and the second half pulse, and between the second half pulse and a subsequent pulse.

Suitable arrangements for varying the total capacitance of the capacitor arrangement have already been described above, and include in particular the varying of the capacitance of an individual capacitor of the capacitor arrangement and/or using one or more further switching devices for respective ones of the one or more further capacitors to selectively establish or interrupt an electrical connection between a respective one of the one or more further capacitors and the connecting circuitry.

Depending on when the varying of the total capacitance of the capacitor arrangement takes place, different effects can be achieved: if done during the first half pulse, the frequency of the resonant circuit is changed during the first half pulse, and accordingly the duration of the first half pulse is changed part-way through the first half pulse. Similarly, if done during the second half pulse, the frequency of the resonant circuit is changed during the second half pulse, and accordingly the duration of the second half pulse is changed part-way through the second half pulse. In both cases, the signal (e.g. the current through the inductor) changes its shape at the time when the total capacitance of the capacitor arrangement is varied. That is, the signal does not continue to follow the same shape of the half pulse of the (approximated) sinewave that it followed initially, but instead continues along the shape of a different (approximated) sinewave (of a different pulse duration). If the varying of the total capacitance of the capacitor arrangement takes place between the first half pulse and the second half pulse, the shape of each half pulse (approximately) resembles a half pulse of a sinewave. However, the duration and amplitude of the two half pulses will be different. The same applies, mutatis mutandis, if the varying of the total capacitance of the capacitor arrangement takes place between one (full) pulse and the next (full) pulse.

In one embodiment, the total capacitance of the capacitor arrangement is varied such that a duration of the second half pulse is longer than a duration of the first half pulse. This can be achieved by increasing the total capacitance of the capacitor arrangement between the first and second half pulses, or at any time after the start of the first half pulse and before the end of the second half pulse.

Different effects can be achieved depending on whether the total capacitance of the capacitor arrangement is increased or reduced. It can be increased by increasing the capacitance of an individual capacitor of the capacitor arrangement, or by operating one or more further switching devices so as to establish an electrical connection between a respective one of the one or more further capacitors and the connecting circuitry. Conversely, it can be reduced by reducing the capacitance of an individual capacitor of the capacitor arrangement, or by operating one or more further switching devices so as to interrupt an electrical connection between a respective one of the one or more further capacitors and the connecting circuitry. Increasing the total capacitance of the capacitor arrangement will result in a longer pulse duration. Reducing the total capacitance of the capacitor arrangement will result in a shorter pulse duration.

In one embodiment, the method further comprises bringing the inductor into proximity with body tissue so as to generate the magnetic field in said body tissue, or bringing the body tissue into proximity with the inductor, so that the magnetic field is present in said body tissue.

This may in particular be used for therapeutic purposes, but can also be used for non-therapeutic purposes.

As the total capacitance of the capacitor arrangement influences the frequency of the resonant circuit and the magnitude of the current through the inductor, this total capacitance also has an influence on the magnetic field generated by the inductor, which can be used to achieve particular effects in the body tissue.

According to this embodiment, bringing the inductor into proximity with body tissue can for example be accomplished by moving the inductor, sometimes also called applicator coil, towards body tissue, or by moving it along the body surface of a person or animal. An example of bringing the body tissue into proximity with the inductor can involve the use of the inductor in a (temporarily) fixed position, and a person or animal approaching the inductor. Such an inductor in a fixed position may for example be attached to, or integrated into, a chair or similar.

Also, it is possible first to bring the inductor into proximity with body tissue (or to bring the body tissue into proximity with the inductor) and then to generate the magnetic field, or vice versa.

The distance between the inductor and the body tissue may for example be a few millimeters or centimeters, although larger distances (such as several tens of centimeters) may also be considered.

In one embodiment, the method further comprises varying the magnetic field in the body tissue so as to generate a voltage in the body tissue or to cause a movement of charges in the body tissue.

As the magnetic field in the body tissue varies with the current through the inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction in the body tissue, wherein preferably the voltage (or the movement of charges) is sufficient to cause a therapeutic effect.

A variety of effects can be achieved in a targeted manner using the apparatus of the eighth aspect or the method of the ninth aspect, in particular by suitable choice of the total capacitance of the capacitor arrangement, in particular by suitable choice of the capacitance of individual capacitors of the capacitor arrangement and/or, if applicable, operating one or more further switching devices so as to establish or interrupt an electrical connection between a respective one of the one or more further capacitors and the connecting circuitry.

In a tenth aspect of the present disclosure, there is provided an apparatus for use with an inductor for generating a magnetic field for application to body tissue, the apparatus comprising:

a capacitor arrangement comprising at least one capacitor for storing electrical energy;

a terminal for connection to the inductor for generating a magnetic field for application to body tissue;

connecting circuitry between the capacitor arrangement and said terminal, wherein the connecting circuitry comprises at least a first branch and a second branch;

a switching device, wherein the switching device forms part of the first branch, wherein the switching device is configured to electrically connect the capacitor arrangement to said terminal so as to enable electrical current to flow through the first branch and through the inductor via said terminal when the inductor is connected to the apparatus via said terminal, caused by the electrical energy stored by means of the capacitor arrangement, thereby causing the inductor to generate the magnetic field, wherein the electrical current flowing through the first branch represents a first current direction of current flow between the capacitor arrangement and said terminal; and an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the capacitor arrangement and the inductor through the second branch via said terminal when the inductor is connected to the apparatus via said terminal, wherein the current flow in the forward direction represents a second current direction of current flow between the capacitor arrangement and the inductor, the second current direction being opposite the first current direction;

wherein the capacitor has a variable capacitance.

The apparatus of the tenth aspect is similar to the apparatus of the eighth aspect. However, in contrast to the eighth aspect, the inductor mentioned in connection with the eighth aspect does not form part of the apparatus of the tenth aspect. Instead, the apparatus of the tenth aspect has a terminal (such as an electric socket or similar) for connection to the inductor. Accordingly, a number of (different) inductors, for example inductors having different shapes, inductances or other characteristics, can selectively be connected to the apparatus of the tenth aspect and used as the inductor.

In an eleventh aspect, which is an aspect of the present disclosure, there is provided an apparatus for generating a magnetic field for application to body tissue, the apparatus comprising:

a capacitor arrangement comprising at least one capacitor for storing electrical energy;

an inductor for generating a magnetic field for application to body tissue;

connecting circuitry between the capacitor arrangement and the inductor, wherein the connecting circuitry comprises at least a first branch and a second branch;

a switching device, wherein the switching device forms part of the first branch, wherein the switching device is configured to be changed from a substantially non-conductive state to a conductive state at a first point in time in order to form a first electrical connection between the capacitor arrangement and the inductor in order to enable electrical current to flow through the first branch and through the inductor, caused by the electrical energy stored by means of the capacitor arrangement, thereby causing the inductor to generate the magnetic field, wherein the switching device is configured to be changed from the conductive state to the substantially non-conductive state at a second point in time in order to interrupt said first electrical connection between the capacitor arrangement and the inductor;

at least one electrical circuit element, wherein the electrical circuit element forms part of the second branch, wherein the electrical circuit element is configured to be changed from a substantially non-conductive state to a conductive state in order to form a second electrical connection between the capacitor arrangement and the inductor in order to enable electrical current to flow through the second branch and through the inductor;

wherein the first and second points in time can be freely chosen.

In certain embodiments, the apparatus according to the eleventh aspect can be constructed in a similar way to the circuit described in connection with FIG. 1. However, the construction of the apparatus in such a way that the switching device can be changed from the substantially non-conductive state to the conductive state and back to the substantially non-conductive state, respectively at first and second points in time which can be freely chosen, constitutes a significant difference, not only in terms of the construction of the apparatus but also in terms of the operation of the apparatus, as will be explained below.

The explanations provided above in connection with the first, fifth and eighth aspects also apply in an analogous manner to the eleventh aspect, in particular regarding:

the capacitor arrangement (comprising at least one capacitor) of the eleventh aspect, which is a form of electric storage device (first and fifth aspects), together with the inductor and the connecting circuitry, being able to be regarded as (similar to) a resonant circuit (or LC circuit)

the capacitor arrangement of the eleventh aspect being able to be constructed in a similar way to the capacitor arrangement of the eighth aspect the frequency $\omega_0$ of the resonant circuit being determined (approximately) by the values of the (applicable) inductance L and the capacitance C of the circuit, according to $$\omega_0 = \frac{1}{\sqrt{LC}}$$

whereby the applicable inductance includes, in particular, the inductance of the (first and any second or further) inductor the types of inductors for use as the inductor the types of switching devices and ways of operating these, subject to further details explained below the terms “electrical connection” and “electrically connect”.

Pursuant to the eleventh aspect, the term “freely chosen” does not necessarily mean that there are no restrictions at all, but at least there is a significant (temporal) range in which the first and second points in time can be chosen, in particular by a user of the apparatus. In particular, there is no need for the second point in time to be at a specific, fixed time delay after the first point in time, such as—assuming that the apparatus is operated in a pulsed manner—after, or at the end of, a first half pulse. Instead, the second point in time can be chosen independently from the first point in time.

In a typical embodiment envisaged by the inventor, a user would pre-select the first and second points in time, either as specific (or absolute) points in time or relative to another event. In particular, a user may select the second point in time as a point in time after a selected time interval has elapsed since the first point in time. To this end, the apparatus may have a suitable interface, such as a dial or touchscreen, via which the user can specify the selected time interval.

In one embodiment, the apparatus further comprises a first controller for causing the switching device to change from the substantially non-conductive state to the conductive state at the first point in time and/or for causing the switching device to change from the conductive state to the substantially non-conductive state at the second point in time. The first controller may, for example, receive suitable inputs from a user, for example, via the interface mentioned above. The first controller may, for example, comprise a microcontroller. Alternatively, the first controller may be provided in the form of analog circuitry, for example circuitry connecting the interface mentioned above (e.g. a dial) with the switching device.

In one embodiment, the at least one electrical circuit element is configured to be changed from the conductive state to the substantially non-conductive state in order to interrupt said second electrical connection between the electric storage device and the inductor.

In one embodiment, the apparatus further comprises a second controller for causing the at least one electrical circuit element to change from the substantially non-conductive state to the conductive state at a third point in time and/or for causing the at least one electrical circuit element to change from the conductive state to the substantially non-conductive state at a fourth point in time. The second controller may, for example, receive suitable inputs from a user, for example, via an interface such as the one mentioned above. The second controller may, for example, comprise a microcontroller. Alternatively, the second controller may be provided in the form of analog circuitry, for example circuitry connecting the interface mentioned above (e.g. a dial) with the at least one electrical circuit element. The second controller may be identical to the first controller, in the sense that there is only one controller controlling both the switching device and the at least one electrical circuit element. Alternatively, the first and second controllers may be provided as separate units.

In one embodiment, the switching device comprises an insulated-gate bipolar transistor (IGBT), a field-effect transistor (FET), a metal-oxide-semiconductor field-effect transistor (MOSFET) or a gate turn-off thyristor (GTO-thyristor). Any other suitable switching device, in particular one that can be switched off at a desired point in time, may be used instead.

In one embodiment, the at least one electrical circuit element comprises a passive electrical circuit element, in particular:

a spark gap
a transient-voltage-suppression diode
a Zener diode
a Shockley diode
or
a triode for alternating current (TRIAC) or
a thyristor, in particular in combination with trigger circuitry connected to, or forming part of, the second branch to trigger the thyristor.

In the case of a spark gap, the following regime for the (absolute values of the) voltages involved is preferably adhered to: The capacitor arrangement is, or can be, or is arranged to be, charged up to a voltage U1. The spark gap is rated to, i.e. becomes conductive at, a voltage U2. The switching device suffers (significant) damage, or is destroyed, at or above a voltage U3, wherein: U1<U2<U3. Adhering to this regime may ensure that the spark gap does not already become conductive as the capacitor arrangement is being charged. At the same time, it may ensure that the switching device (of the first branch) is not damaged or destroyed since the voltage that is arranged to cause the spark gap to become conductive may also be applied to the switching device (in reverse bias).

In one embodiment, the at least one electrical circuit element comprises an active electrical circuit element or an arrangement of circuit elements, in particular a switching element controlled by analog circuitry or a microcontroller. This enables the user to actively control the electrical circuit element, rather than the electrical circuit element simply being allowed to become conductive or non-conductive depending on the voltage applied to its two terminals within the second branch.

A resistor may also be provided in the second branch.

In one embodiment, the at least one electrical circuit element is configured to be changed from the substantially non-conductive state to the conductive state at a third point in time, wherein the third point in time coincides with the second point in time or is after the second point in time, in particular a predetermined or predeterminable time interval after the second point in time. Again, a user may specify the third point in time, for example via the interface mentioned above, and may in particular specify the time interval between the second point in time and the third point in time. Alternatively, the third point in time may be fixed, or the interval between the second point in time and the third point in time may be fixed.

In a twelfth aspect, which is an aspect of the present disclosure, there is provided a method of generating a magnetic field, the method comprising:

providing an apparatus according to the eleventh aspect;

storing electrical energy in the capacitor arrangement;

switching the switching device from the substantially non-conductive state to the conductive state at the first point in time so as to form said first electrical connection between the capacitor arrangement and the inductor and thereby enabling electrical current to flow through the first branch and through the inductor, caused by the electrical energy stored by means of the capacitor arrangement, thereby causing the inductor to generate the magnetic field;

switching the switching device from the conductive state to the substantially non-conductive state at the second point in time and thereby interrupting said first electrical connection between the capacitor arrangement and the inductor; and causing the at least one electrical circuit element to change from the substantially non-conductive state to the conductive state, thereby enabling electrical current to flow between the capacitor arrangement and the inductor through the second branch via said at least one electrical circuit element.

Embodiments described in connection with the eleventh aspect similarly apply to the twelfth aspect, and vice versa.

In one embodiment, switching the switching device from the substantially non-conductive state to the conductive state at the first point in time triggers an oscillation of current flow between the capacitor arrangement and the inductor, wherein the second point in time is chosen not to coincide with a transition between a first half wave and a second half wave of said oscillation. In this way, the oscillation can be aborted at a selected point in time, in order to achieve a particular effect.

In one embodiment, the second point in time is chosen to be during the first half wave of said oscillation, preferably during a first quarter wave of said oscillation.

In one embodiment, the method further comprises bringing the inductor into proximity with body tissue, or bringing the body tissue into proximity with the inductor, so that the magnetic field is present in said body tissue. This may in particular be used for therapeutic purposes, but can also be used for non-therapeutic purposes.

Bringing the inductor into proximity with body tissue can for example be accomplished by moving the inductor, sometimes also called applicator coil, towards body tissue, or by moving it along the body surface of a person or animal. An example of bringing the body tissue into proximity with the inductor can involve the use of the inductor in a (temporarily) fixed position, and a person or animal approaching the inductor. Such an inductor in a fixed position may for example be attached to, or integrated into, a chair or similar.

Also, it is possible first to bring the inductor into proximity with body tissue (or to bring the body tissue into proximity with the inductor) and then to generate the magnetic field, or vice versa.

The distance between the inductor and the body tissue may for example be a few millimeters or centimeters, although larger distances (such as several tens of centimeters) may also be considered.

In one embodiment, the method further comprises varying the magnetic field in the body tissue so as to generate a voltage in the body tissue or to cause a movement of charges in the body tissue. As the magnetic field in the body tissue varies with the current through the inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction in the body tissue, wherein preferably the voltage (or the movement of charges) is sufficient to cause a therapeutic effect.

A variety of effects can be achieved in a targeted manner using the apparatus of the eleventh aspect or the method of the twelfth aspect, in particular by suitable choice of the first and/or second points in time, in particular the time interval between the first and second points in time.

In one embodiment, the method further comprises bringing the inductor into proximity with body tissue so as to generate the magnetic field in said body tissue, wherein a duration between the first point in time and the second point in time defines a time interval, wherein the method further comprises, one or more times, carrying out the following steps:

varying the time interval;

switching the switching device from the substantially non-conductive state to the conductive state; and after the varied time interval, switching the switching device from the conductive state to the substantially non-conductive state.

By varying the time interval and switching the switching device from the conductive state to the substantially non-conductive state after the varied time interval, the oscillation is aborted at various times based on the varied time interval. Various measurements can be carried out, in particular measurements regarding any reaction in the body tissue, and recorded and/or analyzed, in particular as a function of the varied time interval.

In one embodiment, the method further comprises detecting whether a muscle reaction in the body tissue has been caused, in order to provide a detection result; and based on the detection result, determining a minimum duration, corresponding to the time interval or the varied time interval, at which the muscle reaction in the body tissue is caused.

In a thirteenth aspect, which is an aspect of the present disclosure, there is provided an apparatus for use with an inductor for generating a magnetic field for application to body tissue, the apparatus comprising:

a capacitor arrangement comprising at least one capacitor for storing electrical energy;

a terminal for connection to the inductor for generating a magnetic field for application to body tissue;

connecting circuitry between the capacitor arrangement and said terminal, wherein the connecting circuitry comprises at least a first branch and a second branch;

a switching device, wherein the switching device forms part of the first branch, wherein the switching device is configured to be changed from a substantially non-conductive state to a conductive state at a first point in time in order to form a first electrical connection between the capacitor arrangement and said terminal so as to enable electrical current to flow through the first branch and through the inductor via said terminal when the inductor is connected to the apparatus via said terminal, caused by the electrical energy stored by means of the capacitor arrangement, thereby causing the inductor to generate the magnetic field, wherein the switching device is configured to be changed from the conductive state to the substantially non-conductive state at a second point in time in order to interrupt said first electrical connection between the capacitor arrangement and said terminal;

at least one electrical circuit element, wherein the electrical circuit element forms part of the second branch, wherein the electrical circuit element is configured to be changed from a substantially non-conductive state to a conductive state in order to form a second electrical connection between the capacitor arrangement and said terminal so as to enable electrical current to flow through the second branch and through the inductor via said terminal when the inductor is connected to the apparatus via said terminal;

wherein the first and second points in time can be freely chosen.

The apparatus of the thirteenth aspect is similar to the apparatus of the eleventh aspect. However, in contrast to the eleventh aspect, the inductor mentioned in connection with the thirteenth aspect does not form part of the apparatus of the thirteenth aspect. Instead, the apparatus of the thirteenth aspect has a terminal (such as an electric socket or similar) for connection to the inductor. Accordingly, a number of (different) inductors, for example inductors having different shapes, inductances or other characteristics, can selectively be connected to the apparatus of the thirteenth aspect and used as the inductor.

In any of the eleventh to thirteenth aspects or their embodiments, the first and second points in time (or the time interval between these) can also be predetermined, i.e. chosen by a user or manufacturer in advance, and stored in a memory device of the apparatus or predetermined by the electrical design (analog circuitry design) of the apparatus—but again such that the first and second points in time do not coincide with the end of a first half pulse (again assuming that the apparatus is operated in a pulsed manner). When the apparatus of the eleventh or thirteenth aspect is used or the method according to the twelfth aspect is executed, information regarding the first and/or second points in time, or the time interval between these, can be retrieved (e.g. from the memory device) and the apparatus controlled accordingly. In embodiments in which the first and second points in time (or the time interval between these) are predetermined by the electrical design (analog circuitry design) of the apparatus, using the apparatus of the eleventh or thirteenth aspect or executing the method according to the twelfth aspect will also result in the corresponding time interval between the first and second points in time.

In a fourteenth aspect, which is an aspect of the present invention, there is provided an apparatus for generating a magnetic field for application to body tissue, the apparatus comprising:

an electric storage device for storing electrical energy;

a first inductor for generating a first magnetic field for application to body tissue;

a second inductor for generating a second magnetic field;

connecting circuitry between the electric storage device and the first and second inductors, wherein the connecting circuitry comprises a first branch between the electric storage device and the first inductor and a second branch between the electric storage device and the second inductor;

a first switching device, wherein the first switching device forms part of the first branch, wherein the first switching device is configured to electrically connect the electric storage device to the first inductor in order to enable electrical current to flow through the first branch and through the first inductor, caused by the electrical energy stored by means of the electric storage device, thereby causing the first inductor to generate the first magnetic field, wherein the electrical current flowing through the first branch represents a first current direction of current flow with respect to the electric storage device; and a second switching device, wherein the second switching device forms part of the second branch, wherein the second switching device is configured to electrically connect the electric storage device to the second inductor in order to enable electrical current to flow through the second branch and through the second inductor, caused by the electrical energy stored by means of the electric storage device, thereby causing the second inductor to generate the second magnetic field, wherein the electrical current flowing through the second branch represents a second current direction of current flow with respect to the electric storage device, wherein the second current direction of current flow is opposite the first current direction of current flow.

In certain embodiments, the apparatus according to the fourteenth aspect can be constructed in a similar way to the circuit described in connection with FIG. 1. However, a) providing the second inductor, b) providing the first branch between the electric storage device and the first inductor, and providing the second branch between the electric storage device and the second inductor, c) providing the first and second switching devices, and d) with respect to the electric storage device, the second current direction of current flow through the second branch being opposite the first current direction of current flow through the first branch constitutes a significant difference, not only in terms of the construction of the apparatus but also in terms of the operation of the apparatus, as will be explained below.

The explanations provided above in connection with the first, fifth, eighth and eleventh aspects also apply in an analogous manner to the fourteenth aspect, in particular regarding:

the electric storage device, together with the first inductor and the connecting circuitry, being able to be regarded as (similar to) a resonant circuit (or LC circuit)

the electric storage device, together with the second inductor and the connecting circuitry, being able to be regarded as (similar to) a resonant circuit (or LC circuit)

the frequency $\omega_0$ of the resonant circuit(s) being determined (approximately) by the values of the (applicable) inductance L and the capacitance C of the circuit, according to $$\omega_0 = \frac{1}{\sqrt{LC}}$$

whereby the applicable inductance includes, in particular, the inductance of the first or the second inductor the types of inductors for use as the first inductor and/or the second inductor the types of switching devices (for use as the first and second switching devices) and ways of operating these the terms "electrical connection" and "electrically connect".

The circuit according to the fourteenth aspect enables the first and second inductors to be used in a variety of manners, in particular substantially independently from one another, or in cooperation. Nevertheless, in principle it is possible to operate the circuit according to the fourteenth aspect with only one electric storage device, such as a capacitor, although it is equally possible to provide a capacitor arrangement comprising several capacitors as the electric storage device. In any event, it is not necessary to provide a separate electric storage device for each inductor.

The first inductor may for example be accommodated in a first casing which can be moved by an operator and placed upon a body part of a person or animal.

In one embodiment, the first and second inductors are not connected in series. That means, in particular, that electrical current through the first inductor does not flow through the second inductor, and vice versa. The first and second branches can therefore be regarded as substantially independent from one another, except that both are connected to the electric storage device.

In one embodiment, the first switching device is configured to enable current flow with respect to the electric storage device only in the first current direction; and the second switching device is configured to enable current flow with respect to the electric storage device only in the second current direction. Suitable switching devices include, without limitation, thyristors, gate turn-off thyristors (GTO-thyristors), IGBTs and FETs.

In one embodiment, the second inductor is configured such that the second magnetic field is also for application to body tissue. For example, the second inductor may be accommodated in a second casing which can be moved by an operator and placed upon a body part of a person or animal.

According to a variant, the second magnetic field to be generated by the second inductor is not necessarily intended to be for application to body tissue. Of course, since a magnetic field is in principle able to have an infinite spread, any body tissue subjected to the magnetic field generated by the first inductor will also be subjected to the second magnetic field generated by the second inductor. However, in such a variant, the effects of this can be kept small, for example by placing the second inductor at a suitable distance from the first inductor (and thus from any body tissue to which the first magnetic field generated by the first inductor is to be applied). The second inductor may, for example, be accommodated within a metal housing, in particular a metal housing which also accommodates other parts of the circuit of the fourteenth aspect, such as the electric storage device.

In one embodiment, the first inductor comprises at least a first set of turns, preferably at least a first set of generally circular, hexagonal or rectangular turns, wherein the turns of the first set of turns are preferably arranged such that each turn generates a contribution towards the first magnetic field when the electrical current flows through the first inductor, wherein the contributions generated by each turn are superimposed in a positive manner, wherein the first inductor is disposed within a first casing connected to a first conduit through which extends at least a first cable for supplying electrical power to the first set of turns, and wherein the second inductor is not disposed within said first casing.

According to this embodiment, the first inductor may for example be disposed in a casing made of plastics material, which may be separate from, and separately movable with respect to, a unit such as a housing or cabinet accommodating the electric storage device, the first and second switching devices and at least a portion of each of the first and second branches of the connecting circuitry. The casing which houses the first inductor can be connected to the cabinet by the conduit accommodating the cable for supplying electrical power to the first inductor. An arrangement in which the first inductor and the casing which houses the first inductor is connected to other components of the apparatus by means of a conduit such that the first inductor can be moved relative to such other components can advantageously be used to bring the first inductor in proximity with body tissue without moving these other components (e.g. a cabinet which houses these other components and which may be much larger and heavier than the first inductor and the casing accommodating the first inductor).

In one embodiment, the second inductor comprises at least a second set of turns, preferably at least a second set of generally circular, hexagonal or rectangular turns, wherein the turns of the second set of turns are preferably arranged such that each turn generates a contribution towards the second magnetic field when the electrical current flows through the second inductor, wherein the contributions generated by each turn are superimposed in a positive manner, wherein the second inductor is disposed within a second casing connected to a second conduit through which extends at least a second cable for supplying electrical power to the second set of turns, and wherein the first inductor is not disposed within said second casing.

According to this embodiment, the second inductor may for example be disposed in a casing made of plastics material, which may be separate from, and separately movable with respect to, a unit such as a housing or cabinet accommodating the electric storage device, the first and second switching devices and at least a portion of each of the first and second branches of the connecting circuitry. The casing which houses the second inductor can be connected to the cabinet by the conduit accommodating the cable for supplying electrical power to the second inductor. An arrangement in which the second inductor and the casing which houses the second inductor is connected to other components of the apparatus by means of a conduit such that the second inductor can be moved relative to such other components can advantageously be used to bring the second inductor in proximity with body tissue without moving these other components (e.g. a cabinet which houses these other components and which may be much larger and heavier than the second inductor and the casing accommodating the second inductor).

Alternatively the first and second inductors could be accommodated in the same housing.

In one embodiment, the first inductor is wound on a first core and the second inductor is wound on a second core different from the first core. The first inductor and the second inductor are therefore substantially not magnetically coupled, at least not via a core that is common to both inductors.

In one embodiment, the first inductor and the second inductor are moveable independently from each other, in particular while still connected to the rest of the apparatus, and in particular while being energized or in use. Nevertheless, the connection to the rest of the apparatus will of course impose a restriction in terms of the area or radius around the remainder of the apparatus within which the first and second inductors can be moved.

In one embodiment, a first inductance of the first inductor and/or a second inductance of the second inductor is one of discretely variable and substantially continuously variable. This enables the resonant frequency of the resonant circuit(s) to be varied in a discrete or substantially continuous manner.

In one embodiment, the electric storage device comprises a pulse capacitor which can be charged by a charging circuit. The charging circuit may form part of the apparatus, or may be provided as a separate device for connection to the apparatus of the fourteenth aspect. The charging circuit may in particular comprise a voltage source and a switch to selectively connect the voltage source to the capacitor.

In a fifteenth aspect, which is an aspect of the present invention, there is provided a method of generating a magnetic field, the method comprising:

providing an apparatus according to the fourteenth aspect;

storing electrical energy in the electric storage device;

switching the first switching device so as to electrically connect the electric storage device to the first inductor and thereby enabling electrical current to flow through the first branch and the first inductor in the first current direction of current flow with respect to the electric storage device, caused by the electrical energy stored by means of the electric storage device, thereby causing the first inductor to generate the first magnetic field; and switching the second switching device so as to electrically connect the electric storage device to the second inductor and thereby enabling electrical current to flow through the second branch and the second inductor in the second current direction of current flow with respect to the electric storage device, caused by the electrical energy stored by means of the electric storage device, thereby causing the second inductor to generate the second magnetic field.

Embodiments described in connection with the fourteenth aspect similarly apply to the fifteenth aspect, and vice versa.

In one embodiment, the apparatus is operated in a pulsed manner, wherein the electrical current flowing through the first branch represents a first half pulse and wherein the electrical current flowing through the second branch represents a second half pulse, the first half pulse and the second half pulse together forming a pulse.

Whilst the apparatus according to this embodiment is operated such that at least one (full) pulse is performed, each branch and each of the first and second inductors is used to perform only one half pulse.

In one embodiment, switching the second switching device comprises switching the second switching device after a delay after an end of the first half pulse. The delay may in particular be variable or selectable, in particular by a user. The two half pulses can therefore be performed substantially independently from one another. The delay may, for example, be set by a user via a user interface, for example a dial or touchscreen of the apparatus. The apparatus may include analog circuitry and/or a microcontroller in order to control the second switching device in accordance with the selected delay.

In one embodiment, the first half pulse has a first duration, wherein the delay is longer than the first duration. According to this embodiment, the second half pulse therefore does not take place immediately after the end of, or very shortly after, the first half pulse. Alternatively, the delay may be chosen to be shorter than the first duration.

In one embodiment, the method comprises bringing the first inductor into proximity with body tissue, or bringing the body tissue into proximity with the first inductor, so that the first magnetic field is present in said body tissue. This may in particular be used for therapeutic purposes, but can also be used for non-therapeutic purposes.

In one embodiment, the method further comprises varying the first magnetic field in the body tissue so as to generate a voltage in the body tissue or to cause a movement of charges in the body tissue. As the magnetic field in the body tissue varies with the current through the first inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction, in the body tissue, wherein preferably the generated voltage or the movement of charges is sufficient to cause a therapeutic effect.

A variety of effects can be achieved in a targeted manner using the apparatus of the fourteenth aspect or the method of the fifteenth aspect. In particular, if only the first inductor is brought into proximity with the body tissue (and the second inductor is not brought into proximity with body tissue), the generated voltage or the movement of charges in the body tissue will be oriented in one direction only. If the apparatus is operated in a pulsed manner, with a repeated application of pulses, this will result in an accumulation of this effect.

In one embodiment, the method further comprises bringing the second inductor into proximity with the body tissue, or bringing the body tissue into proximity with the second inductor, so that the second magnetic field is present in said body tissue.

In this context, the second inductor may be brought into proximity with the same body portion as the first inductor, or alternatively a different body portion. Further, the generated voltage or the movement of charges in the body tissue caused by the second inductor may be oriented in the same direction as the generated voltage or the movement of charges in the body tissue caused by the first inductor, or in a different direction, in particular in the opposite direction. If the voltage or the movement of charges in the body tissue respectively caused by the first and second inductors is oriented in the opposite direction, this is expected to reduce the net charge displacement (when considering the effects of the first and second inductors together). If oriented in the same direction, this is expected to increase the net charge displacement (when considering the effects of the first and second inductors together).

In one example, a body part such as a finger, hand, arm etc. can be placed between the two inductors, and depending on the orientation of the inductors to one another, the voltage or the movement of charges in the body tissue respectively caused by the first and second inductors may be oriented in the same direction or the opposite direction or in directions which are neither the same nor opposite.

In a sixteenth aspect, which is an aspect of the present invention, there is provided an apparatus for use with a first inductor and a second inductor, the first inductor for generating a magnetic field for application to body tissue, the apparatus comprising:

an electric storage device for storing electrical energy;

a first terminal for connection to the first inductor for generating a first magnetic field for application to body tissue;

a second terminal for connection to the second inductor for generating a second magnetic field;

connecting circuitry between the electric storage device and the first and second terminals, wherein the connecting circuitry comprises at least a first branch leading to the first terminal and a second branch leading to the second terminal;

a first switching device, wherein the first switching device forms part of the first branch, wherein the first switching device is configured to electrically connect the electric storage device to the first terminal so as to enable electrical current to flow through the first branch and through the first inductor via said first terminal when the first inductor is connected to the apparatus via said first terminal, caused by the electrical energy stored by means of the electric storage device, thereby causing the first inductor to generate the first magnetic field, wherein the electrical current flowing through the first branch represents a first current direction of current flow with respect to the electric storage device; and a second switching device, wherein the second switching device forms part of the second branch, wherein the second switching device is configured to electrically connect the electric storage device to the second terminal so as to enable electrical current to flow through the second branch and through the second inductor via said second terminal when the second inductor is connected to the apparatus via said second terminal, caused by the electrical energy stored by means of the electric storage device, thereby causing the second inductor to generate the second magnetic field, wherein the electrical current flowing through the second branch represents a second current direction of current flow with respect to the electric storage device, wherein the second current direction of current flow is opposite the first current direction of current flow.

The apparatus of the sixteenth aspect is similar to the apparatus of the fourteenth aspect. However, in contrast to the fourteenth aspect, the first and second inductors mentioned in connection with the sixteenth aspect do not form part of the apparatus of the sixteenth aspect. Instead, the apparatus of the sixteenth aspect has first and second terminals (such as electric sockets or similar) for connection to the first and second inductors, respectively. Accordingly, a number of (different) inductors, for example inductors having different shapes, inductances or other characteristics, can selectively be connected to the apparatus of the sixteenth aspect and used as the first and second inductors.

In any embodiments described herein, the (first) inductor and/or an applicator in which the (first) inductor is accommodated may, for example, be of a generally flat construction so that the (first) inductor and/or applicator may be applied to a body portion substantially from one side. Other shapes or construction types are also possible, for example that of a hollow cylinder or similar, so that the windings of the (first) inductor may surround the body portion, i.e. the (first) inductor or applicator may be applied over the body portion, or the body portion (e.g. arm, leg, torso) may be introduced into, or pass through, the inductor or applicator.

Further, the construction of any, some or all of the inductors discussed in the present application, in particular of the (first) inductor, is not limited to any particular design. In particular, any, some or all of the inductors, in particular the (first) inductor, may, for example, be constructed in such a way that each (360°) turn or winding of the respective inductor comprises, or consists of, one solid (and substantially rigid) piece of conductive material (e.g. copper), rather than several strands running in parallel. Alternatively, each (360°) turn or winding of the respective inductor may comprise, or consist of, a small number (such as no more than 2, or no more than 3, or no more than 4, or no more than 5) of solid (and substantially rigid) pieces of conductive material (e.g. copper), insulated from one another. In other embodiments, any, some or all of the inductors, in particular the first inductor, may, for example, be constructed from litz-wire, wherein each wire is insulated separately, and may in particular comprise a litz-wire coil. This may reduce eddy currents in the inductor.

The various embodiments and advantages described above in connection with any one aspect of the present invention or the present disclosure similarly apply to the other aspects of the present disclosure or of the invention. Each feature disclosed and/or illustrated in the present specification may be incorporated in the invention, whether alone or in combination with any other feature disclosed or illustrated herein, unless such combination is explicitly excluded or technically impossible. In particular, (embodiments of) the first to thirteenth aspects can be combined with (embodiments of) the fourteenth to sixteenth aspects.

Some embodiments of the invention will now be described by way of example only and with reference to the accompanying drawings, in which:

FIG. 1 schematically shows a circuit diagram of a device for generating an alternating magnetic field known to the inventor (and not admitted as prior art).

FIG. 2 schematically shows a circuit diagram of an apparatus for generating a magnetic field in accordance with an embodiment of the present disclosure.

FIG. 3 schematically shows a circuit diagram of an apparatus for generating a magnetic field in accordance with an embodiment of the present disclosure.

FIG. 4 schematically shows a circuit diagram of an apparatus for generating a magnetic field in accordance with an embodiment of the present disclosure.

FIG. 5 schematically shows an apparatus for generating a magnetic field in accordance with an embodiment of the present disclosure.

Figure 8:
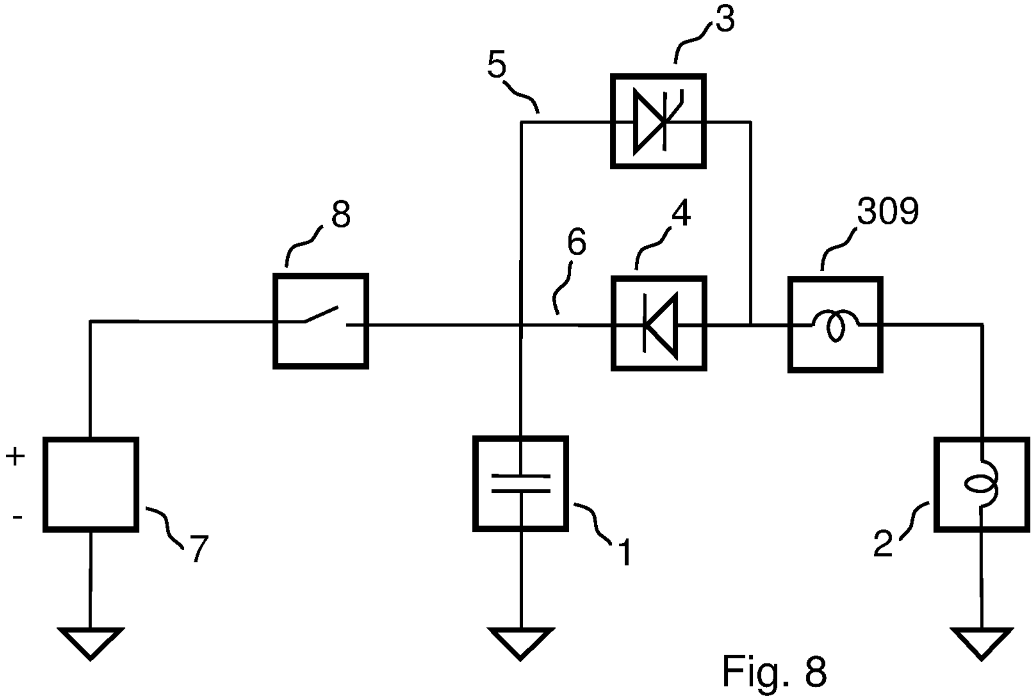

FIG. 8 schematically shows a circuit diagram of an apparatus for generating a magnetic field in accordance with an embodiment of the present disclosure.

Figure 9:
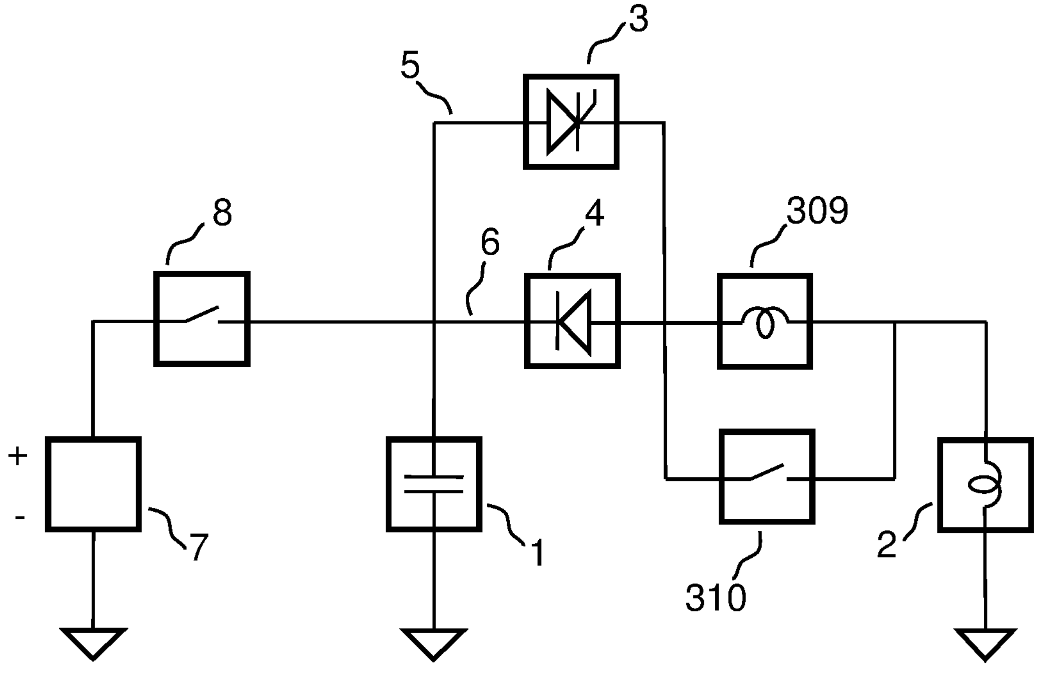

FIG. 9 schematically shows a circuit diagram of an apparatus for generating a magnetic field in accordance with an embodiment of the present disclosure.

Figure 10:
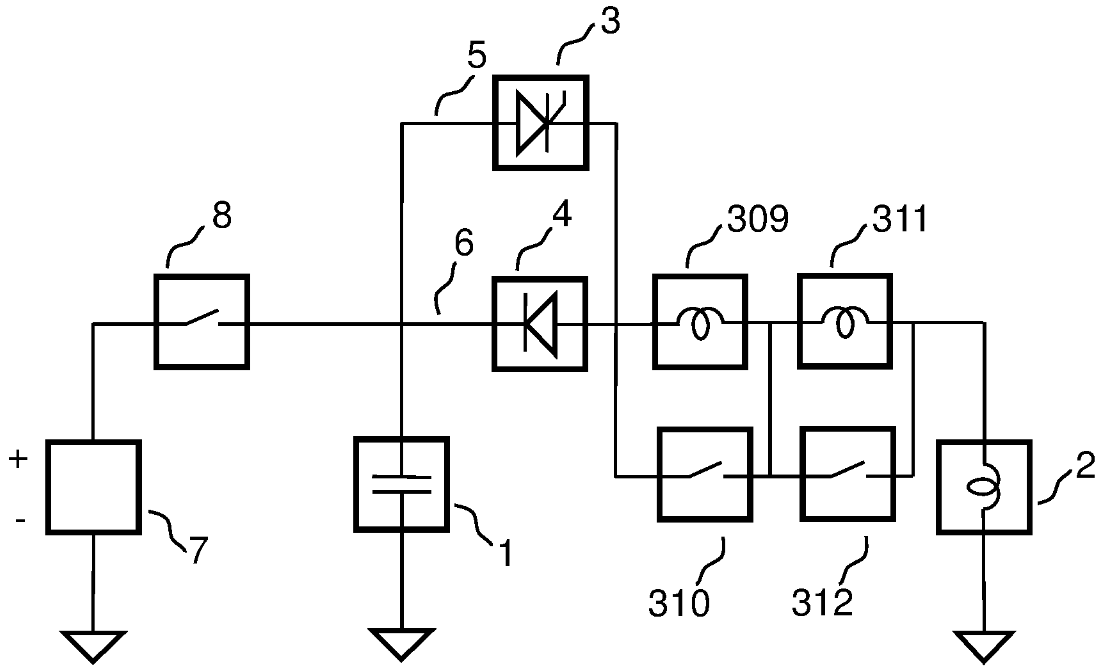

FIG. 10 schematically shows a circuit diagram of an apparatus for generating a magnetic field in accordance with an embodiment of the present disclosure.

Figure 11:
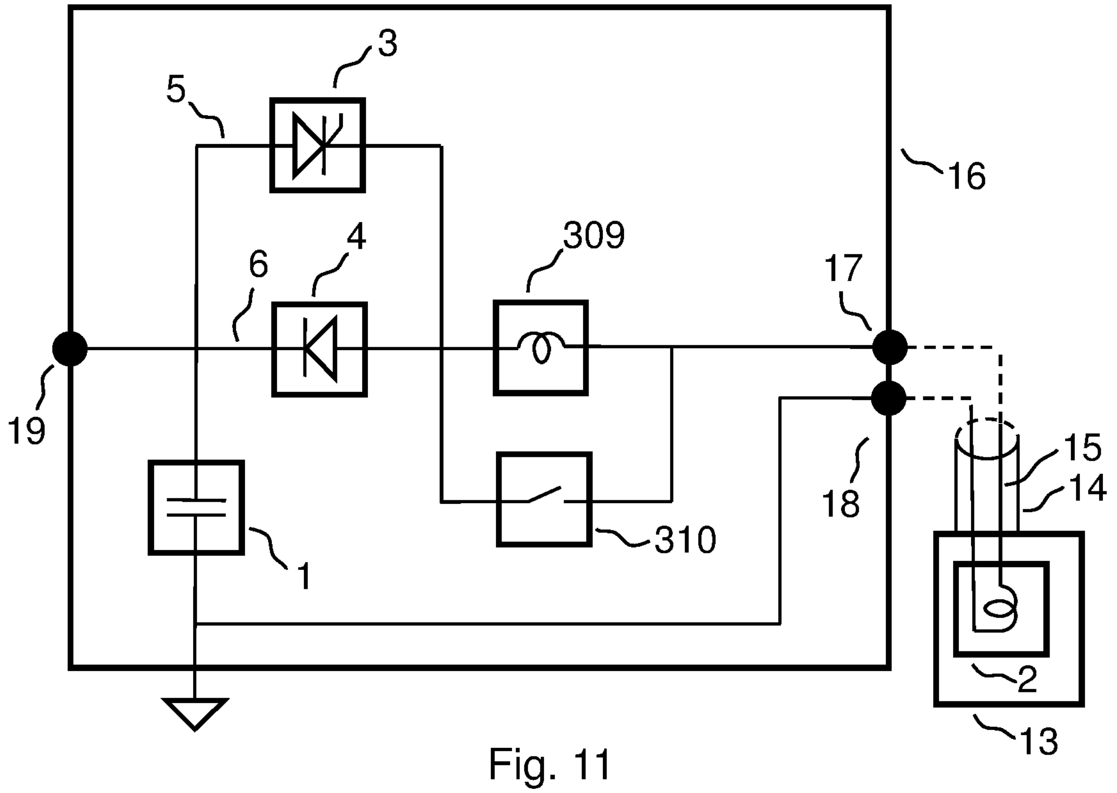

FIG. 11 schematically shows an apparatus for generating a magnetic field in accordance with an embodiment of the present disclosure.

Figure 12:
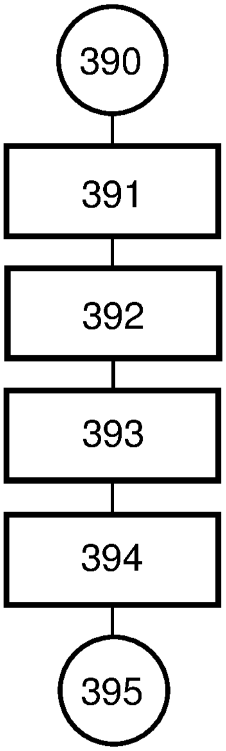

FIG. 12 shows a flowchart illustrating a method in accordance with an embodiment of the present disclosure.

Figure 13:
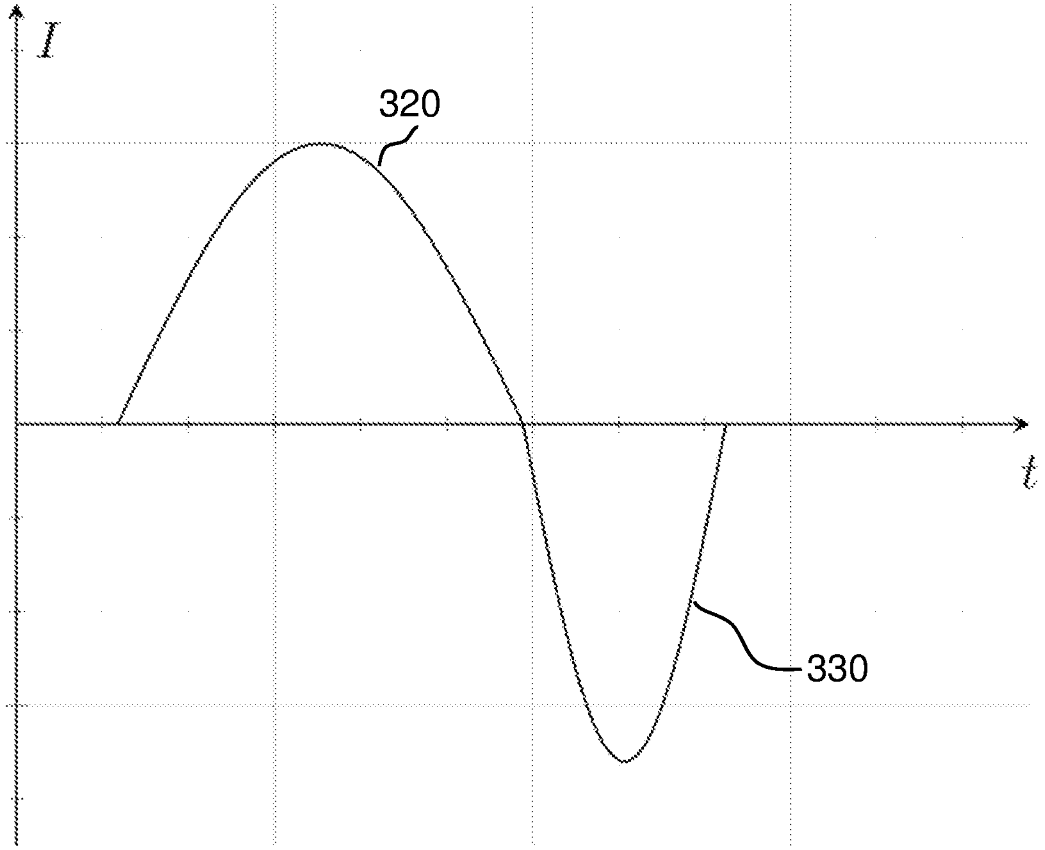

FIG. 13 shows a diagram in which the current through the first inductor is plotted over time, in accordance with an embodiment of the present disclosure.

Figure 14:
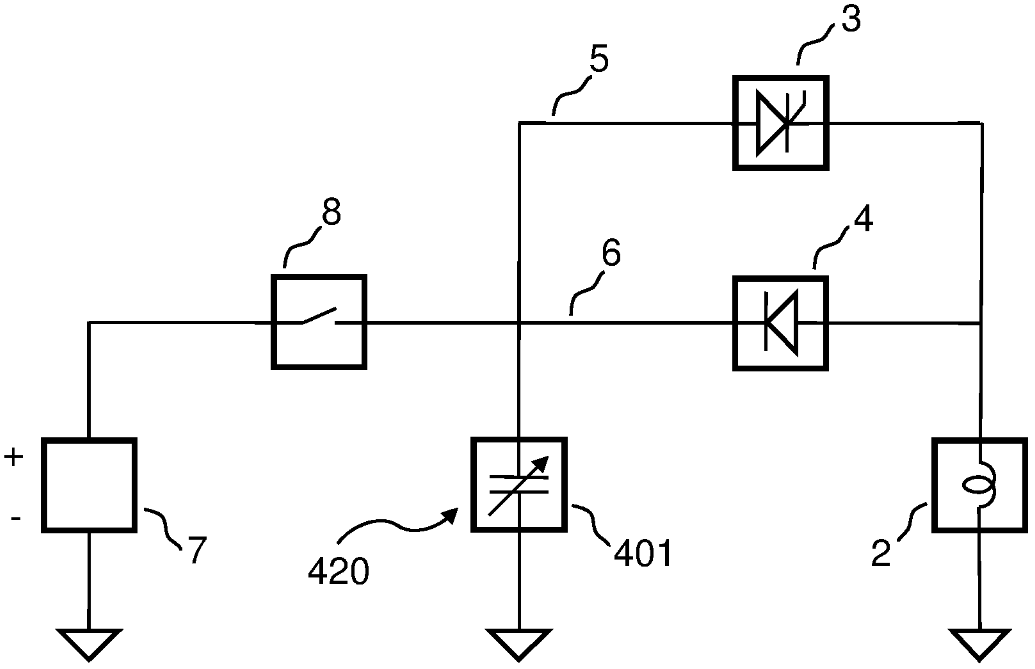

FIG. 14 schematically shows a circuit diagram of an apparatus for generating a magnetic field in accordance with an embodiment of the present disclosure.

Figure 15:
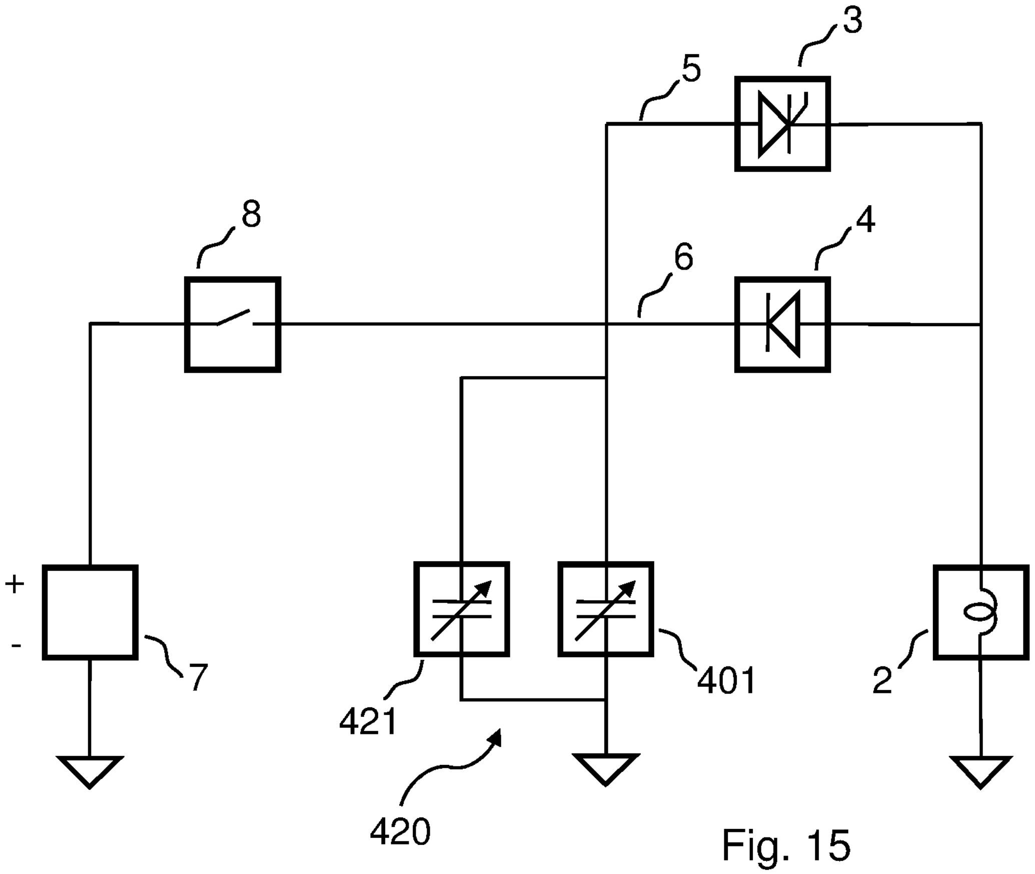

FIG. 15 schematically shows a circuit diagram of an apparatus for generating a magnetic field in accordance with an embodiment of the present disclosure.

Figure 16:
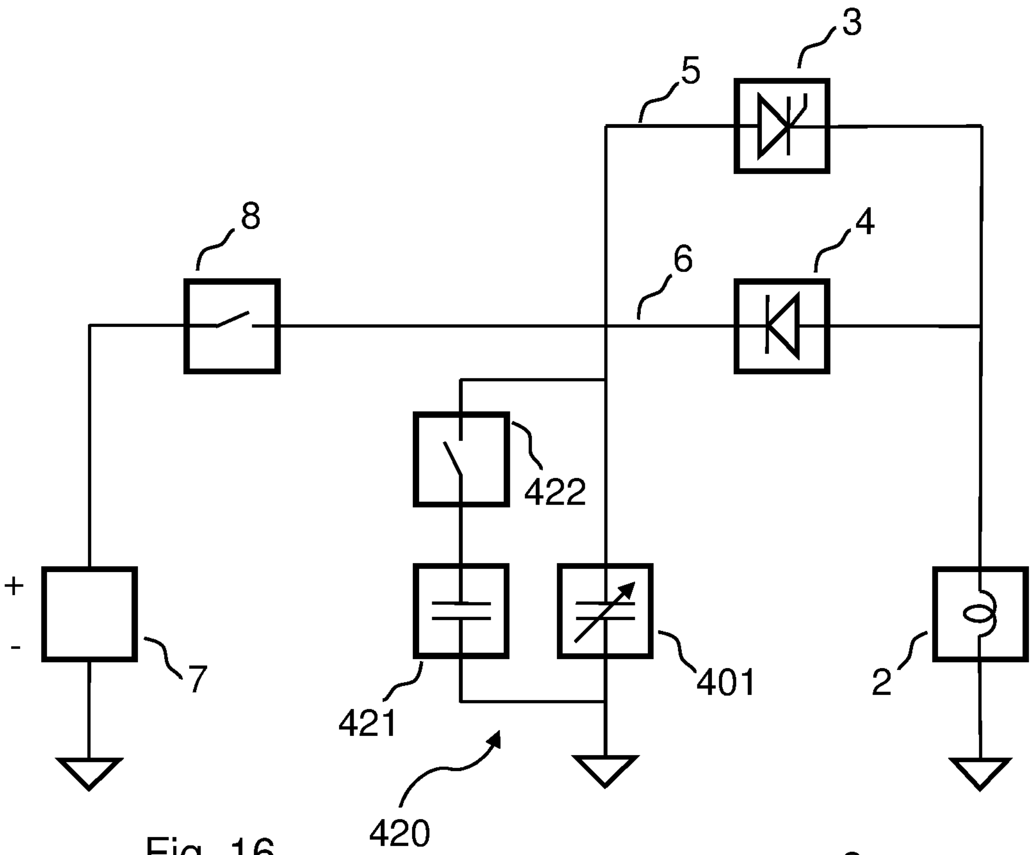

FIG. 16 schematically shows a circuit diagram of an apparatus for generating a magnetic field in accordance with an embodiment of the present disclosure.

Figure 17:
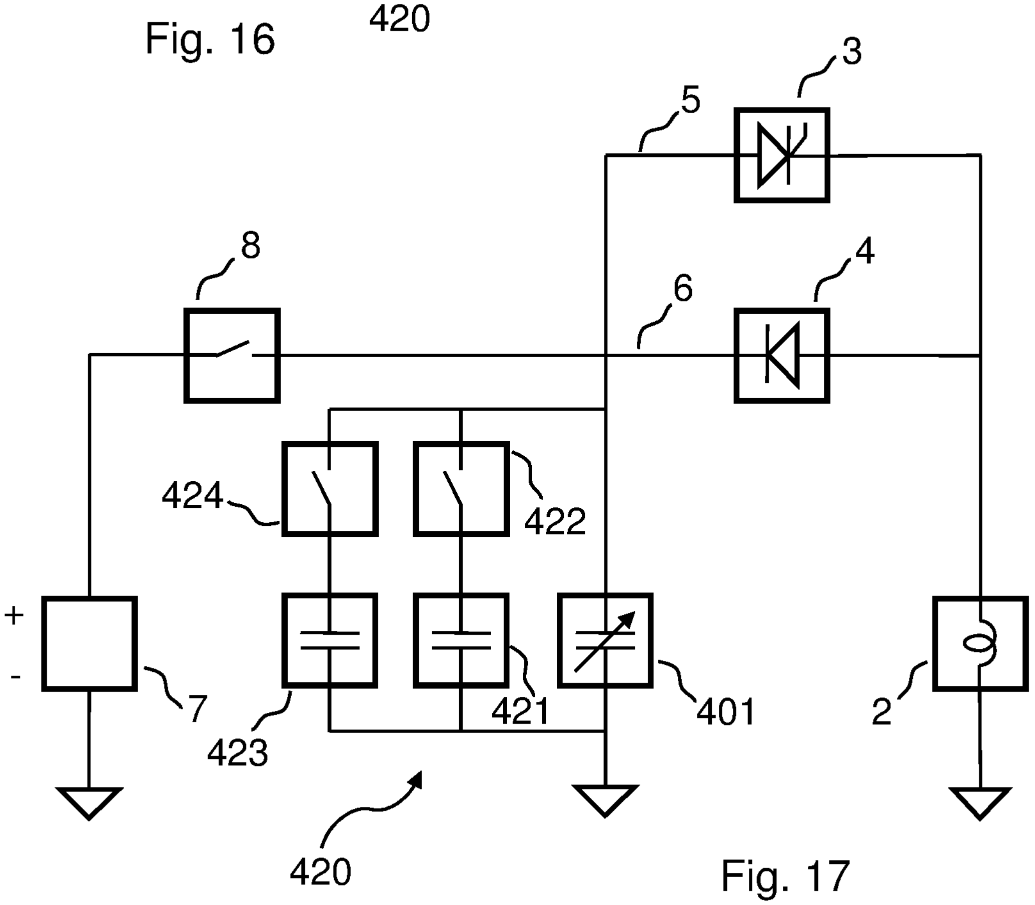

FIG. 17 schematically shows a circuit diagram of an apparatus for generating a magnetic field in accordance with an embodiment of the present disclosure.

Figure 18:
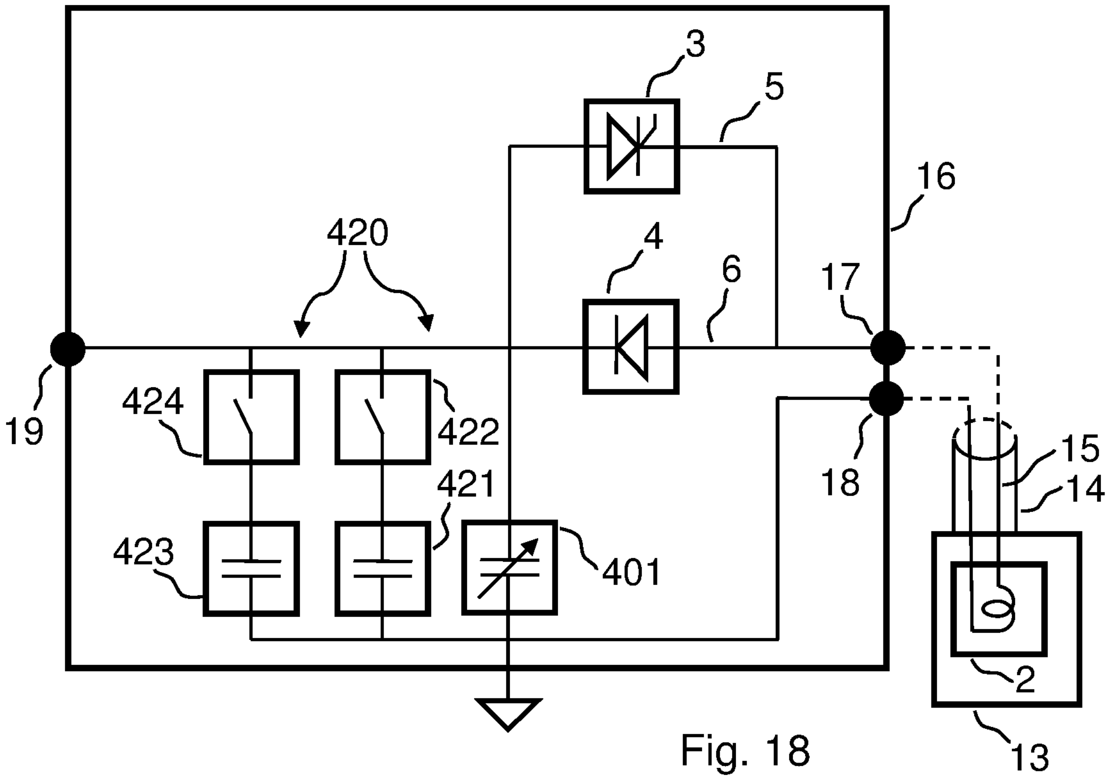

FIG. 18 schematically shows an apparatus for generating a magnetic field in accordance with an embodiment of the present disclosure.

Figure 19:
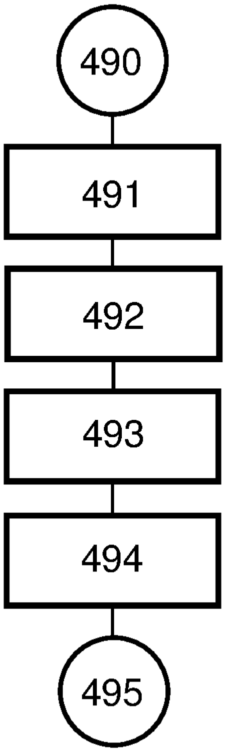

FIG. 19 shows a flowchart illustrating a method in accordance with an embodiment of the present disclosure.

Figure 20:
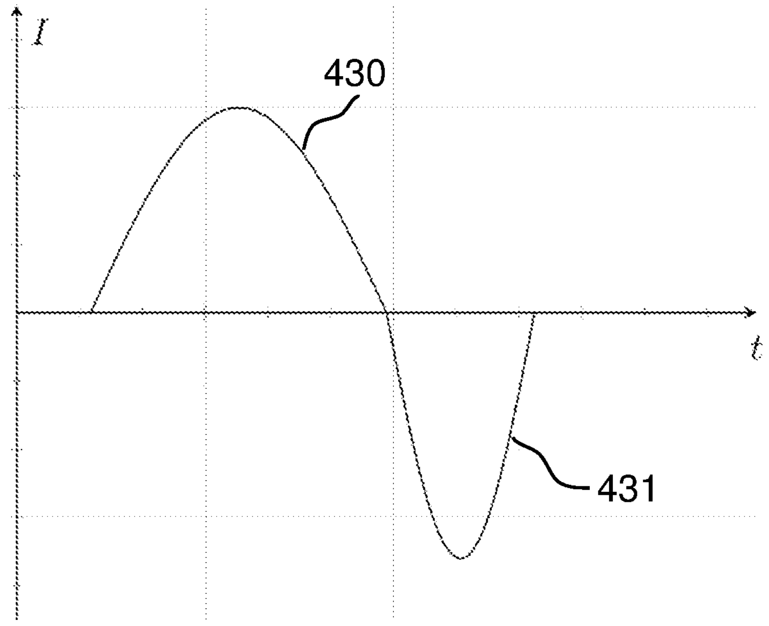

FIG. 20 shows a diagram in which the current through the (first) inductor is plotted over time, in accordance with an embodiment of the present disclosure.

Figure 21:
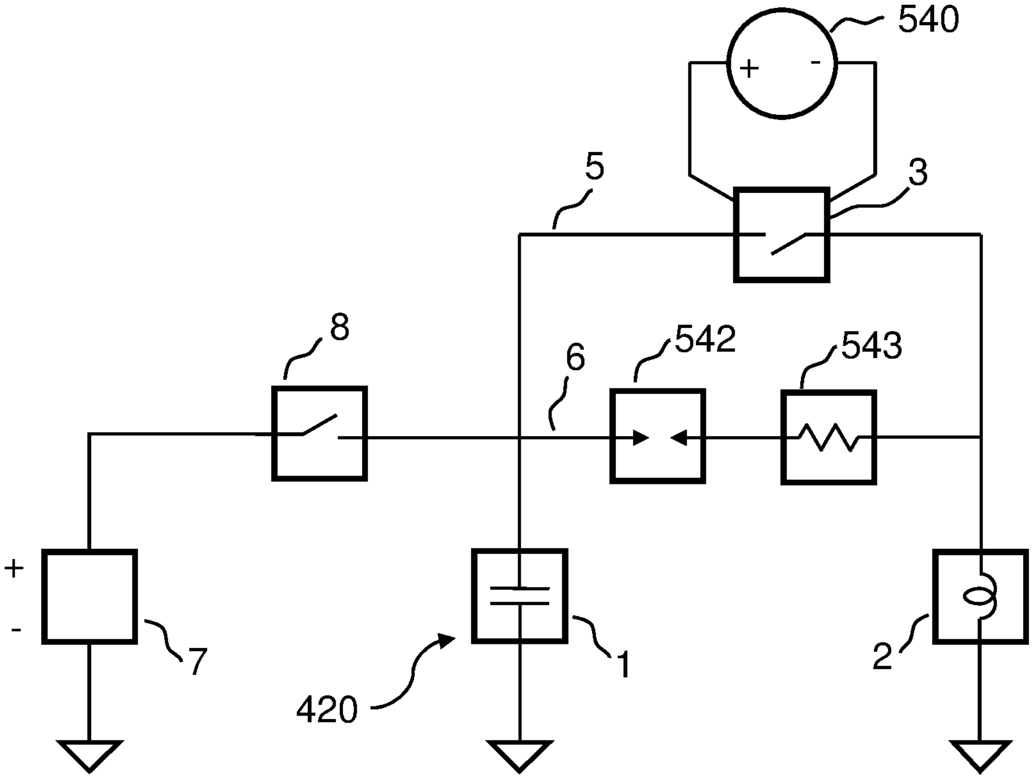

FIG. 21 schematically shows a circuit diagram of an apparatus for generating a magnetic field in accordance with an embodiment of the present disclosure.

Figure 22:
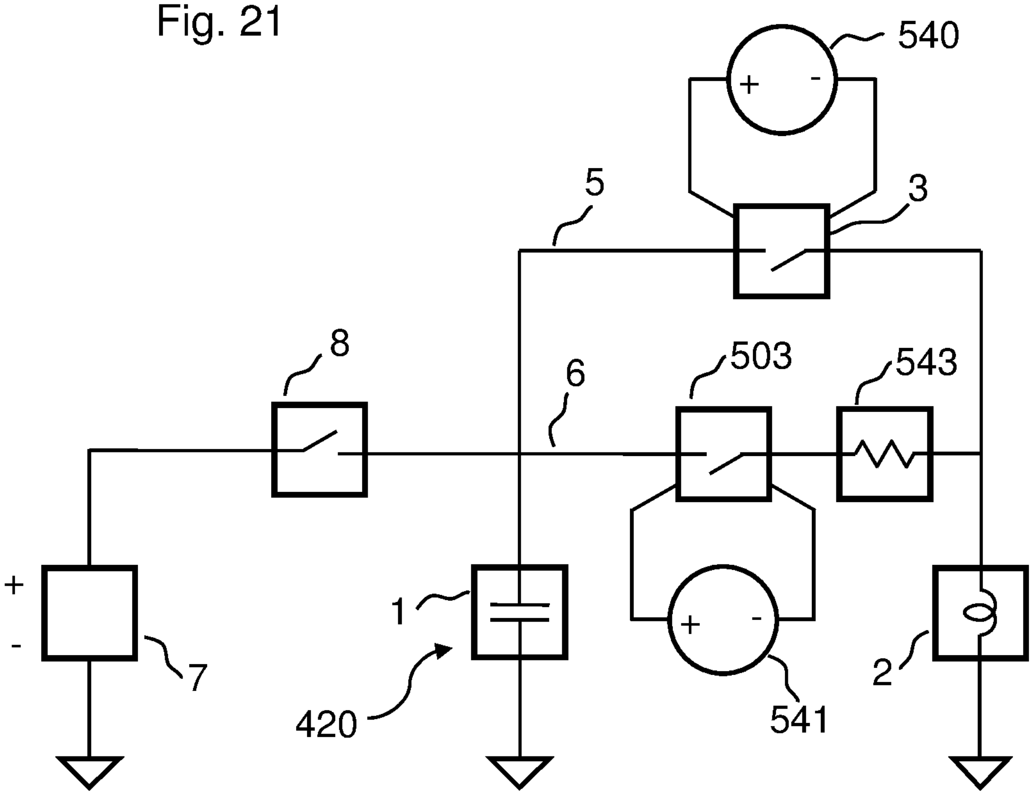

FIG. 22 schematically shows a circuit diagram of an apparatus for generating a magnetic field in accordance with an embodiment of the present disclosure.

Figure 23:
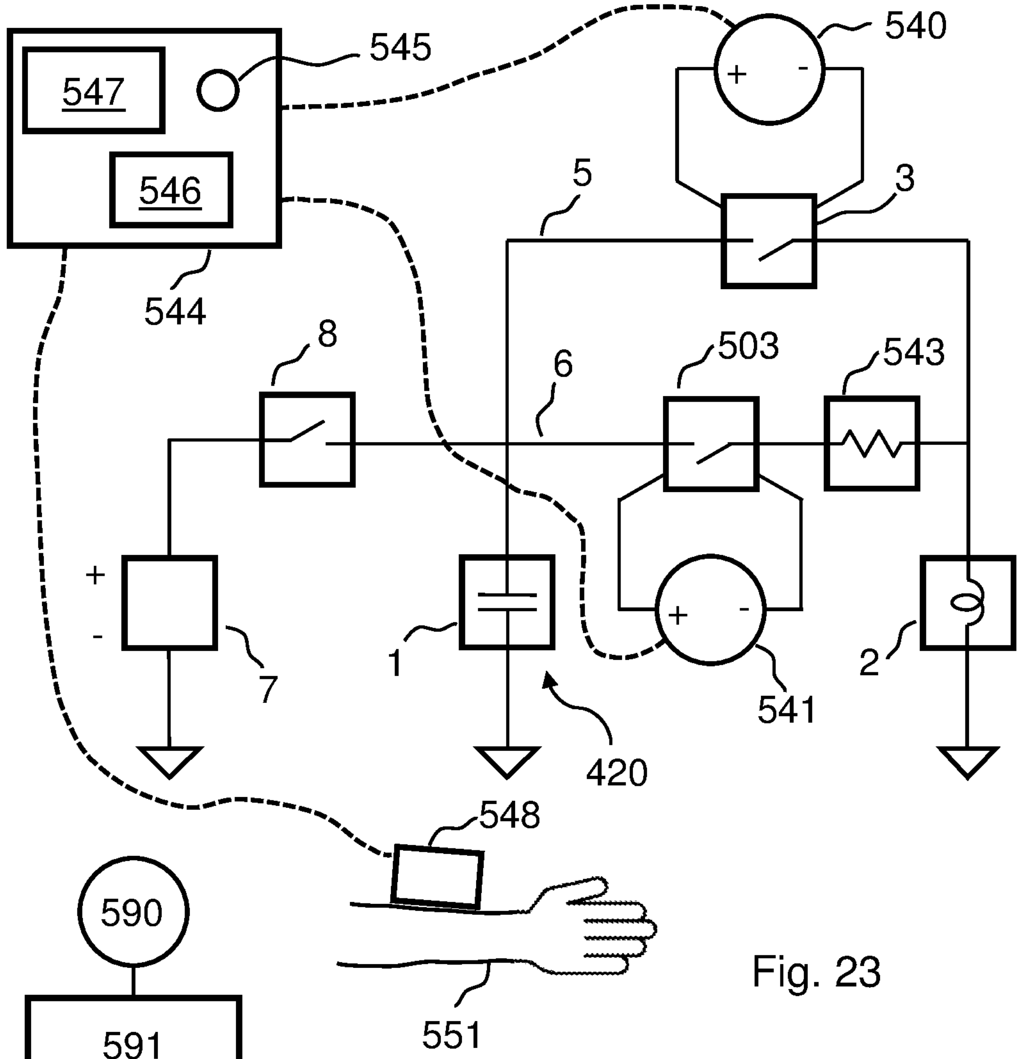

FIG. 23 schematically shows an apparatus for generating a magnetic field in accordance with an embodiment of the present disclosure.

Figure 24:
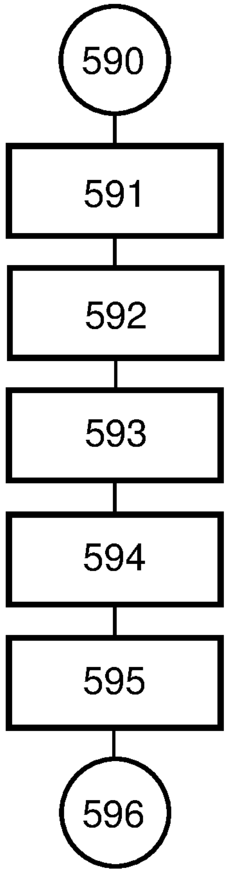

FIG. 24 shows a flowchart illustrating a method in accordance with an embodiment of the present disclosure.

Figure 25:
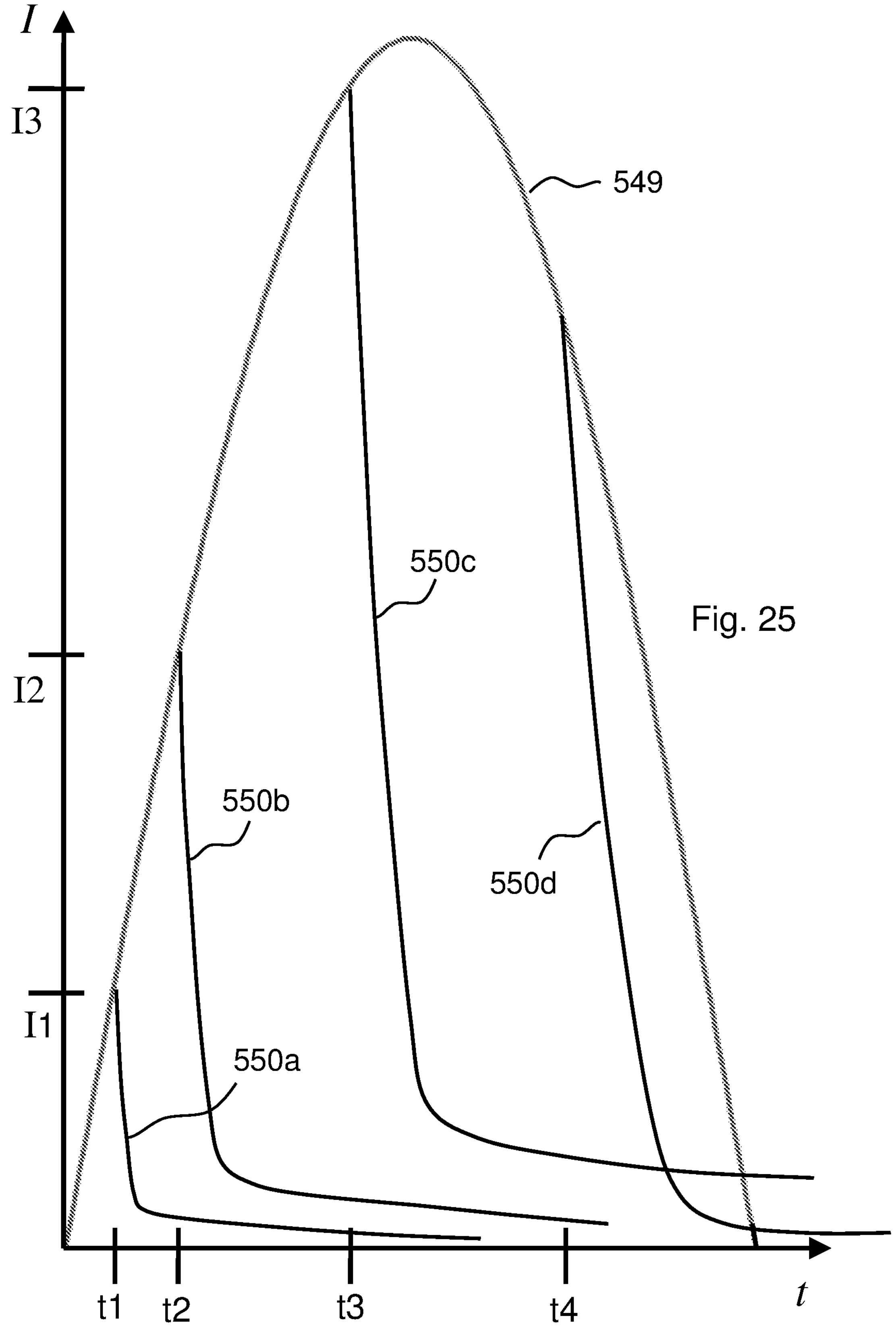

FIG. 25 shows a diagram in which the current through the (first) inductor is plotted over time, in accordance with an embodiment of the present disclosure.

Figure 26:
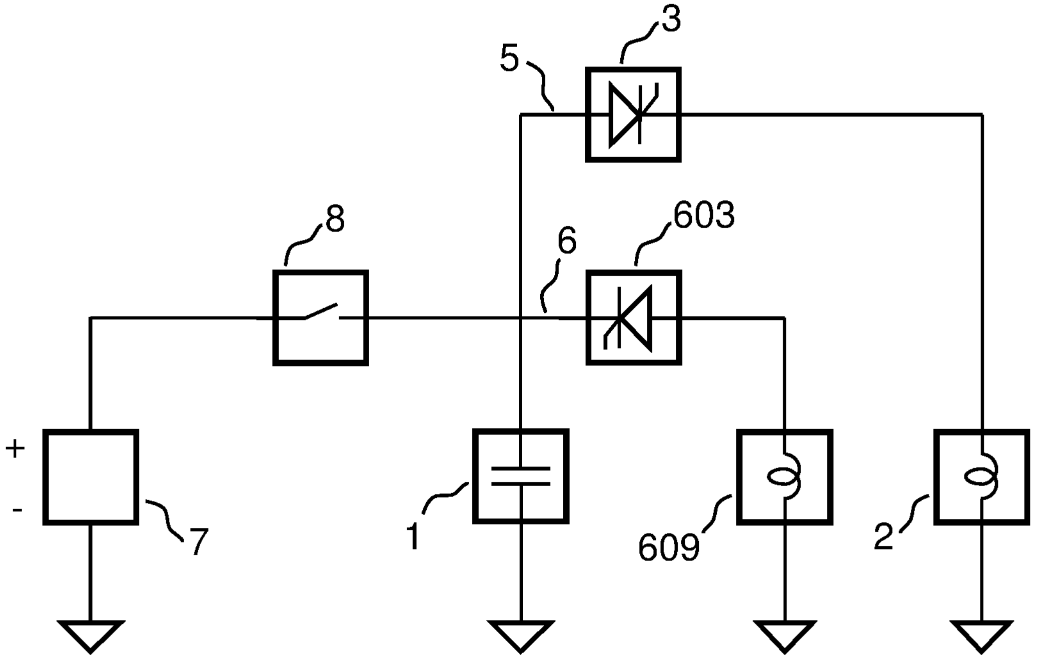

FIG. 26 schematically shows a circuit diagram of an apparatus for generating a magnetic field in accordance with an embodiment of the present invention.

Figure 27:
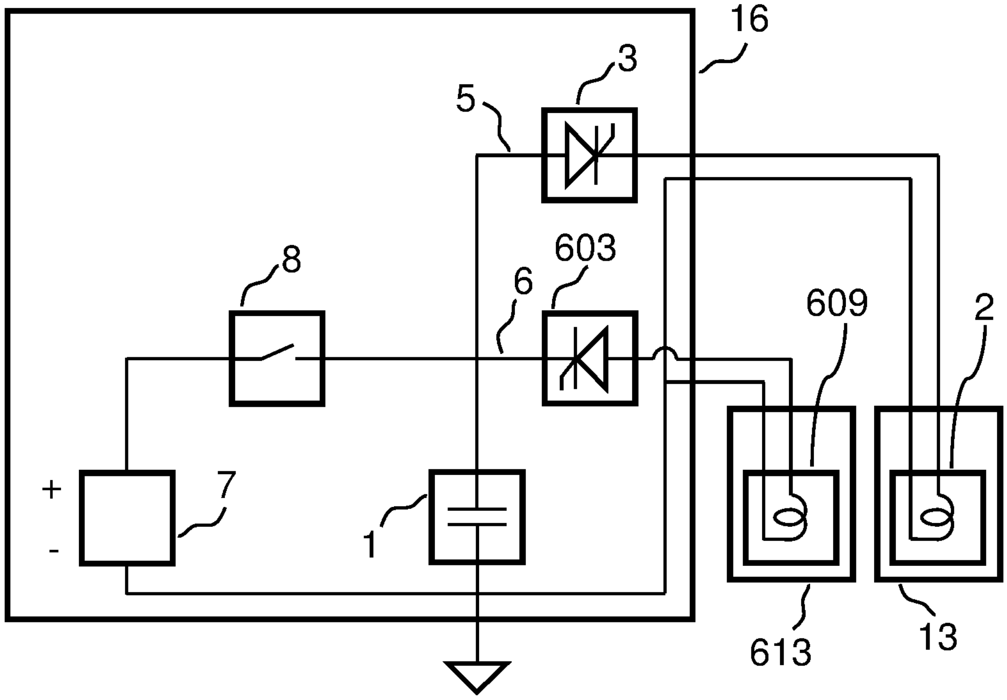

FIG. 27 schematically shows an apparatus for generating a magnetic field in accordance with an embodiment of the present invention.

Figure 28:
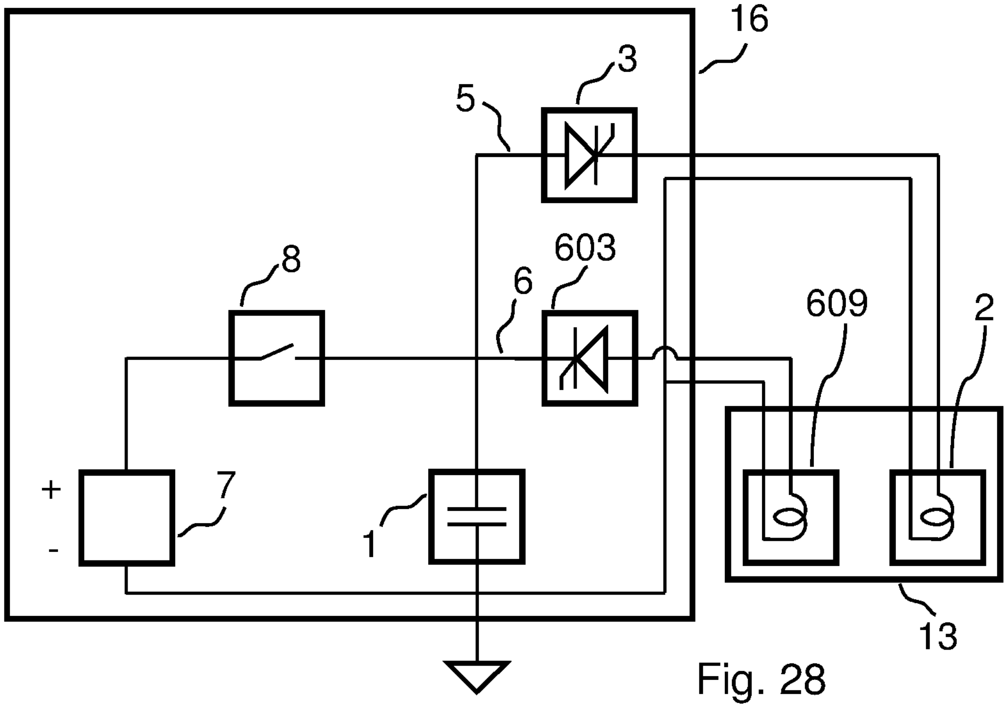

FIG. 28 schematically shows an apparatus for generating a magnetic field in accordance with an embodiment of the present invention.

Figure 29:
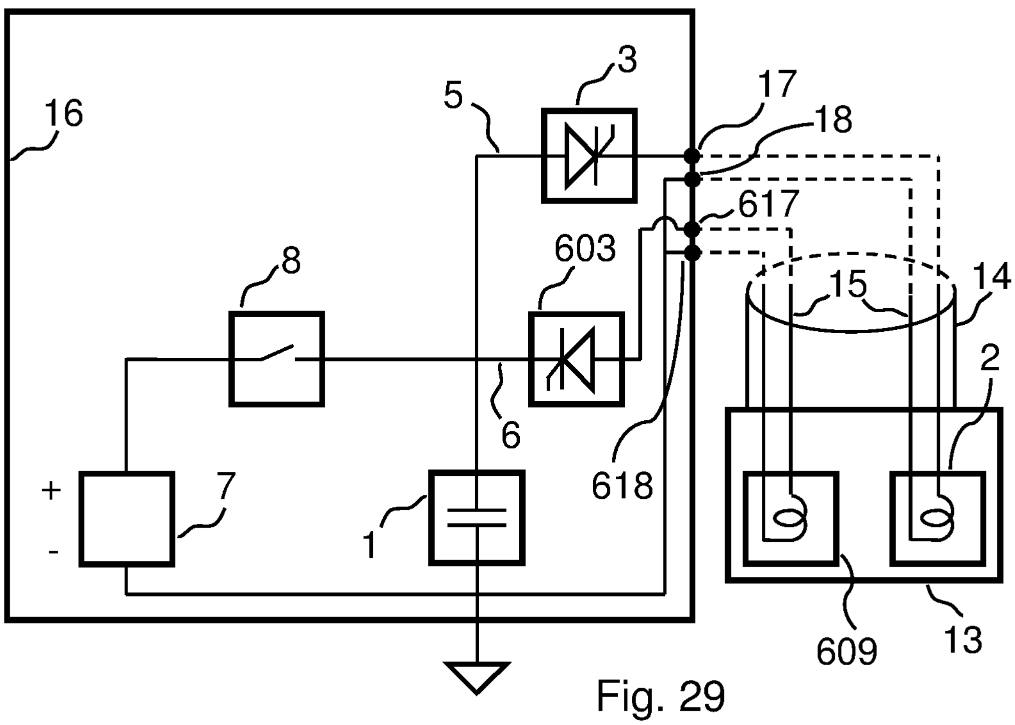

FIG. 29 schematically shows an apparatus for generating a magnetic field in accordance with an embodiment of the present invention.

Figure 30:
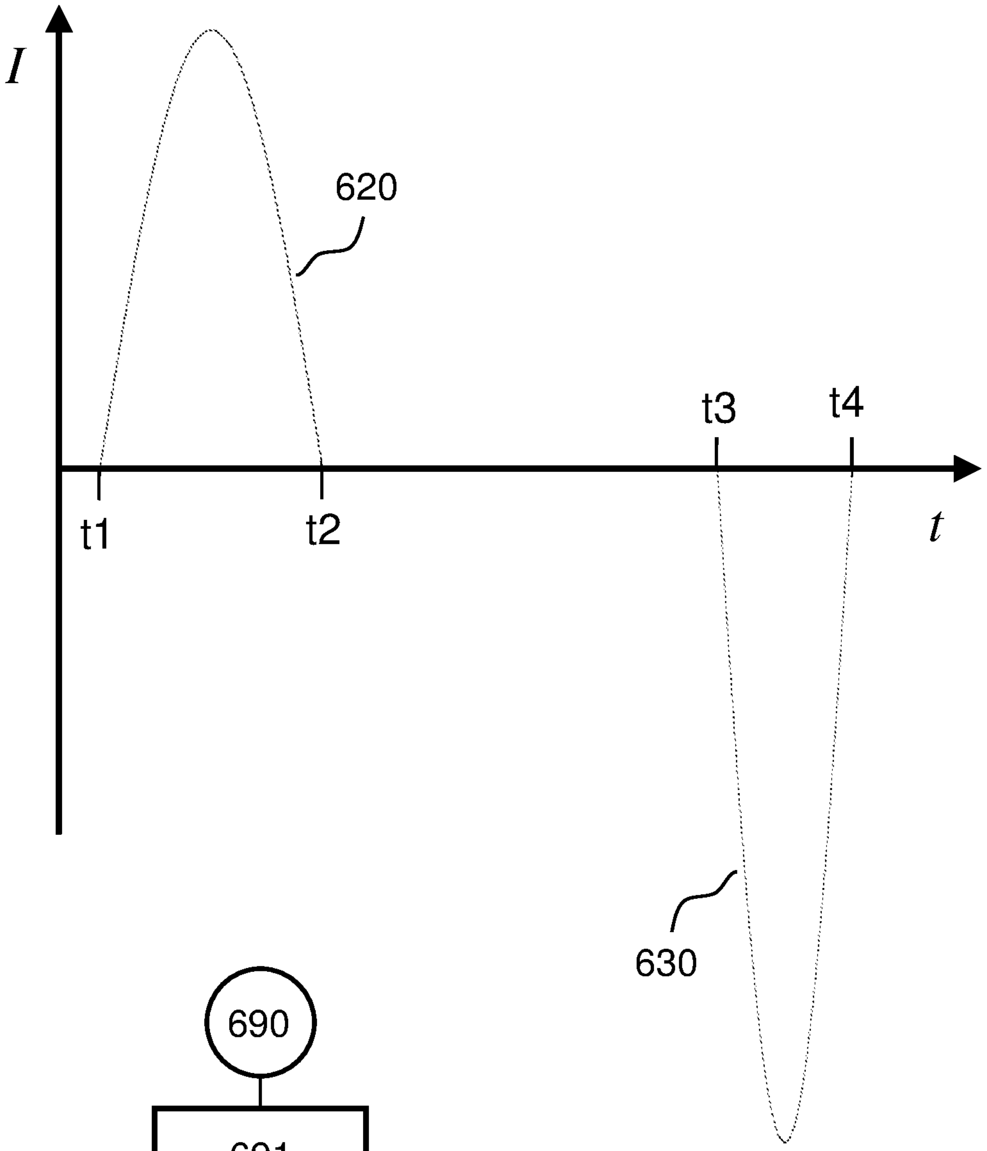

FIG. 30 shows a diagram in which the current through the first inductor and the second inductor is plotted over time, in accordance with an embodiment of the present invention.

Figure 31:
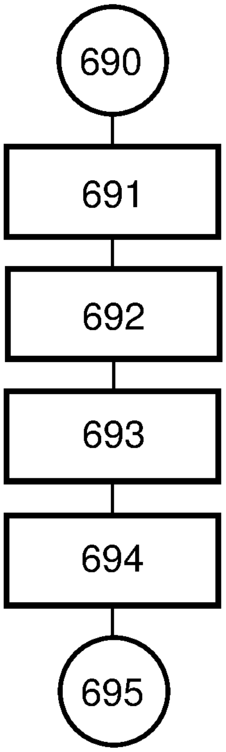

FIG. 31 shows a flowchart illustrating a method in accordance with an embodiment of the present invention.

Figure 1:
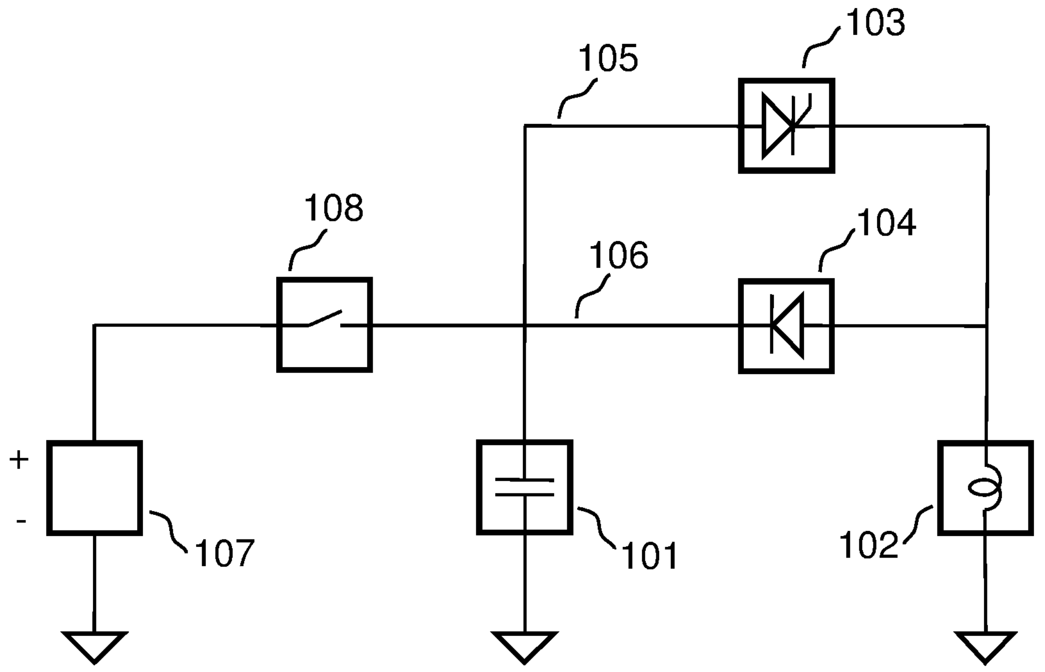
Figure 2:
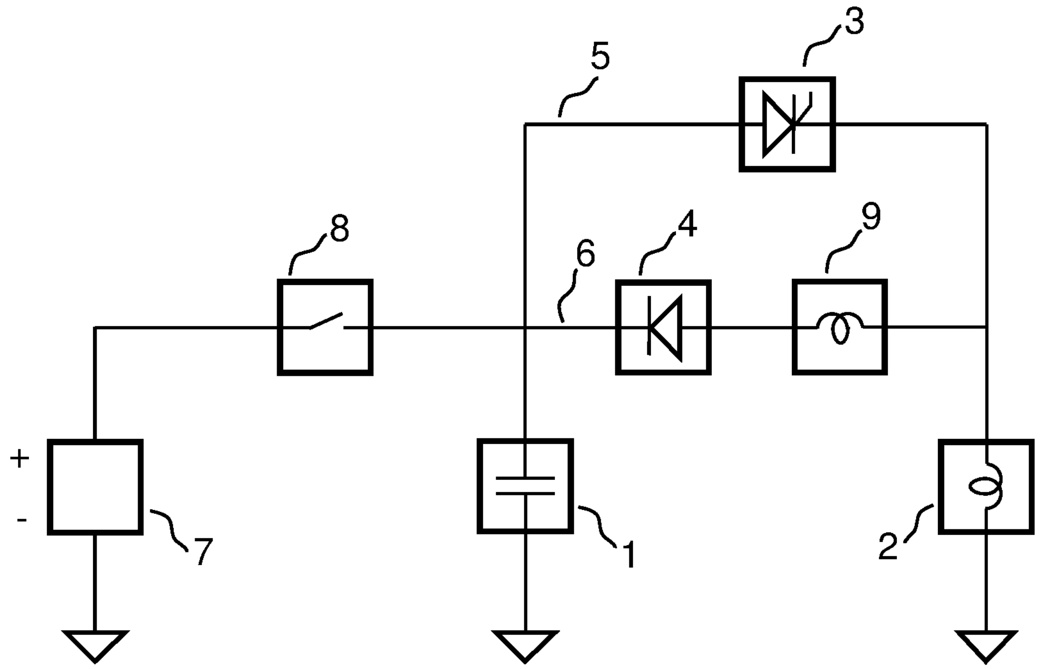

FIG. 2 schematically shows a circuit diagram of an apparatus for generating a magnetic field in accordance with an embodiment of the present disclosure. The circuit diagram shown in FIG. 2 is similar to that shown in FIG. 1. The above explanations regarding the device shown in FIG. 1 therefore also apply to the circuit diagram shown in FIG. 2 and will not be repeated here. Elements shown in FIG. 2 corresponding to elements shown in FIG. 1 carry the same reference signs reduced by 100. However, it should be noted that various modifications are possible. For example, while in many embodiments the source of electrical energy 7 (e.g. a voltage source 7) may be mains powered, it can alternatively be non-mains powered and may, for example, comprise a battery or a battery arrangement comprising one or more batteries. Switching device 3 is shown as a thyristor, but other switching devices can be used, as has been explained above. Electric component 4 in the second branch 6 is shown as a diode, but other electric components or an assembly of electric components, in particular electronic components or an assembly of electronic components, can be used, as has been explained above. However, in the interest of a compact explanation, the description of the circuit diagram shown in FIG. 2 will proceed using the same terminology as has been used in connection with FIG. 1.

Further, a charging circuit comprising a source of electrical energy 7 and a switching device 8 is shown for better understanding, although the disclosure includes embodiments without such a charging circuit (but which can be used together with such a charging circuit, in particular which can be electrically connected to such a charging circuit).

The second branch 6 shown in FIG. 2 includes a second inductor 9 connected in series with diode 4. Electrical current flowing between the first inductor 2 and the capacitor 1 through the second branch 6 will also flow through the second inductor 9. Considering the current flow through the first inductor 2 and the second branch 6 and the capacitor 1, the second inductor 9 is effectively connected in series with the first inductor 2. No such additional inductor forms part of the first branch 5, and therefore the inductance of the second branch 6 is higher than the inductance of the first branch 5, in particular significantly higher. Therefore, when considering the capacitor 1, the first inductor 2 and either the first branch 5 or the second branch 6 as a resonant circuit, it can be seen that the frequency of the resonant circuit including the second branch 6 is (significantly) lower than the frequency of the resonant circuit including the first branch 5.

Figure 3:
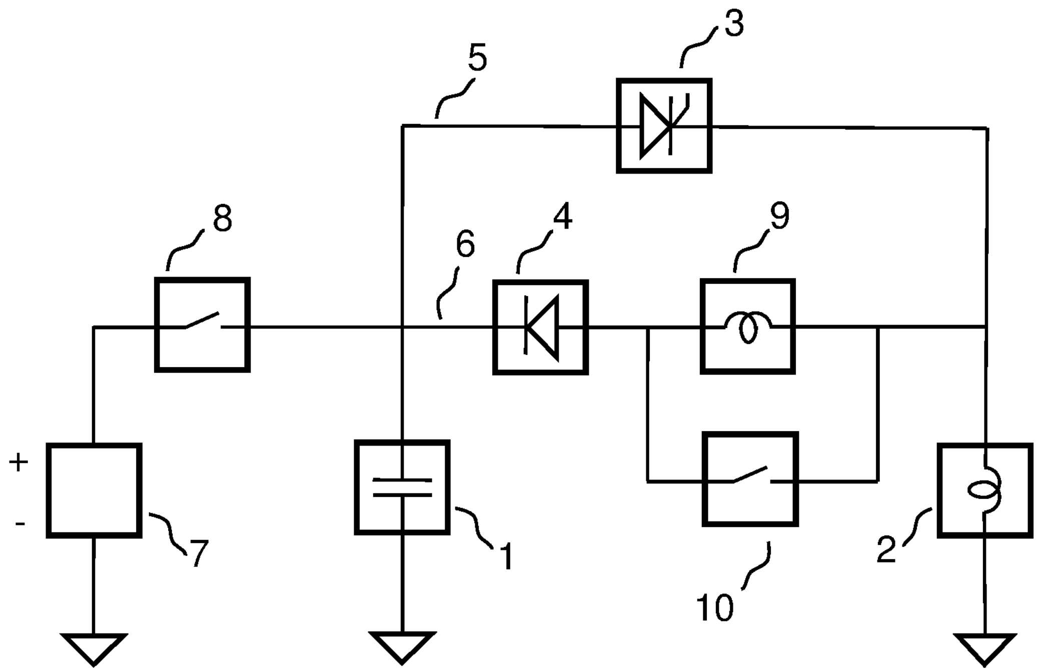

FIG. 3 schematically shows a circuit diagram of an apparatus for generating a magnetic field in accordance with an embodiment of the present disclosure. The embodiment shown in FIG. 3 is similar to that shown in FIG. 2, and the same explanations provided in connection with FIG. 2 also apply to the embodiment shown in FIG. 3. Like components carry like reference signs. FIG. 3 additionally shows circuitry for bypassing or short-circuiting the second inductor 9. This bypass circuitry is connected to the two terminals of the second inductor 9 and includes a further switching device 10 to enable the bypass circuitry to selectively bypass the second inductor 9. When the further switching device 10 is closed (or conductive), any electrical current flowing through the second branch 6 will predominantly or (almost) exclusively flow through the bypass circuitry, thereby substantially preventing current from flowing through the second inductor 9. In this way, the total inductance of the second branch 6 can be changed between a maximum value (further switching device 10 open) and a minimum value (further switching device 10 closed). When the further switching device 10 is closed, the inductance of the second branch 6 may be similar to the inductance of the first branch 5.

Figure 4:
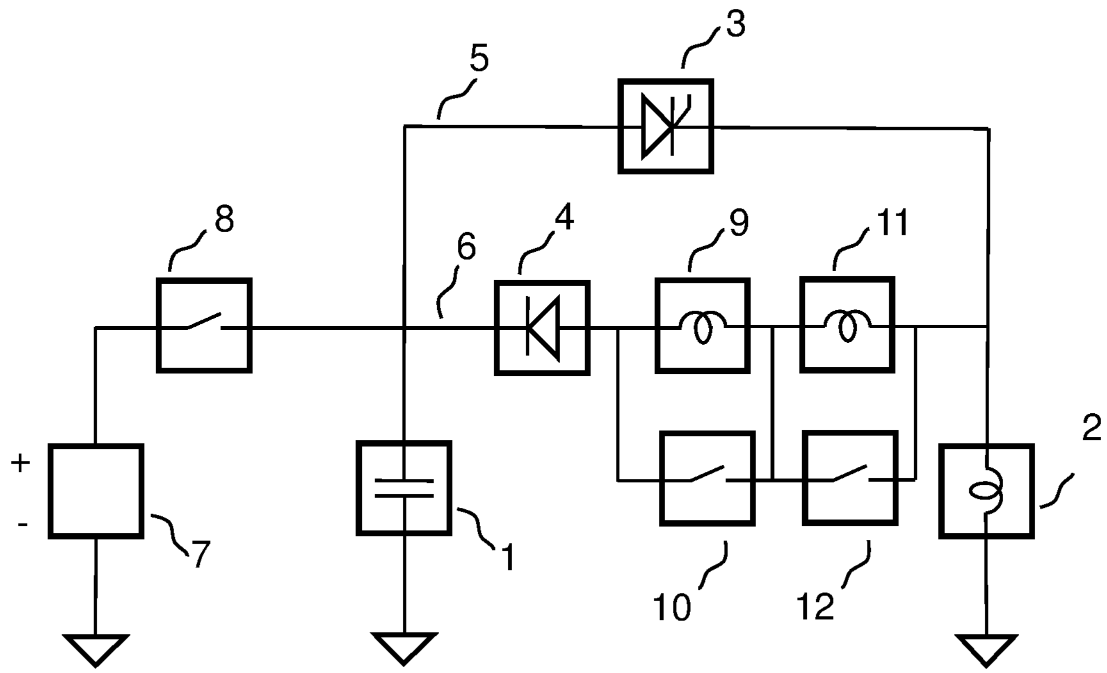

FIG. 4 schematically shows a circuit diagram of an apparatus for generating a magnetic field in accordance with an embodiment of the present disclosure. The embodiment shown in FIG. 4 is similar to that shown in FIG. 3, and the same explanations provided in connection with FIG. 3 also apply to the embodiment shown in FIG. 4. Like components carry like reference signs. FIG. 4 additionally shows a further inductor 11 forming part of the second branch 6 and connected in series with the second inductor 9 (and the diode 4). The circuit diagram shown in FIG. 4 additionally includes further circuitry for bypassing or short-circuiting the further inductor 11. This further bypass circuitry is connected to the two terminals of the further inductor 11 and includes a further switching device 12 to enable the further bypass circuitry to selectively bypass the further inductor 11. When the further switching device 12 is closed (or conductive), any electrical current flowing through the second branch 6 will predominantly or (almost) exclusively flow through the further bypass circuitry, thereby substantially preventing current from flowing through the further inductor 11. In this way, the total inductance of the second branch 6 can be varied.

Using the two further switching devices 10 and 12, the total inductance of the second branch 6 can be changed between a maximum value (both further switching devices 10 and 12 open or non-conductive) and a minimum value (both further switching devices 10 and 12 closed or conductive). When both further switching devices 10 and 12 are closed, the inductance of the second branch 6 may be similar to the inductance of the first branch 5. When only one of the further switching devices 10 and 12 is closed and the other is open, only one of the second inductor 9 and the further inductor 11 will be bypassed, and accordingly the total inductance of the second branch 6 will be at an intermediate value between the minimum value and the maximum value.

According to a variant of the embodiment shown in FIG. 4, the bypass circuitry associated with either the second inductor 9 or the further inductor 11 can be omitted. The respective inductor will therefore be permanently connected in series with the diode 4, whereas the other of the second inductor 9 and the further inductor 11 (the bypass circuitry of which is not omitted) can selectively be bypassed using its associated bypass circuitry.

According to a further variant of the embodiment shown in FIG. 4, yet further inductors can be added to the second branch 6 in series with the diode 4, the second inductor 9 and the further inductor 11. Each of these yet further inductors may or may not have their associated bypass circuitry similar to the bypass circuitry associated with the second inductor 9 and the further inductor 11.

According to a variant of any of the embodiments described with reference to FIGS. 2, 3 and 4 (or any of the variants already explained above), any one or more of the second inductor 9, the further inductor 11 and the yet further inductors (if provided) may comprise inductors with a variable inductance. Details of inductors with a variable inductance have already been explained above.

In a further development of this variant, only one of the inductors in the second branch 6 is of variable inductance, for example the second inductor 9. Nevertheless, by suitable choice of the (maximum) inductance of the second inductor 9 and of the inductance of the further inductors in the second branch 6, the total inductance of the second branch 6 can be adjustable over a relatively wide range, in particular in small steps or (substantially) continuously. In this further development, each of the further inductors is provided with associated bypass circuitry. The second inductor 9 of variable inductance may or may not be provided with associated bypass circuitry. If the inductances of the second inductor (L2) and of the further inductors (L3, L4, L5, L6 etc.) are chosen according to a ratio of 1:1:2:4:8 etc., the lowest value of total inductance of the second branch 6 can be achieved if the third inductor (of inductance L3) and any further inductors (of inductance L4, L5, L6 etc.) are bypassed and the variable inductance (L2) of the second inductor 9 is adjusted to a minimum value L2*min*. By adjusting the variable inductance L2 of the second inductor 9 over its adjustable range to a maximum value L2*max*, the total inductance of the second branch 6 can be adjusted from L2*min* to L2*max*. If (only) the third inductor is not bypassed (and the fourth and any further inductors are bypassed), the total inductance of the second branch 6 can be adjusted from L3+L2*min* to L3+L2*max* by adjusting the variable inductance L2 of the second inductor 9 over its adjustable range. If (only) the fourth inductor is not bypassed (and the third, fifth and any further inductors are bypassed), the total inductance of the second branch 6 can be adjusted from L4+L2*min* to L4+L2*max*. The next adjustable range of the total inductance can be achieved by not bypassing the third and fourth inductor and bypassing the fifth and any further inductors, and so on. If the relative inductances of the second inductor and of the further inductors are chosen according to the above ratio, and further assuming that the variable inductance L2 of the second inductor 9 can be adjusted down to substantially zero (L2*min*=0), the total inductance of the second branch 6 can be adjusted (in discrete steps or substantially continuously) from substantially 0 to a maximum total inductance corresponding to the sum of all inductances of the inductors forming part of the second branch 6, i.e. L2*max*+L3+L4+L5 etc.

According to a further variant, which can be based on any of the above embodiments or variants, the second and/or any further inductors (together with any associated bypass circuitry) are included in the first branch 5, rather than the second branch 6.

Figure 5:
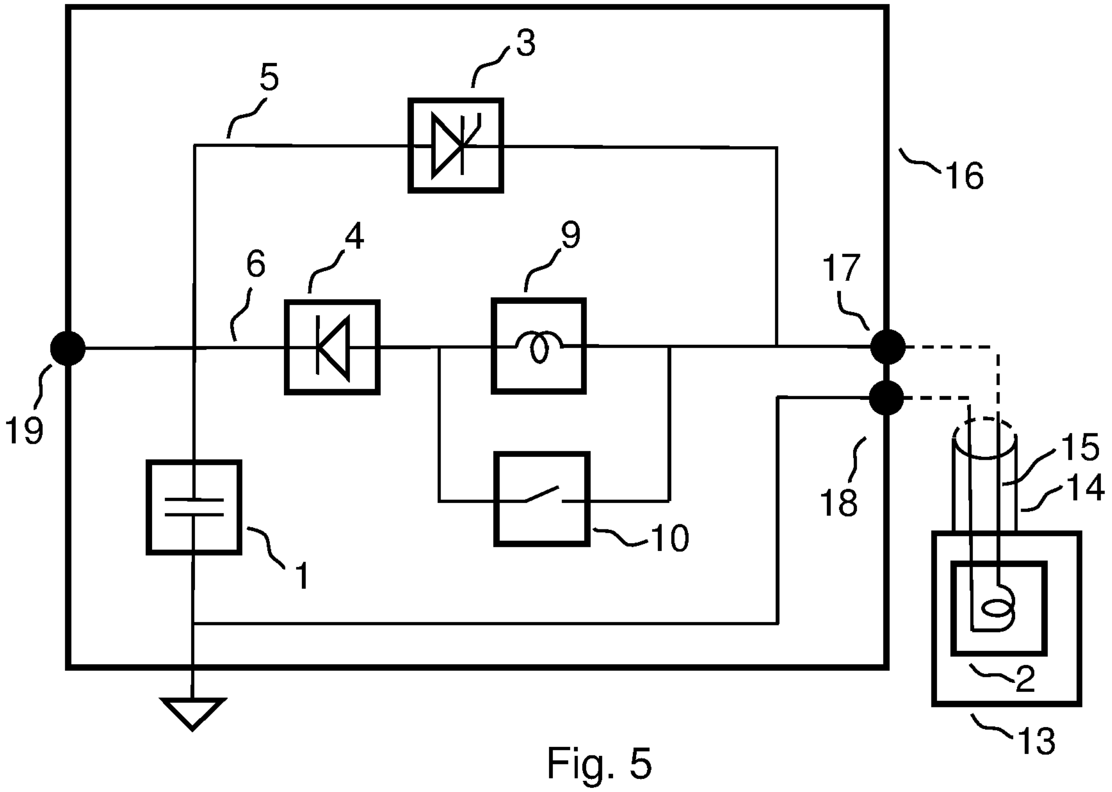

FIG. 5 schematically shows an apparatus for generating a magnetic field in accordance with an embodiment of the present disclosure. This is closely based on the embodiment shown in FIG. 3. However, the charging circuit shown in FIG. 3 is not shown in FIG. 5. Instead, FIG. 5 shows the capacitor 1 and the first and second branches 5 and 6 incorporated in a housing or cabinet 16 (electrically insulated from electric components and circuitry accommodated by cabinet 16). A terminal 19 for connection to an external charging circuit is provided on the cabinet 16 for the purpose of charging the capacitor 1. In a variant, the charging circuit, for example as shown in FIG. 3, can also be incorporated in the cabinet 16.

Cabinet 16 is provided with two further terminals, 17 and 18. Terminal 17 is connected to the first branch 5 and second branch 6, whereas terminal 18 is connected to a common ground potential. In the embodiment shown in FIG. 5, terminal 18 is connected to the ground connection for the capacitor 1 via a line running within the cabinet 16.

FIG. 5 shows the first inductor 2 as a separate entity from cabinet 16 and its contents. The first inductor 2 is accommodated in a casing 13, which is attached to a conduit 14. Conduit 14 accommodates a cable 15, which is electrically connected to the first inductor 2, in particular to at least one set of turns of inductor 2, and which can be connected to the terminal 17 as indicated by a dashed line. In the embodiment shown in FIG. 5, the inductor 2 can also be connected, via a second cable, to the ground terminal 18 on cabinet 16.

As a variant of the embodiment shown in FIG. 5, the first inductor 2 could be connected to a ground potential via a separate line, i.e. not via the cabinet 16. In this case, the ground terminal 18 and the internal connection to ground could be omitted.

In further variants, features of the embodiment shown in FIG. 5 can be combined with the embodiments shown in FIGS. 2 and 4 or any variants described herein. Further, in any of the above embodiments or variants, any or all connections to ground could be omitted and replaced by an electrical connection between the different portions of the circuit. For example, in FIG. 2, the three connections to ground (triangles towards the bottom of the figure) could be replaced by an interconnection so that the (in FIG. 2 lower side of) capacitor 1, first inductor 2 and voltage source 7 are electrically connected.

In any of the above embodiments or variants, the polarities of the individual components can be reversed so that, for example, the negative terminal of the voltage source 7 is connected, via the switching device 8, to the first branch 5, second branch 6 and capacitor 1. The polarities of the thyristor 3 and the diode 4 would then also be reversed. Further, as has already been mentioned, the inventor has appreciated that the components and interconnections described in connection with the present disclosure are not "ideal" in the electrical sense. Enabled by the present disclosure, one skilled in the art will be able to make appropriate adjustments to allow for this. This applies in particular, but not exclusively, to the variant described above in which inductors having inductances according to a ratio of 1:1:2:4:8 etc. can be used. Appropriate adjustments can be made so as to take parasitic inductances into account, for example.

Figure 6:
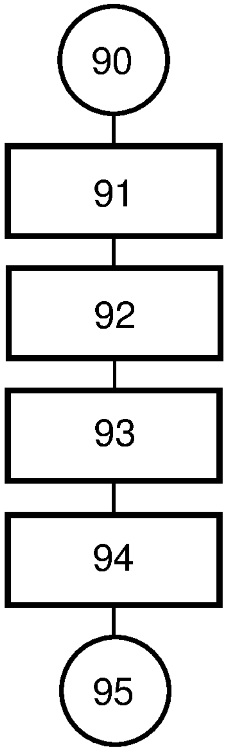
FIG. 6 shows a flowchart illustrating a method in accordance with an embodiment of the present disclosure.

FIG. 6 shows a flowchart illustrating a method in accordance with an embodiment of the present disclosure. After the start 90 of the method, any one of the apparatuses described above is provided (91). Electrical energy is then (92) stored in the electric storage device, in particular the capacitor 1. Thereafter, the switching device 3, in particular the thyristor 3, is switched (93) into a conductive or "ON" state so as to electrically connect the electric storage device 1 to the first inductor 2. This enables electrical current to flow through the first branch 5 and through the first inductor 2, caused by the electrical energy stored by the electric storage device 1, thereby causing the first inductor 2 to generate a magnetic field. This current flow may represent a first half pulse or half wave. At the end of the first half pulse or half wave, electrical current is then enabled (94) to flow between the electric storage device 1 and the first inductor 2 through the second branch 6 via the electric component or assembly of electric components 4. This current flow may represent a second half pulse or half wave. Assuming the second and any further inductors 9, 11 are not bypassed or short-circuited, electrical current will also flow through the second and any further inductors 9, 11 during this second half pulse or half wave. At the end of the second half pulse or half wave, the method may end (95). Alternatively, the method or part thereof may be repeated. In particular, the switching device or thyristor 3 can again be switched (93) into the conductive or "ON" state etc. Electrical energy may also again be stored (92) in the electric storage device 1. In particular, the capacitor 1 may be recharged to its initial charging state, e.g. to compensate for dissipation of electrical energy in the apparatus.

Figure 7:
FIG. 7 shows a diagram in which the current through the first inductor is plotted over time, in accordance with an embodiment of the present disclosure.

FIG. 7 shows a diagram in which the current through the first inductor 2 is plotted over time, in accordance with an embodiment of the present disclosure. A circuit which might result in the diagram of FIG. 7 could be the circuit shown in FIG. 2, except that the second inductor 9 would be located in the first branch 5 (in series with the switching device 3), rather than the second branch 6. The first half pulse shown in FIG. 7 exhibits a slower rise and fall of the current through the first inductor 2 than the second half pulse. This is due to the higher total inductance during the first half pulse (total inductance=inductance of first inductor 2+inductance of second inductor 9) when compared with the total inductance during the second half pulse (total inductance=inductance of first inductor 2).

FIG. 8 schematically shows a circuit diagram of an apparatus for generating a magnetic field in accordance with an embodiment of the present disclosure. The circuit diagram shown in FIG. 8 is similar to that shown in FIG. 2. The above explanations regarding the device shown in FIG. 2 therefore also apply to the circuit diagram shown in FIG. 8 and will not be repeated here. Where elements shown in FIG. 8 have substantially the same function as elements shown in FIG. 2, these carry the same reference signs as in FIG. 2. Where elements shown in FIG. 8 are generally similar to elements shown in FIG. 2 but are different, for example in terms of their function or position within the circuit, these carry the reference signs as in FIG. 2 but increased by 300.

In contrast to the embodiment shown in FIG. 2, the second branch 6 does not include an additional inductor which does not (also) form part of the first branch 5. Instead, the circuit shown in FIG. 8 includes a second inductor 309 connected in series with the first inductor 2. Electrical current flowing between the first inductor 2 and the capacitor 1 will also flow through the second inductor 309, regardless of whether the current flows through the first branch 5 or the second branch 6. In other words, the second inductor 309 is not only connected in series with the first inductor 2 but also with each of the switching device 3 and the diode 4 (or, more precisely, in series with the parallel connection that comprises the switching device 3 and the diode 4). One could also say that the second inductor 309 forms part of both the first branch 5 and the second branch 6.

The total inductance of the (resonant) circuit between (and including) the capacitor 1 and the first inductor 2 corresponds to the sum of the inductances of the first inductor 2 and the second inductor 309 (as well as any other inductance, including parasitic inductances, that may be present in the circuit and which are not shown in FIG. 8). Accordingly, the frequency of this (resonant) circuit is different from the frequency of the (resonant) circuit shown in FIG. 1, i.e. if the second inductor 309 was not present. The frequency of the (resonant) circuit shown in FIG. 8 can therefore be influenced by selecting different values of inductance for the second inductor 309.

FIG. 9 schematically shows a circuit diagram of an apparatus for generating a magnetic field in accordance with an embodiment of the present disclosure. The embodiment shown in FIG. 9 is similar to that shown in FIG. 8, and the same explanations provided in connection with FIG. 8 also apply to the embodiment shown in FIG. 9. Like components carry like reference signs. FIG. 9 additionally shows circuitry for bypassing or short-circuiting the second inductor 309. This bypass circuitry is connected to the two terminals of the second inductor 309 and includes a further switching device 310 to enable the bypass circuitry to selectively bypass the second inductor 309. When the further switching device 310 is closed (or conductive), any electrical current flowing through the first inductor 2 will predominantly or (almost) exclusively flow through the bypass circuitry, thereby substantially preventing current from flowing through the second inductor 309. In this way, the total inductance of the (resonant) circuit between (and including) the capacitor 1 and the first inductor 2 can be changed between a maximum value (further switching device 310 open) and a minimum value (further switching device 310 closed). When the further switching device 310 is closed, the inductance of the (resonant) circuit may be similar to that of the corresponding circuit portion of FIG. 1 (i.e. as if the second inductor 309 was not present.

FIG. 10 schematically shows a circuit diagram of an apparatus for generating a magnetic field in accordance with an embodiment of the present disclosure. The embodiment shown in FIG. 10 is similar to that shown in FIG. 9, and the same explanations provided in connection with FIG. 9 also apply to the embodiment shown in FIG. 10. Like components carry like reference signs. FIG. 10 additionally shows a further inductor 311 connected in series with the first inductor 2 and the second inductor 309. Electrical current flowing between the first inductor 2 and the capacitor 1 will also flow through the further inductor 311, regardless of whether the current flows through the first branch 5 or the second branch 6. In other words, the further inductor 311 is not only connected in series with the first and second inductors 2, 309 but also with each of the switching device 3 and the diode 4 (or, more precisely, in series with the parallel connection that comprises the switching device 3 and the diode 4). The circuit diagram shown in FIG. 10 additionally includes further circuitry for bypassing or short-circuiting the further inductor 311. This further bypass circuitry is connected to the two terminals of the further inductor 311 and includes a further switching device 312 to enable the further bypass circuitry to selectively bypass the further inductor 311. When the further switching device 312 is closed (or conductive), any electrical current flowing through the first inductor 2 will predominantly or (almost) exclusively flow through the further bypass circuitry, thereby substantially preventing current from flowing through the further inductor 311. In this way, the total inductance of the resonant circuit can be varied.

Using the two further switching devices 310 and 312, the total inductance of the resonant circuit can be changed between a maximum value (both further switching devices 310 and 312 open or non-conductive) and a minimum value (both further switching devices 310 and 312 closed or conductive). When both further switching devices 310 and 312 are closed, the total inductance of the resonant circuit may be similar to that of the corresponding circuit portion of FIG. 1 (i.e. as if the second inductor 309 and the further inductor 311 was not present. When only one of the further switching devices 310 and 312 is closed and the other is open, only one of the second inductor 309 and the further inductor 311 will be bypassed, and accordingly the total inductance of the resonant circuit will be at an intermediate value between the minimum value and the maximum value.

According to a variant of the embodiment shown in FIG. 10, the bypass circuitry associated with either the second inductor 309 or the further inductor 311 can be omitted. The respective inductor will therefore be permanently connected in series with the first inductor 2, whereas the other of the second inductor 309 and the further inductor 311 (the bypass circuitry of which is not omitted) can selectively be bypassed using its associated bypass circuitry.

According to a further variant of the embodiment shown in FIG. 10, yet further inductors can be added in series with the first and second inductors 2, 309 and the further inductor 311 (and in series with the parallel connection that comprises the switching device 3 and the diode 4). Each of these yet further inductors may or may not have their associated bypass circuitry similar to the bypass circuitry associated with the second inductor 309 and the further inductor 311.

According to a variant of any of the embodiments described with reference to FIGS. 8, 9 and 10 (or any of the variants already explained above), any one or more of the second inductor 309, the further inductor 311 and the yet further inductors (if provided) may comprise inductors with a variable inductance. Details of inductors with a variable inductance have already been explained above.

In a further development of this variant, only one of the inductors (the second inductor 309, the further inductor 311 or the yet further inductors, if provided) is of variable inductance, for example the second inductor 309. Nevertheless, by suitable choice of the (maximum) inductance of the second inductor 309 and of the inductance of the further inductor 311 and, if provided, the yet further inductors, the total inductance of the resonant circuit can be adjustable over a relatively wide range, in particular in small steps or (substantially) continuously. In this further development, each of the (yet) further inductors is provided with associated bypass circuitry. The second inductor 309 of variable inductance may or may not be provided with associated bypass circuitry. If the inductances of the second inductor (L2) and of the further inductors (L3, L4, L5, L6 etc.) are chosen according to a ratio of 1:1:2:4:8 etc., the lowest value of total inductance of the resonant circuit can be achieved if the third inductor (of inductance L3) and any further inductors (of inductance L4, L5, L6 etc.) are bypassed and the variable inductance (L2) of the second inductor 309 is adjusted to a minimum value L2*min*. Then, by adjusting the variable inductance L2 of the second inductor 309 over its adjustable range to a maximum value L2*max*, the total inductance of the resonant circuit can be adjusted from L1+L2*min* to L1+L2*max* (with L1 being the inductance of the first inductor 2). If (only) the third inductor is not bypassed (and the fourth and any further inductors are bypassed), the total inductance of the resonant circuit can be adjusted from L1+L3+L2*min* to L1+L3+L2*max* by adjusting the variable inductance L2 of the second inductor 309 over its adjustable range. If (only) the fourth inductor is not bypassed (and the third, fifth and any further inductors are bypassed), the total inductance of the resonant circuit can be adjusted from L1+L4+L2*min* to L1+L4+L2*max*. The next adjustable range of the total inductance can be achieved by not bypassing the third and fourth inductor and bypassing the fifth and any further inductors, and so on. If the relative inductances of the second inductor 309 and of the further inductors are chosen according to the above ratio, and further assuming that the variable inductance L2 of the second inductor 309 can be adjusted down to substantially zero (L2*min*=0), the total inductance of the resonant circuit can be adjusted (in discrete steps or substantially continuously) from substantially L1 to a maximum total inductance corresponding to the sum of all inductances of the resonant circuit, i.e. L1+L2*max*+L3+L4+L5 etc.

According to a further variant, which can be based on any of the embodiments explained with reference to FIGS. 8 to 10 or their variants, further inductors (together with any associated bypass circuitry, if applicable) may additionally be included in the first branch 5 or the second branch 6, as explained with reference to FIGS. 2 to 4 or their variants.

FIG. 11 schematically shows an apparatus for generating a magnetic field in accordance with an embodiment of the present disclosure. This is closely based on the embodiment shown in FIG. 9. However, the charging circuit shown in FIG. 9 is not shown in FIG. 11. Instead, FIG. 11 shows the capacitor 1 and the first and second branches 5 and 6 incorporated in a housing or cabinet 16 (electrically insulated from electric components and circuitry accommodated by cabinet 16). A terminal 19 for connection to an external charging circuit is provided on the cabinet 16 for the purpose of charging the capacitor 1. In a variant, the charging circuit, for example as shown in FIG. 9, can also be incorporated in the cabinet 16.

Cabinet 16 is provided with two further terminals, 17 and 18. Terminal 17 is connected to the second inductor 309 (and its associated bypass circuitry) and, therethrough, also to first branch 5 and second branch 6, whereas terminal 18 is connected to a common ground potential. In the embodiment shown in FIG. 11, terminal 18 is connected to the ground connection for the capacitor 1 via a line running within the cabinet 16.

FIG. 11 shows the first inductor 2 as a separate entity from cabinet 16 and its contents. The first inductor 2 is accommodated in a casing 13, which is attached to a conduit 14. Conduit 14 accommodates a cable 15, which is electrically connected to the first inductor 2, in particular to at least one set of turns of inductor 2, and which can be connected to the terminal 17 as indicated by a dashed line. In the embodiment shown in FIG. 11, the inductor 2 can also be connected, via a second cable, to the ground terminal 18 on cabinet 16.

As a variant of the embodiment shown in FIG. 11, the first inductor 2 could be connected to a ground potential via a separate line, i.e. not via the cabinet 16. In this case, the ground terminal 18 and the internal connection to ground could be omitted.

In further variants, features of the embodiment shown in FIG. 11 can be combined with features of the embodiments shown in FIGS. 8 and 10 or any variants described herein. Further, in any of the above embodiments or variants, any or all connections to ground could be omitted and replaced by an electrical connection between the different portions of the circuit. For example, in FIG. 8, the three connections to ground (triangles towards the bottom of the figure) could be replaced by an interconnection so that the (in FIG. 8 lower side of) capacitor 1, first inductor 2 and voltage source 7 are electrically connected.

In any of the above embodiments or variants, the polarities of the individual components can be reversed so that, for example, the negative terminal of the voltage source 7 is connected, via the switching device 8, to the first branch 5, second branch 6 and capacitor 1. The polarities of the thyristor 3 and the diode 4 would then also be reversed. Further, as has already been mentioned, the inventor has appreciated that the components and interconnections described in connection with the present invention are not "ideal" in the electrical sense. Enabled by the present disclosure, one skilled in the art will be able to make appropriate adjustments to allow for this. This applies in particular, but not exclusively, to the variant described above in which inductors having inductances according to a ratio of 1:1:2:4:8 etc. can be used. Appropriate adjustments can be made so as to take parasitic inductances into account, for example.

In further variants of the embodiments shown in FIGS. 8 to 11 or their variants described above, the position (in the electrical sense) of the second inductor 309 (along with any associated bypass circuitry 310) and of the parallel connection comprising the first branch 5 and the second branch 6 can be reversed so that the second inductor 309 is connected between capacitor 1 and the parallel connection comprising the first branch 5 and the second branch 6. This may also apply to any further inductors. What matters, according to such variants, is that the capacitor 1, the parallel connection comprising the first branch 5 and the second branch 6, the first inductor 2, the second inductor 309 and any further inductors (such as inductor 311) are connected in series.

FIG. 12 shows a flowchart illustrating a method in accordance with an embodiment of the present disclosure. After the start 390 of the method, any one of the apparatuses described above with reference to FIGS. 8 to 11 or their variants is provided (391). Electrical energy is then (392) stored in the electric storage device, in particular the capacitor 1. Thereafter, the switching device 3, in particular the thyristor 3, is switched (393) into a conductive or "ON" state so as to electrically connect the electric storage device 1 to the first inductor 2. This enables electrical current to flow through the first branch 5 and through the second inductor 309 (if not bypassed), through the first inductor 2 and, if applicable, through any further inductors such as further inductor 311 (if not bypassed), caused by the electrical energy stored by the electric storage device 1, thereby causing the first inductor 2 to generate a magnetic field. This current flow may represent a first half pulse or half wave. At the end of the first half pulse or half wave, electrical current is then enabled (394) to flow between the electric storage device 1 and the first inductor 2 through the second branch 6 via the electric component or assembly of electric components 4 (as well as via the second and any further inductors 309, 311, if not bypassed). This current flow may represent a second half pulse or half wave. At the end of the second half pulse or half wave, the method may end (395). Alternatively, the method or part thereof may be repeated. In particular, the switching device or thyristor 3 can again be switched (393) into the conductive or "ON" state etc. Electrical energy may also again be stored (392) in the electric storage device 1. In particular, the capacitor 1 may be recharged to its initial charging state, e.g. to compensate for dissipation of electrical energy in the apparatus.

FIG. 13 shows a diagram in which the current through the first inductor 2 is plotted over time, in accordance with an embodiment of the present disclosure. A circuit which might result in the diagram of FIG. 13 could be the circuit shown in FIG. 9, whereby the further switching device 310 is initially open, i.e. during the first half pulse (so that current flowing through the first inductor 2 will also flow through the second inductor 309). At the end of the first half pulse, the further switching device 310 is closed so as to short-circuit or bypass the second inductor 309. The first half pulse shown in FIG. 13 exhibits a slower rise and fall of the current through the first inductor 2 than the second half pulse. This is due to the higher total inductance during the first half pulse (total inductance=inductance of first inductor 2+inductance of second inductor 309) when compared with the total inductance during the second half pulse (total inductance=inductance of first inductor 2).

FIG. 14 schematically shows a circuit diagram of an apparatus for generating a magnetic field in accordance with an embodiment of the present disclosure. The circuit diagram shown in FIG. 14 is similar to that shown in FIG. 2. The above explanations regarding the device shown in FIG. 2 therefore also apply to the circuit diagram shown in FIG. 14 and will not be repeated here. Where elements shown in FIG. 14 have substantially the same function as elements shown in FIG. 2, these carry the same reference signs as in FIG. 2. Where elements shown in FIG. 14 are generally similar to elements shown in FIG. 2 but are different, for example in terms of their function or position within the circuit, these carry the reference signs as in FIG. 2 but increased by 400.

In contrast to the embodiment shown in FIG. 2, the second branch 6 does not include an additional inductor which does not (also) form part of the first branch 5. Instead, the circuit shown in FIG. 14 includes a capacitor 401 of variable capacitance—at the same position within the circuit where FIG. 2 has a capacitor 1 (which capacitor 1, in FIG. 2, is not specified as having a variable capacitance).

Capacitor 401 can in principle be any type of capacitor with a variable capacitance (or in short: a variable capacitor). The symbol used in FIG. 14 for capacitor 401 may typically be used for one particular type of variable capacitor only, but it is to be understood that this symbol is intended to represent any type of variable capacitor, including mechanically controlled variable capacitors and electrically controlled variable capacitors.

Whilst capacitor 401 is a single capacitor, it can nevertheless be regarded as a capacitor arrangement 420. Further examples of capacitor arrangements comprising several capacitors will be explained with reference to FIGS. 15 to 18.

When the capacitance of capacitor 401 of FIG. 14 is varied, this varies the resonant frequency of the resonant circuit of which capacitor 401 forms a part, i.e. the resonant circuit comprising capacitor 401, (first) inductor 2 and connecting circuitry (branches 5 and/or 6) connecting these. Accordingly, if the circuit of FIG. 14 is operated in a pulsed manner, the pulse duration is varied as well.

FIG. 15 schematically shows a circuit diagram of an apparatus for generating a magnetic field in accordance with an embodiment of the present disclosure. The embodiment shown in FIG. 15 is similar to that shown in FIG. 14, and the same explanations provided in connection with FIG. 14 also apply to the embodiment shown in FIG. 15. Like components carry like reference signs. FIG. 15 additionally shows a further capacitor 421 connected in parallel to capacitor 401. Accordingly, the capacitor arrangement 420 of FIG. 15 comprises the capacitors 401 and 421. The (total) capacitance of capacitor arrangement 420 of FIG. 15 corresponds (or is similar) to the sum of the (individual) capacitances of capacitors 401 and 421.

Capacitor 421 is shown as a variable capacitor, and the comments above regarding the symbol used for capacitor 401 also apply to capacitor 421. However, the further capacitor 421 does not necessarily need to have a variable capacitance—it could also have a fixed capacitance.

Varying the capacitance of capacitor 401 and/or capacitor 421 will vary the total capacitance of capacitor arrangement 420 and hence the resonant frequency of the resonant circuit of which the capacitor arrangement 420 forms a part.

In variants of the embodiment shown in FIG. 15, further capacitors, in particular capacitors of variable capacitance, can additionally be provided and connected in parallel to capacitor 401.

FIG. 16 schematically shows a circuit diagram of an apparatus for generating a magnetic field in accordance with an embodiment of the present disclosure. The embodiment shown in FIG. 16 is similar to that shown in FIG. 15, and the same explanations provided in connection with FIG. 15 also apply to the embodiment shown in FIG. 16. Like components carry like reference signs. FIG. 16 additionally shows a further switch or switching device 422 connected in series with the further capacitor 421. The further switching device 422 selectively establishes or interrupts an electrical connection between further capacitor 421 and capacitor 401. When the further switching device 422 is closed (or conductive), the further capacitor 421 is connected in parallel to capacitor 401 and the (total) capacitance of capacitor arrangement 420 of FIG. 16 corresponds (or is similar) to the sum of the (individual) capacitances of capacitors 401 and 421. When the further switching device 422 is open (or non-conductive), the (total) capacitance of capacitor arrangement 420 of FIG. 16 corresponds (or is similar) to the (individual) capacitance of capacitor 401—as if the further capacitor 421 was not present. In this way, by opening or closing the further switching device 422 (or selectively causing it to be non-conductive or conductive), the resonant frequency of the resonant circuit of which the capacitor arrangement 420 forms a part can be varied.

In this embodiment, the further capacitor 421 may have a fixed capacitance (as shown) or may alternatively have a variable capacitance. Further, in a variant, the position of the further capacitor and the further switching device 422 within the circuit is swapped so that the further switching device 422 is placed between the further capacitor 421 and ground. Electrically, this makes no significant difference and therefore this variant will be considered to be equivalent to the embodiment shown in FIG. 16.

In the embodiment of FIG. 16, if the (maximum) capacitance of capacitor 401 and the (maximum) capacitance of the further capacitor 421 are chosen to be the same, then the total capacitance of the capacitor arrangement 420 can be varied over a range from the minimum capacitance of capacitor 401 up to the sum of the (maximum) capacitances of capacitors 401 and 421. For example, if capacitor 401 can be adjusted between 0 μF and 100 μF and capacitor 421 has a (fixed) capacitance of 100 μF, then the total capacitance of the capacitor arrangement 420 can be varied between 0 μF and 100 μF when switching device 422 is open (or non-conductive) and between 100 μF and 200 μF when switching device 422 is closed (or conductive). If capacitor 401 is continuously variable between 0 μF and 100 μF, then the total capacitance of the capacitor arrangement 420 of this example can be varied continuously between 0 μF and 200 μF.

In another example, if capacitor 401 can be adjusted between 0 μF and 100 μF and capacitor 421 has a (fixed) capacitance of 300 μF, then the total capacitance of the capacitor arrangement 420 can be varied between 0 μF and 100 μF when switching device 422 is open (or non-conductive) and between 300 μF and 400 μF when switching device 422 is closed (or conductive).

FIG. 17 schematically shows a circuit diagram of an apparatus for generating a magnetic field in accordance with an embodiment of the present disclosure. The embodiment shown in FIG. 17 is similar to that shown in FIG. 16, and the same explanations provided in connection with FIG. 16 also apply to the embodiment shown in FIG. 17. Like components carry like reference signs. FIG. 17 additionally shows a (yet) further capacitor 423 connected in parallel to capacitor 401 (and in parallel to further capacitor 421). Accordingly, the capacitor arrangement 420 of FIG. 17 comprises the capacitors 401, 421 and 423. FIG. 17 also shows a (yet) further switch or switching device 424 connected in series with the further capacitor 423. The further switching device 424 selectively establishes or interrupts an electrical connection between further capacitor 423 and capacitor 401 (and further capacitor 421). When the further switching devices 422 and 424 are closed (or conductive), the further capacitors 421 and 423 are connected in parallel to capacitor 401 and the (total) capacitance of capacitor arrangement 420 of FIG. 17 corresponds (or is similar) to the sum of the (individual) capacitances of capacitors 401, 421 and 423. When the further switching devices 422 and 424 are open (or non-conductive), the (total) capacitance of capacitor arrangement 420 of FIG. 17 corresponds (or is similar) to the (individual) capacitance of capacitor 401—as if the further capacitors 421 and 423 were not present. The same applies, mutatis mutandis, if only one of the switching devices 422 and 424 is closed (or conductive) and the other is open (or non-conductive). In this way, by selectively opening or closing the further switching devices 422 and/or 424 (or selectively causing them to be non-conductive or conductive), the resonant frequency of the resonant circuit of which the capacitor arrangement 420 forms a part can be varied.

According to further variants, the capacitor arrangement 420 may be expanded by adding yet further capacitors and connecting these in parallel to capacitor 401. These yet further capacitors may have a variable capacitance or a fixed capacitance. In addition, yet further switching devices may be connected in series with yet further capacitors, similar to what is shown in FIG. 17.

In a further development of this variant, only one of the capacitors (the capacitor 401) is of variable capacitance—similar to what is shown in FIG. 17, but with yet further capacitors (and their associated yet further switching devices) connected in parallel to capacitor 401. Nevertheless, by suitable choice of the (maximum) capacitance of the capacitor 401 and of the capacitances of the further capacitors 421 and 423 and the yet further capacitors, the total capacitance of the capacitor arrangement and hence the total capacitance of the resonant circuit (and therefore also the resonant frequency of the resonant circuit) can be adjustable over a relatively wide range, in particular in small steps or (substantially) continuously. If the (maximum) capacitance $C1$ of the capacitor 401 and the capacitances $C2$, $C3$ of the further capacitors 421 and 423 and of the yet further capacitors ($Cm$, where $m=4, 5, 6 \ldots$) are chosen according to a ratio of 1:1:2:4:8 etc., the lowest value of total capacitance of the capacitor arrangement 420 can be achieved if all of the further switching devices 422, 424 and yet further switching devices are open or non-conductive and the variable capacitance $C1$ of the capacitor 401 is adjusted to a minimum value $C1_{min}$. Then, by adjusting the variable capacitance $C1$ of the capacitor 401 over its adjustable range to a maximum value $C1_{max}$, the total capacitance of the capacitor arrangement 420 can be adjusted from $C1_{min}$ to $C1_{max}$. If (only) the further switching device 422 is closed or conductive (and all other (yet) further switching devices 424 etc. are open or non-conductive), the total capacitance of the capacitor arrangement 420 can be adjusted from $C2+C1_{min}$ to $C2+C1_{max}$ by adjusting the variable capacitance C1 of the capacitor 401 over its adjustable range. The next adjustable range of the total capacitance of the capacitor arrangement 420 can be achieved by further switching device 424 being closed or conductive and switching device 422 and all other yet further switching devices being open or non-conductive, and so on. If the relative capacitances are chosen according to the above ratio, and further assuming that the variable capacitance C1 of the capacitor 401 can be adjusted down to substantially zero ($C1_{min}$=0 μF), the total capacitance of the capacitor arrangement 420 can be adjusted (in discrete steps or substantially continuously) from substantially 0 μF to a maximum total capacitance corresponding to the sum of all capacitances of the capacitor arrangement 420, i.e. $C1_{max}$+C2+C3+C4 etc.

According to a further variant, which can be based on any of the embodiments explained with reference to FIGS. 14 to 17 or their variants, further inductors (together with any associated bypass circuitry, if applicable) may additionally be included in the first branch 5 or the second branch 6, as explained with reference to FIGS. 2 to 4 or their variants, and/or in series with the first inductor 2, as explained with reference to FIGS. 8 to 10 or their variants.

FIG. 18 schematically shows an apparatus for generating a magnetic field in accordance with an embodiment of the present disclosure. This is closely based on the embodiment shown in FIG. 17. However, the charging circuit shown in FIG. 17 is not shown in FIG. 18. Instead, FIG. 18 shows the capacitor arrangement 420 and the first and second branches 5 and 6 incorporated in a housing or cabinet 16 (electrically insulated from electric components and circuitry accommodated by cabinet 16). A terminal 19 for connection to an external charging circuit is provided on the cabinet 16 for the purpose of charging the capacitor arrangement 420. In a variant, the charging circuit, for example as shown in FIG. 17, can also be incorporated in the cabinet 16.

Cabinet 16 is provided with two further terminals, 17 and 18. Terminal 17 is connected to the first branch 5 and the second branch 6, whereas terminal 18 is connected to a common ground potential. In the embodiment shown in FIG. 18, terminal 18 is connected to the ground connection for the capacitor arrangement 420 via a line running within the cabinet 16.

FIG. 18 shows the first inductor 2 as a separate entity from cabinet 16 and its contents. The first inductor 2 is accommodated in a casing 13, which is attached to a conduit 14. Conduit 14 accommodates a cable 15, which is electrically connected to the first inductor 2, in particular to at least one set of turns of inductor 2, and which can be connected to the terminal 17 as indicated by a dashed line. In the embodiment shown in FIG. 18, the inductor 2 can also be connected, via a second cable, to the ground terminal 18 on cabinet 16.

As a variant of the embodiment shown in FIG. 18, the first inductor 2 could be connected to ground via a separate line, i.e. not via the cabinet 16. In this case, the ground terminal 18 and the internal connection to ground could be omitted.

In further variants, features of the embodiment shown in FIG. 18 can be combined with features of the embodiments shown in FIGS. 14 to 16 or any variants described herein. Further, in any of the above embodiments or variants, any or all connections to ground could be omitted and replaced by an electrical connection between the different portions of the circuit. For example, in FIGS. 14 to 17, the three connections to ground (triangles towards the bottom of the figures) could be replaced by an interconnection so that the (in FIGS. 14 to 17 lower side of the) capacitors of the capacitor arrangement 420, first inductor 2 and voltage source 7 are electrically connected.

In any of the above embodiments or variants, the polarities of the individual components can be reversed so that, for example, the negative terminal of the voltage source 7 is connected, via the switching device 8, to the first branch 5, second branch 6 and capacitor arrangement 420. The polarities of the thyristor 3 and the diode 4 would then also be reversed. Further, as has already been mentioned, the inventor has appreciated that the components and interconnections described in connection with the present invention are not "ideal" in the electrical sense. Enabled by the present disclosure, one skilled in the art will be able to make appropriate adjustments to allow for this. This applies in particular, but not exclusively, to the variant described above in which capacitors having capacitances according to a ratio of 1:1:2:4:8 etc. can be used. Appropriate adjustments can be made so as to take parasitic capacitances into account, for example.

FIG. 19 shows a flowchart illustrating a method in accordance with an embodiment of the present disclosure. After the start 490 of the method, any one of the apparatuses described above with reference to FIGS. 14 to 18 or their variants is provided (491). Electrical energy is then (492) stored in the capacitor arrangement 420, in particular the capacitor 401. Thereafter, the switching device 3, in particular the thyristor 3, is switched (493) into a conductive or "ON" state so as to electrically connect the capacitor arrangement 420 to the first inductor 2. This enables electrical current to flow through the first branch 5 and through the first inductor 2, caused by the electrical energy stored by the capacitor arrangement 420, thereby causing the first inductor 2 to generate a magnetic field. This current flow may represent a first half pulse or half wave. At the end of the first half pulse or half wave, electrical current is then enabled (494) to flow between the capacitor arrangement 420 and the first inductor 2 through the second branch 6 via the electric component or assembly of electric components 4. This current flow may represent a second half pulse or half wave. At the end of the second half pulse or half wave, the method may end (495). Alternatively, the method or part thereof may be repeated. In particular, the switching device or thyristor 3 can again be switched (493) into the conductive or "ON" state etc. Electrical energy may also again be stored (492) in the capacitor arrangement 420. In particular, the capacitor arrangement 420 may be recharged to its initial charging state, e.g. to compensate for dissipation of electrical energy in the apparatus.

As an optional, additional step (not shown in FIG. 19), the capacitance of the capacitor arrangement 420 can be varied, as explained above, either during the first or second half pulse or between the first and second half pulse or between a first (full) pulse and the next pulse.

FIG. 20 shows a diagram in which the current through the first inductor 2 is plotted over time, in accordance with an embodiment of the present disclosure. A circuit which might result in the diagram of FIG. 20 could be the circuit shown in FIG. 14, whereby the capacitance of the capacitor 401 is initially at a first capacitance value, i.e. during the first half pulse 430. The first half pulse 430 has a corresponding first duration. At the end of the first half pulse 430, the capacitance of the capacitor 401 is changed to a second capacitance value, which is lower than the first capacitance value. This increases the resonant frequency of the resonant circuit of which the capacitor 401 forms a part. Accordingly, the second half pulse 431 has a second duration, which is shorter than the first duration (of the first half pulse 430).

FIG. 21 schematically shows a circuit diagram of an apparatus for generating a magnetic field in accordance with an embodiment of the present disclosure. The circuit diagram shown in FIG. 21 is similar to that shown in FIG. 2 and other figures. The above explanations regarding the device shown in FIG. 2 (and other figures) therefore also apply to the circuit diagram shown in FIG. 21 and will not be repeated here. Where elements shown in FIG. 21 have substantially the same function as elements shown in FIG. 2 and other figures, these carry the same reference signs as in FIG. 2 (and in other figures). Where elements shown in FIG. 21 are generally similar to elements shown in FIG. 2 but are different, for example in terms of their function or position within the circuit, these carry the reference signs as in FIG. 2 but increased by 500.

In contrast to the embodiment shown in FIG. 2, the second branch 6 of FIG. 21 does not include an additional inductor which does not (also) form part of the first branch 5. Further, whilst the second branch 6 of the embodiment of FIG. 2 included an electric component 4 such as a diode, the embodiment of FIG. 21 includes a spark gap 542 and a resistor 543 (connected in series with the spark gap 542) in the second branch. In addition, the switching device 3 is a type of switching device which can not only be switched on (or transferred from the non-conductive state to the conductive state) but also off (or transferred from the conductive state to the non-conductive state). To this end, a (first) controller 540 is provided. Switching device 3 is controlled by controller 540 such that switching device 3 can be switched on and off at desired points in time. In particular, switching device 3 can be switched off at a point in time which does not coincide with the end of a first half pulse (assuming that the circuit shown in FIG. 21 is operated in a pulsed manner). Switching device 3 may, for example, comprise an insulated-gate bipolar transistor (IGBT), a field-effect transistor (FET), a metal-oxide-semiconductor field-effect transistor (MOSFET) or a gate turn-off thyristor (GTO-thyristor). The controller 540 may comprise analog circuitry or a microcontroller.

The operation of the circuit shown in FIG. 21 will now be explained, by way of example, with further reference to FIG. 24, which shows a flowchart illustrating a method in accordance with an embodiment of the present disclosure. The operation can be as follows: After the start 590 of the method, an apparatus with a circuit corresponding to the circuit shown in FIG. 21 (or any variants described herein) is provided (591). Electrical energy is then stored (592) in the capacitor arrangement 420—in FIG. 21 represented by capacitor 1. Thereafter, at a first point in time, the switching device 3 is switched (593), under the control of controller 540, into a conductive or "ON" state so as to electrically connect the capacitor arrangement 420 to the inductor 2. This enables electrical current to flow through the first branch 5 and through the inductor 2, caused by the electrical energy stored by the capacitor arrangement 420, thereby causing the inductor 2 to generate a magnetic field. This current flow may represent a first half pulse or half wave. However, the current flow may be interrupted at a selected second point in time. To this end, the switching device 3 is switched (594), under the control of controller 540, into the non-conductive or "OFF" state so as to electrically disconnect the capacitor arrangement 420 from the inductor 2. The second point in time can, for example, be during the first half pulse.

With the switching device 3 in the non-conductive state, electrical current can no longer flow through the switching device 3. However, the magnetic field, which has already been generated (by inductor 2), will resist its decay, which means that electrical current will continue to flow through inductor 2, resulting in a (relatively high) voltage in the first and second branch 5, 6. Eventually, this voltage is high enough to cause the spark gap 542 to become conductive (595), thereby enabling electrical current to flow between the capacitor arrangement 420 and the inductor 2 through the second branch 6 via resistor 543 and spark gap 542. The energy that was stored in the magnetic field is then at least partially dissipated in resistor 543. The method may then end (596). Alternatively, the method or part thereof may be repeated. In particular, the switching device 3 can again be switched (593) into the conductive or "ON" state etc. Electrical energy may also again be stored (592) in the capacitor arrangement 420. In particular, the capacitor arrangement 420 may be recharged to its initial charging state, e.g. to compensate for dissipation of electrical energy in the apparatus.

As per the above description with reference to FIGS. 21 and 24, the spark gap 542 may protect switching device 3 from damage or destruction, in particular if spark gap 542 is constructed such that it becomes conductive at a voltage U2, which is lower than a voltage U3 at which switching device 3 would suffer damage or be destroyed. On the other hand, spark gap 542 should not already become conductive at a voltage U1 to which the capacitor arrangement 420 is (to be) charged.

In variants (not specifically illustrated), other electrical circuit elements (some of which are normally classified as passive circuit elements) can be used instead of a spark gap 542, in particular a transient-voltage-suppression diode, a Zener diode, a Shockley diode, a triode for alternating current (TRIAC) or a thyristor, in particular in combination with trigger circuitry connected to, or forming part of, the second branch to trigger the thyristor.

FIG. 22 illustrates a variant of the embodiment of FIG. 21. Instead of a spark gap 542, an active electrical circuit element 503 or an arrangement of circuit elements is included in the second branch 6, in particular a switching element 503 controlled by analog circuitry or a microcontroller (or controlled by a second controller 541 comprising analog circuitry or a microcontroller). Using controller 541, a user can actively control the electrical circuit element 503, rather than the electrical circuit element 503 simply being allowed to become conductive or non-conductive depending on the voltage applied to its two terminals within the second branch 6.

FIG. 23 illustrates a further development of the embodiment of FIG. 22. In the embodiment of FIG. 23, the apparatus comprises a control unit 544 for controlling the first controller 540 and the second controller 541. To this end, the control unit 544 is connected to the first and the second controller 540, 541 (indicated by dashed lines). In this way, any, some or all of the points in time at which the switching device 3 and/or the switching element 503 are to be switched from the non-conductive state to the conductive state and vice versa can be controlled via control unit 544. In particular, the first and/or second points in time for switching the switching device 3 on and off can be selected via control unit 544. Similarly, third and/or fourth points in time for switching the switching element 503 on and off can be selected via control unit 544.

In order to enable a user to select any of the first to fourth points in time, the control unit 544 may have one or more dials 545 and/or any other (user) interface, such as a touchscreen 546. Control unit 544 may further comprise a processor/memory 547.

In a variant (not specifically illustrated), control unit 544 is connected directly to switching device 3 and/or switching element 503 in order to control these, in which case controllers 540 and/or 541 can be omitted.

In a further variant (not specifically illustrated), the apparatus may further have one or more detectors for taking measurements at one or more places within the circuit shown in FIG. 23, such as a voltage between the terminals of switching device 3 in the first branch 5 and/or a voltage between the terminals of switching element 503 in the second branch 6. These measurements can be communicated to control unit 544. Depending on the measurements taken, the control unit 544 can set any of the first to fourth points in time, for example in order to protect any elements of the circuit from damage or destruction, such as switching device 3 and/or switching element 503.

FIG. 23 shows a further development of the circuit. This further development involves a detector 548. Detector 548 is intended to detect a neural reaction or a cellular physiological reaction, in particular a muscle reaction, in body tissue—represented by a human arm 551 in FIG. 23, although detector 548 can be used in connection with any other body part of a human or animal. Detector 548 is also connected to control unit 544, as indicated by a dashed line. The operation of this further development will be explained with further reference to FIG. 25.

FIG. 25 shows several curves, in which current (I) through inductor 2 is plotted over time (t). Curve 549 follows the shape of a sine function and represents the current through inductor 102 of FIG. 1 under ideal conditions during a first half pulse. This therefore also represents the current through inductor 2 of FIG. 23 if switching device 3 was not switched into the non-conductive state during the first half pulse (i.e. if the second point in time was not before the end of the first half pulse).

When inductor 2 is applied to body tissue 551, the magnetic field generated by inductor 2 causes a current in the body tissue, as has been explained above. This current within the body tissue at least approximately follows the same shape as the current through inductor 2, albeit at a (significantly) reduced level and shifted in phase. The current within the body tissue can therefore be regarded as (approximately) proportional to the current through inductor 2 (but shifted in phase).

FIG. 25 shows four additional curves, 550*a* to 550*d*. These indicate the current through inductor 2 in cases where switching device 3 is switched into the non-conductive state before the end of the first half pulse, respectively at "second points in time" t1 to t4. The "first point in time" corresponds to the origin of the graph. In each case, the switching of switching device 3 into the non-conductive state results in a relatively steep drop in the current. That is, initially the current through inductor 2—after the first point in time (i.e. the origin), when switching device 3 is switched into the conductive state—follows the sine shape 549. After the "second points in time" t1 to t4, the current respectively continues along curves 550*a* to 550*d*. These further curves 550*a* to 550*d* therefore represent different scenarios, depending on when the switching device 3 is switched into the non-conductive state.

In the cases of curves 550*a* to 550*c*, the current reaches a maximum of I1 to I3, respectively. By varying the second point in time, in particular within the first quarter pulse (i.e. up to the time corresponding to the maximum of the sine shape 549), the maximum current that will be reached (through inductor 2 and also within the body tissue) can also be varied.

As mentioned, detector 548 is intended to detect a neural reaction or a cellular physiological reaction, in particular a muscle reaction in body tissue. If the current within the body tissue is sufficiently low, detector 548 will not detect any neural reaction or cellular physiological reaction, in particular a muscle reaction. In view of the graph shown in FIG. 25, this would correspond to a situation where the time interval between the first point in time (the origin) and the second point in time (e.g. t1) is very short. By increasing the time interval, the current within the body tissue will also increase, and eventually a neural reaction or a cellular physiological reaction, in particular a muscle reaction, will be detected by detector 548. For example, a neural reaction or cellular physiological reaction (but not a muscle reaction) might be detected if the time interval ends at t2, and a muscle reaction will be detected if the time interval ends at t3.

The detection result, i.e. whether a neural reaction or a cellular physiological reaction, in particular a muscle reaction, has been detected by detector 548 can be transmitted from detector 548 to control unit 544, in particular to processor/memory 547. Processor/memory 547 can process this information, as well as the information regarding the applicable time interval (or the second point in time) in order to determine the (shortest) time interval at which a neural reaction or cellular physiological reaction, in particular a muscle reaction, can be detected.

Curve 550*d* is less useful for determining the (shortest) time interval at which a neural reaction or cellular physiological reaction, in particular a muscle reaction, can be detected, since t4 is in the second quarter pulse, i.e. the maximum current (according to the sine function 549) has already been reached before t4.

In further variants, features of the embodiments shown in FIGS. 21 to 23 can be combined with features of the embodiments shown in FIGS. 2 to 4, 8 to 10, 14 to 17 or any variants described herein. Further, any of the above embodiments or variants can be adapted in a manner similar to what is shown in, and described in connection with, FIGS. 5, 11 and 18—in particular providing an apparatus according to FIGS. 21 to 23, but providing this apparatus with terminals 17, 18 and/or 19, for connection with an inductor 2 and/or an external charging circuit, respectively.

In any of the above embodiments or variants, the polarities of the individual components can be reversed so that, for example, the negative terminal of the voltage source 7 is connected, via the switching device 8, to the first branch 5, second branch 6 and capacitor arrangement 420.

FIG. 26 schematically shows a circuit diagram of an apparatus for generating a magnetic field in accordance with an embodiment of the present invention. The circuit diagram shown in FIG. 26 is similar to that shown in FIG. 2. The above explanations regarding the device shown in FIG. 2 therefore also apply to the circuit diagram shown in FIG. 26 and will not be repeated here. Where elements shown in FIG. 26 have substantially the same function as elements shown in FIG. 2, these carry the same reference signs as in FIG. 2. Where elements shown in FIG. 26 are generally similar to elements shown in FIG. 2 but are different, for example in terms of their function or position within the circuit, these carry the reference signs as in FIG. 2 but increased by 600.

In contrast to the embodiment shown in FIG. 2, the first inductor 2 is connected to, or forms part of, the first branch 5, but not the second branch 6. Similarly, a second inductor 609 is provided, which is connected to, or forms part of, the second branch 6, but not the first branch 5. The two branches 5, 6 are effectively separate, except that both are connected to the electric storage device 1 (again represented by a capacitor 1) and that they are both connected to a common ground potential (small triangles towards the bottom of the figure).

The first branch 5 also includes a switching device 3, and the above explanations as to possible types of switching devices also apply to the embodiment of FIG. 26. The second branch 6 also includes a switching device 603, and the above explanations as to possible types of switching devices also apply to switching device 603. The first and second switching devices 3, 603 may be of the same type, or may be of different types. In FIG. 26, the first switching device 3 and the second switching device 603 are shown as thyristors, by way of example. The polarity of the first switching device 3 is such that it allows current to flow substantially in only one direction, this representing a first current direction of current flow with respect to the electric storage device 1. The polarity of the second switching device 603 is such that it allows current to flow substantially in only one direction, this representing a second current direction of current flow with respect to the electric storage device 1. The second current direction of current flow with respect to the electric storage device 1 is opposite the first current direction.

The operation of the circuit shown in FIG. 26 will now be described, by way of example, with further reference to FIGS. 30 and 31. FIG. 30 shows a graph in which the current (I) through the first inductor 2 and the second inductor 609 is plotted over time (t). The graph of FIG. 30 can also be regarded as the current between the electric storage device 1 and the point where the first and second branches 5, 6 are connected. FIG. 31 shows a flowchart illustrating a method in accordance with an embodiment of the present invention. The operation can be as follows. After the start 690 of the method, an apparatus with a circuit corresponding to the circuit shown in FIG. 26 (or any variants described herein) is provided (691). Electrical energy is then stored (692) in the electric storage device 1. Thereafter, at a first point in time t1, the switching device 3 is switched (693) into a conductive or "ON" state, for example under the control of a suitable controller (such as a controller described herein in connection with other embodiments), so as to electrically connect the electric storage device 1 to the first inductor 2. This enables electrical current to flow through the first branch 5 and through the first inductor 2, caused by the electrical energy stored by the electric storage device 1, thereby causing the first inductor 2 to generate a first magnetic field. This current flow may represent a first half pulse or half wave 620.

At the end of the first half pulse 620, i.e. at a second point in time t2, the first magnetic field generated by first inductor 2 has essentially reduced to zero, and the electric storage device 1 has now reached its maximum charge, however of opposite polarity when compared with the initial state (just before t1). The absolute value of this maximum charge at t2 may be somewhat lower than the absolute value of the initial maximum charge (just before t1).

At a third point in time t3, the switching device 603 is switched (694) into a conductive or "ON" state, for example under the control of a suitable controller (such as a controller described herein in connection with other embodiments), so as to electrically connect the electric storage device 1 to the second inductor 609. This enables electrical current to flow through the second branch 6 and through the second inductor 609, caused by the electrical energy stored by the electric storage device 1, thereby causing the second inductor 609 to generate a second magnetic field. This current flow may represent a second half pulse or half wave 630.

At the end of the second half pulse 630, i.e. at a fourth point in time t4, the second magnetic field generated by second inductor 609 has essentially reduced to zero, and the electric storage device 1 has now reached its maximum charge, of the same polarity as during the initial state just before t1 (albeit at a somewhat reduced level, assuming that some losses of energy have occurred in the apparatus between t1 and t4). The method may then end (695). Alternatively, the method or part thereof may be repeated. In particular, the first switching device 3 can again be switched (693) into the conductive or "ON" state etc. Electrical energy may also again be stored (692) in the electric storage device 1. In particular, the capacitor 1 may be recharged to its initial charging state, e.g. to compensate for dissipation of electrical energy in the apparatus.

As will be appreciated from the above description, the two half pulses 620, 630 shown in FIG. 30 relate to different inductors, 2 and 609, respectively. While current flows through the first inductor 2 between t1 and t2, (substantially) no current flows through the second inductor 609. While current flows through the second inductor 609 between t3 and t4, (substantially) no current flows through the first inductor 2. Further, it will be appreciated from FIG. 30 and the above description that the delay between t2 and t3 can be chosen, in particular substantially freely, in particular by a user or manufacturer. In particular, the delay between t2 and t3 may be longer or shorter than the time interval between t1 and t2, or may be of the same duration. The two points in time t2 and t3 may also be selected such that they (substantially) coincide.

As will also be appreciated, the first and second inductances respectively of the first and second inductors 2, 609 may or may not be the same. In the example of FIG. 30, the second inductance of the second inductor 609 is smaller than the first inductance of the first inductor 2. Accordingly, the time between t3 and t4 is shorter than the time between t1 and t2.

FIG. 27 schematically shows an apparatus for generating a magnetic field in accordance with an embodiment of the present invention. This is closely based on the embodiment shown in FIG. 26. FIG. 27 shows the capacitor 1, the charging circuit comprising a source of electrical energy 7 and a switching device 8, as well as (a portion of) first and second branches 5 and 6 with first and second switching devices 3, 603 incorporated in a housing or cabinet 16 (electrically insulated from electric components and circuitry accommodated by cabinet 16). First inductor 2 is accommodated in a first casing 13. Second inductor 609 is accommodated in a second casing 613. The first casing 13 is movable independently from the second casing 613. Both are also movable with respect to cabinet 16 and may be electrically connected to the remainder of the circuit by flexible cables.

FIG. 28 schematically shows an apparatus for generating a magnetic field in accordance with an embodiment of the present invention. This is closely based on the embodiment shown in FIG. 27. However, in contrast to the embodiment of FIG. 27, both inductors 2, 609 are accommodated in the same casing 13 and are therefore not movable with respect to one another. The casing 13 may be movable with respect to cabinet 16. The first and second inductors 2, 609 may again be electrically connected to the remainder of the circuit by flexible cables. The cables may, for example, be arranged in a single conduit (not shown).

FIG. 29 schematically shows an apparatus for generating a magnetic field in accordance with an embodiment of the present invention. This is closely based on the embodiment shown in FIG. 28. However, in contrast to the embodiment of FIG. 28, the first and second inductors 2, 609, as well as the casing 13 in which they are accommodated, are provided as a separate unit for connection to cabinet 16. To this end, cabinet 16 is provided with a number of terminals. In the example shown in FIG. 29, there are four such terminals: terminals 17, 18 for electrical connection to first inductor 2, and terminals 617, 618 for electrical connection to second inductor 609. Depending on the construction of the first and second inductors 2, 609 and any cable(s) 15 connecting the first and second inductors 2, 609 to the remainder of the circuit, a different number of terminals may be provided on the cabinet 16. FIG. 29 also shows a conduit 14 in which the cables 15 may be arranged.

Within cabinet 16, terminal 17 is connected to the first switching device 3, and terminal 18 is connected to the ground connection for the capacitor 1 via a line running within cabinet 16. Similarly, terminal 617 is connected to the second switching device 603, and terminal 618 is again connected to the ground connection for the capacitor 1.

Whilst FIG. 29 shows the first and second inductors 2, 609 accommodated in the same casing 13, they may also be accommodated in separate casings and may be movable with respect to one another, similar to the embodiment of FIG. 27.

In variants of the embodiments of FIGS. 27 to 29, the charging circuit (comprising the source of electrical energy 7 and the switching device 8) or portions thereof may be provided separately (i.e. not within cabinet 16), for example as shown in FIGS. 5, 11 and 18, in which case cabinet 16 is provided with a further terminal 19 for connection to the external charging circuit.

In further variants, features of the embodiments shown in FIGS. 26 to 29 can be combined with features of the embodiments shown in FIGS. 2 to 5, 8 to 11, 14 to 18 and 21 to 23 or any variants described herein.

In any of the above embodiments or variants, the polarities of the individual components can be reversed so that, for example, the negative terminal of the voltage source 7 is connected, via the switching device 8, to the first branch 5 and the second branch 6. The polarities of the switching devices 3, 603 could then also be reversed—or they could remain the same, in which case the two branches 5, 6 and the two inductors 2, 609 swap their functions.

While at least one example embodiment of the present invention has been described above, it has to be noted that a great number of variations thereto exist. Furthermore, it is to be appreciated that the described example embodiments only illustrate non-limiting examples of how the present invention can be implemented and that it is not intended to limit the scope, the application or the configuration of the apparatuses and methods described herein. Rather, the preceding description will provide the person skilled in the art with instructions for implementing at least one example embodiment of the invention, whereby it has to be understood that various changes in the functionality and the arrangement of the elements of the example embodiment can be made without deviating from the subject-matter defined by the appended claims and their legal equivalents.

LIST OF REFERENCE SIGNS

1 electric storage device, capacitor
2 first inductor, set of turns
3 switching device, thyristor
4 electric component or assembly of electric components, diode
5 first branch (of connecting circuitry)
6 second branch (of connecting circuitry)
7 source of electrical energy, voltage source
8 switch, switching device, switching circuitry
9 second inductor
10 bypass circuitry
11 further inductor
12 further bypass circuitry
13 casing
14 conduit
15 cable
16 housing, cabinet
17-19 terminals
90-95 method steps
101 capacitor
102 inductor
103 thyristor
104 diode
105 first branch
106 second branch
107 voltage source
108 switch
200 first half pulse
210 second half pulse
309 second inductor
310 bypass circuitry
311 further inductor
312 further bypass circuitry
320 first half pulse
330 second half pulse
390-395 method steps
401 (first) variable capacitor
420 capacitor arrangement
421, 423 further capacitor (optionally: variable)
422, 424 further switching devices
430 first half pulse
431 second half pulse
490-495 method steps
503 switching device
540 (first) controller
541 (second) controller
542 spark gap
543 resistor
544 control unit
545 dial/interface
546 touch screen/interface
547 processor/memory device
548 detector
549 electrical current (half pulse)
550*a-d* electrical current
551 body part
590-596 method steps
603 switching device, thyristor
609 second inductor
613 casing
617, 618 terminals
620 first half pulse

630 second half pulse
690-695 method steps

The invention claimed is:

1. An apparatus for generating a magnetic field for application to body tissue, the apparatus comprising:

an electric storage device configured to store electrical energy;

a first inductor configured to generate a first magnetic field for application to the body tissue;

a second inductor configured to generate a second magnetic field;

connecting circuitry between the electric storage device and the first and second inductors, wherein the connecting circuitry comprises a first branch between the electric storage device and the first inductor and a second branch between the electric storage device and the second inductor;

a first switch, wherein the first switch forms part of the first branch, wherein the first switch is configured to electrically connect the electric storage device to the first inductor to enable electrical current to flow through the first branch and through the first inductor, due to the electrical energy stored by the electric storage device, and configured to cause the first inductor to generate the first magnetic field, wherein the electrical current flowing through the first branch represents a first current direction of current flow with respect to the electric storage device; and a second switch, wherein the second switch forms part of the second branch, wherein the second switch is configured to electrically connect the electric storage device to the second inductor to enable electrical current to flow through the second branch and through the second inductor, due to the electrical energy stored by the electric storage device, and configured to cause the second inductor to generate the second magnetic field, wherein the electrical current flowing through the second branch represents a second current direction of current flow with respect to the electric storage device, wherein the second current direction of current flow is opposite the first current direction of current flow, wherein the apparatus is configured for operation in a pulsed manner, wherein the electrical current that flows through the first branch during the pulsed manner of operation of the apparatus represents a first half pulse and wherein the electrical current that flows through the second branch during the pulsed manner of operation of the apparatus represents a second half pulse, the first half pulse and the second half pulse together forming a pulse.

2. The apparatus according to claim 1, wherein the first and second inductors are not connected in series.

3. The apparatus according to claim 1, wherein the first switch is configured to enable current flow with respect to the electric storage device only in the first current direction; and wherein the second switch is configured to enable current flow with respect to the electric storage device only in the second current direction.

4. The apparatus according to claim 1, wherein the second inductor is configured in a manner that the second magnetic field is also for application to the body tissue or other body tissue.

5. The apparatus according to claim 1, wherein the first inductor comprises at least a first set of turns, wherein the first inductor is disposed within a first casing connected to a first conduit through which extends at least a first cable for supplying electrical power to the first set of turns, and wherein the second inductor is not disposed within said first casing.

6. The apparatus according to claim 5, wherein the second inductor comprises at least a second set of turns, wherein the second inductor is disposed within a second casing connected to a second conduit through which extends at least a second cable for supplying electrical power to the second set of turns, and wherein the first inductor is not disposed within said second casing.

7. The apparatus according to claim 6, wherein the turns of the second set of turns are arranged in a manner that each turn generates a contribution towards the second magnetic field while the electrical current flows through the second inductor, wherein the contributions generated by each turn are superimposed in a positive manner.

8. The apparatus according to claim 5, wherein the turns of the first set of turns are arranged in a manner that each turn generates a contribution towards the first magnetic field while the electrical current flows through the first inductor, wherein the contributions generated by each turn are superimposed in a positive manner.

9. The apparatus according to claim 1, wherein the first inductor is wound on a first core and the second inductor is wound on a second core different from the first core.

10. The apparatus according to claim 1, wherein the first inductor and the second inductor are configured to move independently from each other.

11. The apparatus according to claim 1, wherein a first inductance of the first inductor and/or a second inductance of the second inductor is one of discretely variable and substantially continuously variable.

12. The apparatus according to claim 1, wherein the electric storage device comprises a pulse capacitor configured to be charged by a charging circuit.

13. A method comprising:

providing an apparatus comprising:

an electric storage device configured to store electrical energy;

a first inductor configured to generate a first magnetic field for application to body tissue;

a second inductor configured to generate a second magnetic field;

connecting circuitry between the electric storage device and the first and second inductors, wherein the connecting circuitry comprises a first branch between the electric storage device and the first inductor and a second branch between the electric storage device and the second inductor;

a first switch, wherein the first switch forms part of the first branch, wherein the first switch is configured to electrically connect the electric storage device to the first inductor to enable electrical current to flow through the first branch and through the first inductor, due to the electrical energy stored by the electric storage device, and configured to cause the first inductor to generate the first magnetic field, wherein the electrical current flowing through the first branch represents a first current direction of current flow with respect to the electric storage device; and a second switch, wherein the second switch forms part of the second branch, wherein the second switch is configured to electrically connect the electric storage device to the second inductor to enable electrical current to flow through the second branch and through the second inductor, due to the electrical energy stored by the electric storage device, and configured to cause the second inductor to generate the second magnetic field, wherein the electrical current flowing through the second branch represents a second current direction of current flow with respect to the electric storage device, wherein the second current direction of current flow is opposite the first current direction of current flow;

storing the electrical energy in the electric storage device;

switching the first switch in a manner as to electrically connect the electric storage device to the first inductor and enable electrical current to flow through the first branch and the first inductor in the first current direction of current flow with respect to the electric storage device, due to the electrical energy stored by the electric storage device, and configured to cause the first inductor to generate the first magnetic field; and switching the second switch in a manner as to electrically connect the electric storage device to the second inductor and enable electrical current to flow through the second branch and the second inductor in the second current direction of current flow with respect to the electric storage device, due to the electrical energy stored by the electric storage device, and configured to cause the second inductor to generate the second magnetic field, wherein the apparatus is operated in a pulsed manner, wherein the electrical current flowing through the first branch represents a first half pulse and wherein the electrical current flowing through the second branch represents a second half pulse, the first half pulse and the second half pulse together forming a pulse.

14. The method according to claim 13, wherein switching the second switch comprises switching the second switch after a delay after an end of the first half pulse.

15. The method according to claim 14, wherein the first half pulse has a first duration, wherein the delay is longer than the first duration.

16. The method according to claim 13, further comprising bringing the first inductor into proximity with the body tissue or other body tissue, or bringing the body tissue or the other body tissue into proximity with the first inductor, in a manner that the first magnetic field is present in the body tissue or the other body tissue.

17. The method according to claim 16, further comprising varying the first magnetic field in the body tissue or the other body tissue in a manner as to generate a voltage in the body tissue or the other body tissue or prompt a movement of charges in the body tissue or the other body tissue.

18. The method according to claim 17, wherein the generated voltage or the movement of charges is sufficient to trigger a neural reaction or a cellular physiological reaction.

19. The method according to claim 16, further comprising bringing the second inductor into proximity with the body tissue or the other body tissue, or bringing the body tissue or the other body tissue into proximity with the second inductor, in a manner that the second magnetic field is present in the body tissue or the other body tissue.

20. An apparatus for use with a first inductor and a second inductor, the first inductor for generating a magnetic field for application to body tissue, the apparatus comprising:

an electric storage device configured to store electrical energy;

a first terminal for connection to the first inductor for generating a first magnetic field for application to the body tissue;

a second terminal for connection to the second inductor for generating a second magnetic field;

connecting circuitry between the electric storage device and the first and second terminals, wherein the connecting circuitry comprises at least a first branch leading to the first terminal and a second branch leading to the second terminal;

a first switch, wherein the first switch forms part of the first branch, wherein the first switch is configured to electrically connect the electric storage device to the first terminal to enable electrical current to flow through the first branch and through the first inductor via said first terminal while the first inductor is connected to the apparatus via said first terminal, due to the electrical energy stored by the electric storage device, and configured to cause the first inductor to generate the first magnetic field, wherein the electrical current flowing through the first branch represents a first current direction of current flow with respect to the electric storage device; and a second switch, wherein the second switch forms part of the second branch, wherein the second switch is configured to electrically connect the electric storage device to the second terminal to enable electrical current to flow through the second branch and through the second inductor via said second terminal while the second inductor is connected to the apparatus via said second terminal, due to the electrical energy stored by the electric storage device, and configured to cause the second inductor to generate the second magnetic field, wherein the electrical current flowing through the second branch represents a second current direction of current flow with respect to the electric storage device, wherein the second current direction of current flow is opposite the first current direction of current flow, wherein the apparatus is configured for operation in a pulsed manner, wherein the electrical current that flows through the first branch during the pulsed manner of operation of the apparatus represents a first half pulse and wherein the electrical current that flows through the second branch during the pulsed manner of operation of the apparatus represents a second half pulse, the first half pulse and the second half pulse together forming a pulse.

* * * * *